US008936787B2

(12) United States Patent
Remaley et al.

(10) Patent No.: US 8,936,787 B2
(45) Date of Patent: Jan. 20, 2015

(54) PEPTIDES PROMOTING LIPID EFFLUX

(75) Inventors: Alan T. Remaley, Bethesda, MD (US); Marcelo J. A. Amar, Gaithersburg, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 829 days.

(21) Appl. No.: 12/937,974

(22) PCT Filed: Apr. 14, 2009

(86) PCT No.: PCT/US2009/040560
§ 371 (c)(1),
(2), (4) Date: Oct. 14, 2010

(87) PCT Pub. No.: WO2009/129263
PCT Pub. Date: Oct. 22, 2009

(65) Prior Publication Data
US 2011/0033518 A1 Feb. 10, 2011

Related U.S. Application Data

(60) Provisional application No. 61/045,213, filed on Apr. 15, 2008.

(51) Int. Cl.
*A61K 38/16* (2006.01)
*C07K 14/00* (2006.01)
*C07K 14/775* (2006.01)

(52) U.S. Cl.
CPC .................................. *C07K 14/775* (2013.01)
USPC ......... 424/192.1; 514/1.1; 514/7.4; 514/21.3; 530/300

(58) Field of Classification Search
None
See application file for complete search history.

(56) References Cited

U.S. PATENT DOCUMENTS

| 4,643,988 | A | 2/1987 | Segrest et al. |
| 5,733,879 | A | 3/1998 | Rosseneu et al. |
| 6,046,166 | A | 4/2000 | Dasseux et al. |
| 6,156,727 | A | 12/2000 | Garber et al. |
| 6,376,464 | B1 | 4/2002 | Dasseux et al. |
| 6,518,412 | B1 | 2/2003 | Dasseux et al. |
| 6,573,239 | B1 | 6/2003 | Dasseux et al. |
| 6,602,854 | B1 | 8/2003 | Dasseux et al. |
| 6,630,450 | B1 | 10/2003 | Dasseux et al. |
| 2003/0022901 | A1 | 1/2003 | Childrens et al. |
| 2003/0191057 | A1 | 10/2003 | Fogelman et al. |
| 2005/0202532 | A1 | 9/2005 | Bielicki et al. |

FOREIGN PATENT DOCUMENTS

DE 3436928 4/1986
WO WO 2006/044596 4/2006

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Bolanos-Garcia and Nunez, "On the structure and function of apolipoproteins: more than a family of lipid-binding proteins," *Progress in Biophysics and Molecular Biology*, 83(1):47-68, 2003.
Brewer, "High-Density Lipoproteins: A New Potential Therapeutic Target for the Prevention of Cardiovascular Disease," *Arterioscler. Thromb. Vasc. Biol.*, 24:387-391, 2004.
Datta et al., "Effects of increasing hydrophobicity on the physical-chemical and biological properties of a class A amphipathic helical peptide," *Journal of Lipid Research*, 42:1096-1104, 2001.
Eisenberg et al., "Hydrophobic Moments and Protein Structure," *Faraday Symp. Chem. Soc.*, 17:109-120, 1982.
Eisenberg et al., "Analysis of membrane and surface protein sequences with the hydrophobic moment plot," *J. Mol. Biol.*, 179(1):125-142, 1984.
Eisenberg et al., "The hydrophobic moment detects periodicity in protein hydrophobicity," *Proc. Natl. Acad. Sci. U.S.A.*, 81(1):140-144, 1984.
Fitzgerald et al., "Naturally occurring mutations in the largest extracellular loops of ABCA1 can disrupt its direct interaction with apolipoprotein A-I," *J. Biol. Chem.*, 277(36):33178-33187, 2002.
Garber et al., "A new synthetic class A amphipathic peptide analogue protects mice from diet-induced atherosclerosis," *Journal of Lipid Research*, 42:545-552, 2001.
Kanellis et al., "Studies of Synthetic Peptide Analogs of the Amphipathic Helix," *J. Biol. Chem.*, 255:11464-11472, 1980.
Kyte and Doolittle, "A simple method for displaying the hydropathic character of a protein," *J. Mol. Biol.*, 157:105-132, 1982.
Labeur et al., "Design of a New Class of Amphipathic Helical Peptides for the Plasma Apolipoproteins That Promote Cellular Cholesterol Efflux But Do Not Activate LCAT," *Arterioscler. Thromb. Vasc. Biol.*, 17:580-588, 1997.
Mendez et al., "Synthetic amphipathic helical peptides that mimic apolipoprotein A-I in clearing cellular cholesterol," *J. Clin. Invest.*, 94(4):1698-1705, 1994.

(Continued)

*Primary Examiner* — Christine J Saoud
*Assistant Examiner* — Jon M Lockard
(74) *Attorney, Agent, or Firm* — Klarquist Sparkman, LLP

(57) ABSTRACT

Disclosed herein are peptides and peptide analogs with multiple amphipathic α-helical domains that promote lipid efflux from cells via an ABCA1-dependent pathway, as well as peptides that activate lipoprotein lipase, and compositions comprising such peptides or combinations thereof. Also provided herein are methods of using multi-domain amphipathic α-helical peptides or peptide analogs to treat or inhibit dyslipidemic disorders. Methods for identifying non-cytotoxic peptides that promote ABCA1-dependent lipid efflux from cells and activate lipoprotein lipase within cells are also disclosed herein.

20 Claims, 21 Drawing Sheets

(56) References Cited

OTHER PUBLICATIONS

Mishra et al., "Effect of the Arrangement of Tandem Repeating Units of Class A Amphipathic α-Helixes on Lipid Interaction," *J. Biol. Chem.*, 270(4):1602-1611, 1995.

Mishra et al., "Studies of Synthetic Peptides of Human Apolipoprotein A-I Containing Tandem Amphipathic α-Helixes," *Biochem.*, 37:10313-10324, 1998.

Nissen et al., "Effect of Recombinant ApoA-I Milano on Coronary Atherosclerosis in Patients With Acute Coronary Syndromes," *JAMA*, 290(17):2292-2300, 2003.

Nilsson-Ehle et al., "Lipolytic Enzymes and Plasma Lipoprotein Metabolism," Ann. Rev. Biochem., vol. 49, pp. 667-693, 1980.

Panagotopulos et al., "The Role of Apolipoprotein A-I Helix 10 in Apolipoprotein-mediated Cholesterol Efflux via the ATP-binding Cassette Transporter," *J. Biol. Chem.*, 277(42):39477-39484, 2002.

Remaley et al., "Synthetic amphipathic helical peptides promote lipid efflux from cells by an ABCA1-dependent and an ABCA1-independent pathway," *J. Lipid Res.*, 44(4):828-836, 2003.

Rubin et al., "Inhibition of early atherogenesis in transgenic mice by human apolipoprotein AI" *Nature*, 353:265-267, 1991.

Segrest et al., "The amphipathic helix in the exchangeable apolipoproteins: a review of secondary structure and function" *J. Lipid Res.* 33: 141-166, 1992.

Sethi et al., "Asymmetry in the Lipid Affinity of Bihelical Amphipathic Peptides," *Journal of Biological Chemistry*, vol. 283, No. 47, pp. 32273-32282, 2008.

Tossi et al., "New consensus hydrophobicity scale extended to non-proteinogenic amino acids," *Peptides*, Ettore Benedetti and Carlo Pedone (Eds.), Napoli, Italy, 2002, 2 pages.

Wang et al., "The helix-hinge-helix structural motif in human apolipoprotein A-I determined by NMR spectroscopy," *Biochem.*, 36(44):13657-13666, 1997.

\* cited by examiner

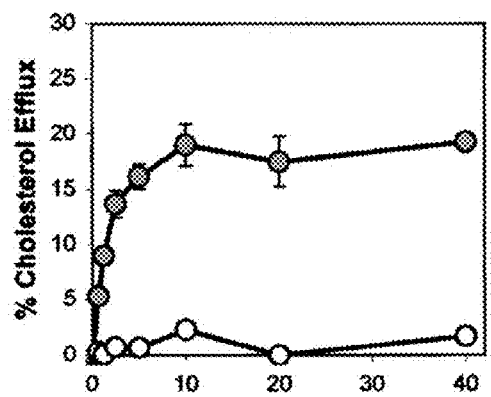
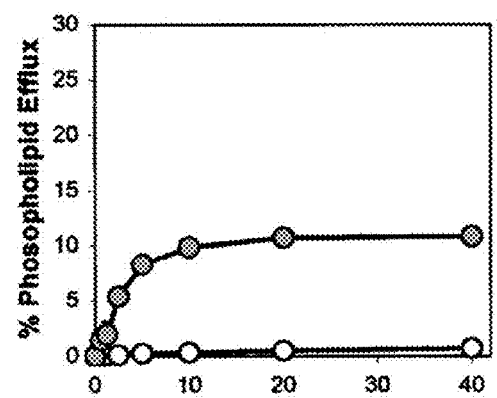
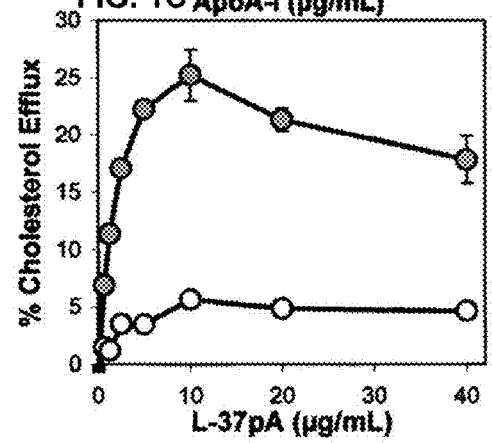
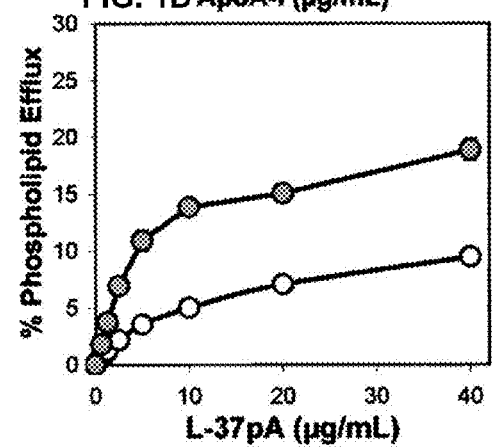
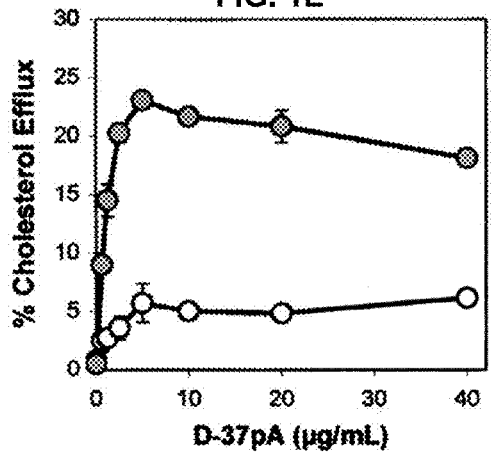
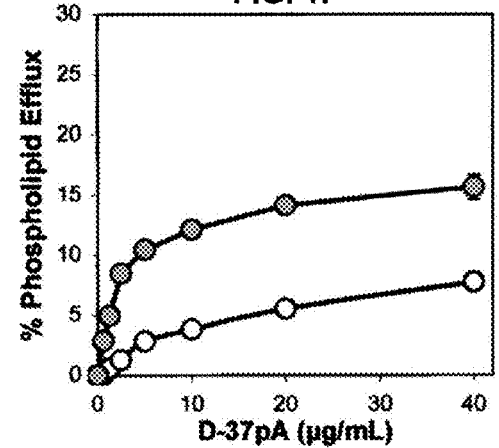

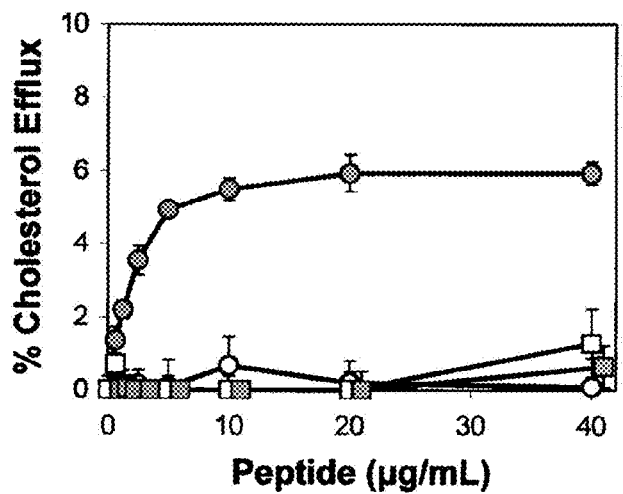
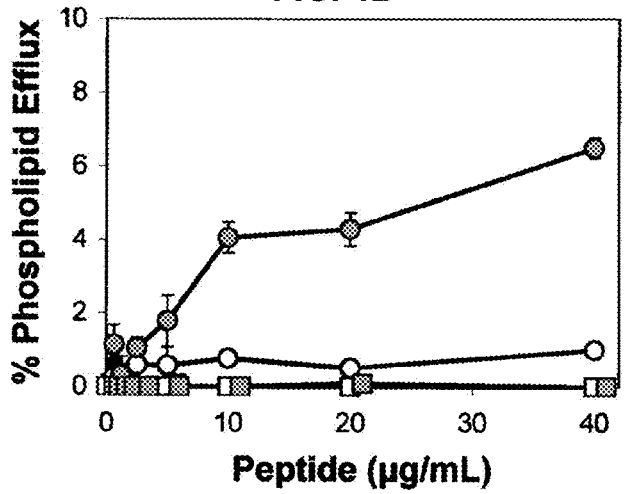
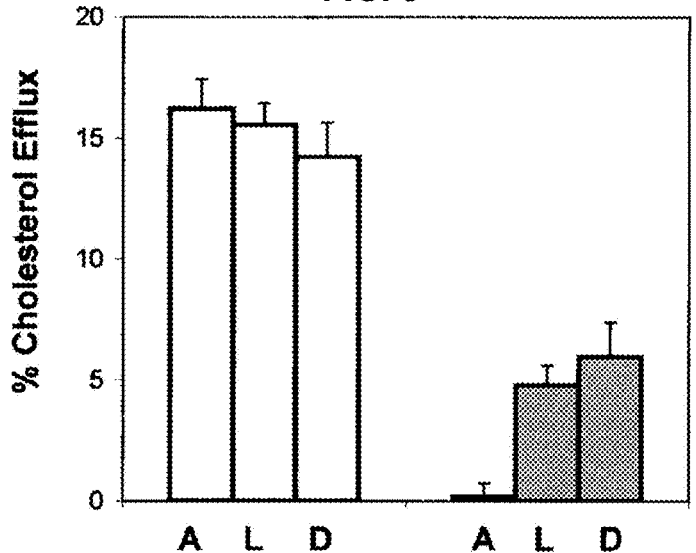

Atherosclerosis measurement in ApoE KO mice after 12 weeks of treatment

SEQUENCE LISTING

```
<160> NUMBER OF SEQ ID NOS: 75

<210> SEQ ID NO 1
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 1

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 2
<211> LENGTH: 42
<212> TYPE: PRT
<213> ORGANISM: Artificial Sequence
<220> FEATURE:
<223> OTHER INFORMATION: Gamma crystalline peptide.

<400> SEQUENCE: 2

Arg Met Arg Ile Thr Glu Arg Asp Phe Arg Gly Gln Met Ser Glu
1               5                   10                  15

Ile Thr Asp Asp Cys Pro Ser Leu Gln Asp Arg Phe His Leu Thr Glu
            20                  25                  30

Val His Ser Leu Arg Val Leu Glu Gly Ser
        35                  40

<210> SEQ ID NO 3
```

-continued

```
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 3

Asp Trp Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
        35

<210> SEQ ID NO 4
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 4

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Ala Lys Glu Ala Phe
        35

<210> SEQ ID NO 5
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 5

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Ala Lys Glu Ala Ala
        35

<210> SEQ ID NO 6
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 6

Asp Trp Leu Lys Ala Phe Tyr Asp Lys Val Ala Glu Lys Leu Lys Glu
1               5                   10                  15

Ala Phe Pro Asp Trp Leu Lys Ala Ala Tyr Asp Lys Val Ala Glu Lys
            20                  25                  30

Ala Lys Glu Ala Ala
        35

<210> SEQ ID NO 7
<211> LENGTH: 37
<212> TYPE: PRT
<213> ORGANISM: Artificial Sequence
```

-continued

```
<220> FEATURE:
<223> OTHER INFORMATION: Multi-domain amphipathic helical peptide.

<400> SEQUENCE: 7

Asp Trp Leu Lys Ala Phe Tyr Asp Lys Val Ala Glu Lys Leu Lys Glu
1               5                   10                  15

Ala Phe Pro Asp Trp Leu Lys Ala Ala Tyr Asp Lys Ala Ala Glu Lys
            20                  25                  30

Ala Lys Glu Ala Ala
        35

<210> SEQ ID NO 8
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 8

Asp Trp Leu Lys Ala Phe Tyr Asp Lys Val Ala Glu Lys Leu Lys Glu
1               5                   10                  15

Ala Phe Pro Asp Trp Gly Lys Ala Gly Tyr Asp Lys Gly Ala Glu Lys
            20                  25                  30

Gly Lys Glu Ala Gly
        35

<210> SEQ ID NO 9
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 9

Asp Trp Leu Lys Ala Phe Tyr Asp Lys Val Ala Glu Lys Leu Lys Glu
1               5                   10                  15

Ala Phe Pro Asp Trp Gly Lys Ala Gly Tyr Asp Lys Gly Ala Glu Lys
            20                  25                  30

Gly Lys Glu Ala Phe
        35

<210> SEQ ID NO 10
<211> LENGTH: 36
<212> TYPE: PRT
<213> ORGANISM: Artificial Sequence
<220> FEATURE:
<223> OTHER INFORMATION: Multi-domain amphipathic helical peptide.

<400> SEQUENCE: 10

Asp Trp Gly Lys Ala Gly Tyr Asp Lys Gly Ala Glu Lys Gly Lys Glu
1               5                   10                  15

Ala Gly Asp Trp Leu Lys Ala Phe Tyr Asp Lys Val Ala Glu Lys Leu
            20                  25                  30

Lys Glu Ala Phe
        35

<210> SEQ ID NO 11
<211> LENGTH: 34
<212> TYPE: PRT
<213> ORGANISM: Artificial Sequence
<220> FEATURE:
<223> OTHER INFORMATION: Multi-domain amphipathic helical peptide.
```

```
<400> SEQUENCE: 11

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys

<210> SEQ ID NO 12
<211> LENGTH: 34
<212> TYPE: PRT
<213> ORGANISM: Artificial Sequence
<220> FEATURE:
<223> OTHER INFORMATION: Multi-domain amphipathic helical peptide.

<400> SEQUENCE: 12

Lys Ala Phe Tyr Asp Lys Val Ala Glu Lys Leu Lys Glu Ala Phe Pro
1               5                   10                  15

Asp Trp Leu Lys Ala Phe Tyr Asp Lys Val Ala Glu Lys Leu Lys Glu
            20                  25                  30

Ala Phe

<210> SEQ ID NO 13
<211> LENGTH: 30
<212> TYPE: PRT
<213> ORGANISM: Artificial Sequence
<220> FEATURE:
<223> OTHER INFORMATION: Multi-domain amphipathic helical peptide.

<400> SEQUENCE: 13

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Multi-domain amphipathic helical peptide.

<400> SEQUENCE: 14

Asp Lys Val Ala Glu Lys Leu Lys Glu Ala Phe Pro Asp Trp Leu Lys
1               5                   10                  15

Ala Phe Tyr Asp Lys Val Ala Glu Lys Leu Lys Glu Ala Phe
            20                  25                  30

<210> SEQ ID NO 15
<211> LENGTH: 36
<212> TYPE: PRT
<213> ORGANISM: Artificial Sequence
<220> FEATURE:
<223> OTHER INFORMATION: Multi-domain amphipathic helical peptide.

<400> SEQUENCE: 15

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Lys Val Ala Glu Lys Leu
            20                  25                  30

Lys Glu Ala Phe
        35
```

```
<210> SEQ ID NO 16
<211> LENGTH: 35
<212> TYPE: PRT
<213> ORGANISM: Artificial Sequence
<220> FEATURE:
<223> OTHER INFORMATION: Multi-domain amphipathic helical peptide.

<400> SEQUENCE: 16

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Val Ala Glu Lys Leu Lys
                20                  25                  30

Glu Ala Phe
        35

<210> SEQ ID NO 17
<211> LENGTH: 36
<212> TYPE: PRT
<213> ORGANISM: Artificial Sequence
<220> FEATURE:
<223> OTHER INFORMATION: Multi-domain amphipathic helical peptide.

<400> SEQUENCE: 17

Asp Trp Leu Ala Phe Tyr Asp Lys Val Ala Glu Lys Leu Lys Glu Ala
1               5                   10                  15

Phe Pro Asp Trp Leu Lys Ala Phe Tyr Asp Lys Val Ala Glu Lys Leu
                20                  25                  30

Lys Glu Ala Phe
        35

<210> SEQ ID NO 18
<211> LENGTH: 35
<212> TYPE: PRT
<213> ORGANISM: Artificial Sequence
<220> FEATURE:
<223> OTHER INFORMATION: Multi-domain amphipathic helical peptide.

<400> SEQUENCE: 18

Asp Trp Leu Phe Tyr Asp Lys Val Ala Glu Lys Leu Lys Glu Ala Phe
1               5                   10                  15

Pro Asp Trp Leu Lys Ala Phe Tyr Asp Lys Val Ala Glu Lys Leu Lys
                20                  25                  30

Glu Ala Phe
        35

<210> SEQ ID NO 19
<211> LENGTH: 38
<212> TYPE: PRT
<213> ORGANISM: Artificial Sequence
<220> FEATURE:
<223> OTHER INFORMATION: Multi-domain amphipathic helical peptide.

<400> SEQUENCE: 19

Asp Trp Leu Lys Ala Phe Tyr Asp Lys Val Ala Glu Lys Leu Lys Glu
1               5                   10                  15

Ala Phe Pro Asp Trp Leu Ala Lys Ala Phe Tyr Asp Lys Val Ala Glu
                20                  25                  30

Lys Leu Lys Glu Ala Phe
        35

<210> SEQ ID NO 20
<211> LENGTH: 39
```

-continued

```
<212> TYPE: PRT
<213> ORGANISM: Artificial Sequence
<220> FEATURE:
<223> OTHER INFORMATION: Multi-domain amphipathic helical peptide.

<400> SEQUENCE: 20

Asp Trp Leu Lys Ala Phe Tyr Asp Lys Val Ala Glu Lys Leu Lys Glu
1               5                   10                  15

Ala Phe Pro Asp Trp Leu Ala Ala Lys Ala Phe Tyr Asp Lys Val Ala
            20                  25                  30

Glu Lys Leu Lys Glu Ala Phe
        35

<210> SEQ ID NO 21
<211> LENGTH: 38
<212> TYPE: PRT
<213> ORGANISM: Artificial Sequence
<220> FEATURE:
<223> OTHER INFORMATION: Multi-domain amphipathic helical peptide.

<400> SEQUENCE: 21

Asp Trp Leu Lys Ala Ala Phe Tyr Asp Lys Val Ala Glu Lys Leu Lys
1               5                   10                  15

Glu Ala Phe Pro Asp Trp Leu Lys Ala Phe Tyr Asp Lys Val Ala Glu
            20                  25                  30

Lys Leu Lys Glu Ala Phe
        35

<210> SEQ ID NO 22
<211> LENGTH: 39
<212> TYPE: PRT
<213> ORGANISM: Artificial Sequence
<220> FEATURE:
<223> OTHER INFORMATION: Multi-domain amphipathic helical peptide.

<400> SEQUENCE: 22

Asp Trp Leu Lys Ala Ala Ala Phe Tyr Asp Lys Val Ala Glu Lys Leu
1               5                   10                  15

Lys Glu Ala Phe Pro Asp Trp Leu Lys Ala Phe Tyr Asp Lys Val Ala
            20                  25                  30

Glu Lys Leu Lys Glu Ala Phe
        35

<210> SEQ ID NO 23
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 23

Asp Trp Leu Lys Ala Phe Tyr Asp Lys Val Ala Glu Lys Leu Lys Glu
1               5                   10                  15

Ala Phe Pro Asp Trp Leu Glu Ala Phe Tyr Asp Lys Val Ala Lys Lys
            20                  25                  30

Leu Lys Glu Ala Phe
        35

<210> SEQ ID NO 24
<211> LENGTH: 37
<212> TYPE: PRT
<213> ORGANISM: Artificial Sequence
<220> FEATURE:
```

<223> OTHER INFORMATION: Multi-domain amphipathic helical peptide.

<400> SEQUENCE: 24

Asp Trp Leu Lys Ala Phe Tyr Asp Lys Val Ala Glu Lys Leu Lys Glu
1               5                   10                  15

Ala Phe Pro Asp Trp Leu Glu Ala Phe Tyr Asp Glu Val Ala Lys Lys
            20                  25                  30

Leu Lys Lys Ala Phe
        35

<210> SEQ ID NO 25
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 25

Asp Trp Leu Glu Ala Phe Tyr Asp Lys Val Ala Lys Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 26
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 26

Asp Trp Leu Glu Ala Phe Tyr Asp Glu Val Ala Lys Lys Leu Lys Lys
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 27
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 27

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 28
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 28

```
Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
            35

<210> SEQ ID NO 29
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 29

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
            35

<210> SEQ ID NO 30
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 30

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
            35

<210> SEQ ID NO 31
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 31

Leu Leu Asp Asn Trp Asp Ser Val Thr Ser Thr Phe Ser Lys Leu Arg
1               5                   10                  15

Glu Gln Pro Asp Trp Ala Lys Ala Ala Tyr Asp Lys Ala Ala Glu Lys
            20                  25                  30

Ala Lys Glu Ala Ala
            35

<210> SEQ ID NO 32
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 32

Leu Glu Ser Phe Lys Val Ser Phe Leu Ser Ala Leu Glu Glu Tyr Thr
1               5                   10                  15
```

```
Lys Lys Pro Asp Trp Ala Lys Ala Ala Tyr Asp Lys Ala Ala Glu Lys
            20                  25                  30

Ala Lys Glu Ala Ala
        35

<210> SEQ ID NO 33
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 33

Asp Trp Ala Lys Ala Ala Tyr Asp Lys Ala Ala Glu Lys Ala Lys Glu
1               5                   10                  15

Ala Ala Pro Leu Leu Asp Asn Trp Asp Ser Val Thr Ser Thr Phe Ser
            20                  25                  30

Lys Leu Arg Glu Gln
        35

<210> SEQ ID NO 34
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 34

Asp Trp Ala Lys Ala Ala Tyr Asp Lys Ala Glu Lys Ala Lys Glu
1               5                   10                  15

Ala Ala Pro Leu Glu Ser Phe Lys Val Ser Phe Leu Ser Ala Leu Glu
            20                  25                  30

Glu Tyr Thr Lys Lys
        35

<210> SEQ ID NO 35
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 35

Asp Trp Leu Lys Ala Phe Tyr Asp Lys Val Ala Glu Lys Leu Lys Glu
1               5                   10                  15

Ala Phe Pro Ser Asp Glu Leu Arg Gln Arg Leu Ala Ala Arg Leu Glu
            20                  25                  30

Ala Leu Lys Glu Asn
        35

<210> SEQ ID NO 36
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 36

Asp Trp Leu Lys Ala Phe Tyr Asp Lys Val Ala Glu Lys Leu Lys Glu
1               5                   10                  15

Ala Phe Pro Arg Ala Glu Leu Gln Glu Gly Ala Arg Gln Lys Leu His
            20                  25                  30
```

```
Glu Leu Gln Glu Lys
        35

<210> SEQ ID NO 37
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 37

Ser Asp Glu Leu Arg Gln Arg Leu Ala Ala Arg Leu Glu Ala Leu Lys
1               5                   10                  15

Glu Asn Pro Asp Trp Leu Lys Ala Phe Tyr Asp Lys Val Ala Glu Lys
            20                  25                  30

Leu Lys Glu Ala Phe
        35

<210> SEQ ID NO 38
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 38

Arg Ala Glu Leu Gln Glu Gly Ala Arg Gln Lys Leu His Glu Leu Gln
1               5                   10                  15

Glu Lys Pro Asp Trp Leu Lys Ala Phe Tyr Asp Lys Val Ala Glu Lys
            20                  25                  30

Leu Lys Glu Ala Phe
        35

<210> SEQ ID NO 39
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 39

Leu Leu Asp Asn Trp Asp Ser Val Thr Ser Thr Phe Ser Lys Leu Arg
1               5                   10                  15

Glu Gln Pro Ser Asp Glu Leu Arg Gln Arg Leu Ala Ala Arg Leu Glu
            20                  25                  30

Ala Leu Lys Glu Asn
        35

<210> SEQ ID NO 40
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 40

Leu Glu Ser Phe Lys Val Ser Phe Leu Ser Ala Leu Glu Glu Tyr Thr
1               5                   10                  15

Lys Lys Pro Arg Ala Glu Leu Gln Glu Gly Ala Arg Gln Lys Leu His
            20                  25                  30

Glu Leu Gln Glu Lys
        35
```

```
<210> SEQ ID NO 41
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 41

Ser Asp Glu Leu Arg Gln Arg Leu Ala Ala Arg Leu Glu Ala Leu Lys
1               5                   10                  15

Glu Asn Pro Leu Leu Asp Asn Trp Asp Ser Val Thr Ser Thr Phe Ser
            20                  25                  30

Lys Leu Arg Glu Gln
        35

<210> SEQ ID NO 42
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 42

Leu Leu Asp Asn Trp Asp Ser Val Thr Ser Thr Phe Ser Lys Leu Arg
1               5                   10                  15

Glu Gln Pro Leu Glu Ser Phe Lys Val Ser Phe Leu Ser Ala Leu Glu
            20                  25                  30

Glu Tyr Thr Lys Lys
        35

<210> SEQ ID NO 43
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 43

Asp Trp Leu Lys Ala Phe Tyr Asp Lys Val Ala Glu Lys Leu Lys Glu
1               5                   10                  15

Ala Phe Pro Asp Trp Leu Arg Ala Phe Tyr Asp Lys Val Ala Glu Lys
            20                  25                  30

Leu Lys Glu Ala Phe
        35

<210> SEQ ID NO 44
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 44

Asp Trp Leu Lys Ala Phe Tyr Asp Lys Val Ala Glu Lys Leu Lys Glu
1               5                   10                  15

Ala Phe Pro Asp Trp Leu Arg Ala Phe Tyr Asp Arg Val Ala Glu Lys
            20                  25                  30

Leu Lys Glu Ala Phe
        35

<210> SEQ ID NO 45
```

```
<211> LENGTH: 37
<212> TYPE: PRT
<213> ORGANISM: Artificial Sequence
<220> FEATURE:
<223> OTHER INFORMATION: Multi-domain amphipathic helical peptide.

<400> SEQUENCE: 45

Asp Trp Leu Lys Ala Phe Tyr Asp Lys Val Ala Glu Lys Leu Lys Glu
1               5                   10                  15

Ala Phe Pro Asp Trp Leu Arg Ala Phe Tyr Asp Arg Val Ala Glu Lys
            20                  25                  30

Leu Arg Glu Ala Phe
        35

<210> SEQ ID NO 46
<211> LENGTH: 4
<212> TYPE: PRT
<213> ORGANISM: Artificial Sequence
<220> FEATURE:
<223> OTHER INFORMATION: Heparin binding site.

<400> SEQUENCE: 46

Arg Lys Asn Arg
1

<210> SEQ ID NO 47
<211> LENGTH: 5
<212> TYPE: PRT
<213> ORGANISM: Artificial Sequence
<220> FEATURE:
<223> OTHER INFORMATION: Heparin binding site.

<400> SEQUENCE: 47

Lys Lys Trp Val Arg
1               5

<210> SEQ ID NO 48
<211> LENGTH: 3
<212> TYPE: PRT
<213> ORGANISM: Artificial Sequence
<220> FEATURE:
<223> OTHER INFORMATION: Integrin binding site.

<400> SEQUENCE: 48

Arg Gly Asp
1

<210> SEQ ID NO 49
<211> LENGTH: 9
<212> TYPE: PRT
<213> ORGANISM: Artificial Sequence
<220> FEATURE:
<223> OTHER INFORMATION: P-selectin site.

<400> SEQUENCE: 49

Asp Val Glu Trp Val Asp Val Ser Tyr
1               5

<210> SEQ ID NO 50
<211> LENGTH: 12
<212> TYPE: PRT
<213> ORGANISM: Artificial Sequence
<220> FEATURE:
<223> OTHER INFORMATION: TAT HIV sequence.

<400> SEQUENCE: 50
```

```
Arg Lys Lys Arg Arg Gln Arg Arg Pro Pro Gln
1               5                   10
```

<210> SEQ ID NO 51
<211> LENGTH: 9
<212> TYPE: PRT
<213> ORGANISM: Artificial Sequence
<220> FEATURE:
<223> OTHER INFORMATION: TAT HIV sequence.

<400> SEQUENCE: 51

```
Arg Arg Arg Gln Arg Arg Lys Lys Arg
1               5
```

<210> SEQ ID NO 52
<211> LENGTH: 5
<212> TYPE: PRT
<213> ORGANISM: Artificial Sequence
<220> FEATURE:
<223> OTHER INFORMATION: Panning sequence.
<220> FEATURE:
<221> NAME/KEY: MISC_FEATURE
<222> LOCATION: (4)..(4)
<223> OTHER INFORMATION: "Xaa" is any amino acid.

<400> SEQUENCE: 52

```
Arg Arg Pro Xaa Arg
1               5
```

<210> SEQ ID NO 53
<211> LENGTH: 16
<212> TYPE: PRT
<213> ORGANISM: Artificial Sequence
<220> FEATURE:
<223> OTHER INFORMATION: Penatratin sequence.

<400> SEQUENCE: 53

```
Arg Gln Ile Lys Ile Trp Phe Gln Asn Arg Arg Met Lys Trp Lys Lys
1               5                   10                  15
```

<210> SEQ ID NO 54
<211> LENGTH: 30
<212> TYPE: PRT
<213> ORGANISM: Artificial Sequence
<220> FEATURE:
<223> OTHER INFORMATION: SAA C-terminus sequence.

<400> SEQUENCE: 54

```
Gly His Glu Asp Thr Met Ala Asp Gln Glu Ala Asn Arg His Gly Arg
1               5                   10                  15

Ser Gly Gly Asp Pro Asn Tyr Tyr Arg Pro Pro Gly Gly Tyr
                20                  25                  30
```

<210> SEQ ID NO 55
<211> LENGTH: 20
<212> TYPE: PRT
<213> ORGANISM: Artificial Sequence
<220> FEATURE:
<223> OTHER INFORMATION: SAA N-terminus sequence.

<400> SEQUENCE: 55

```
Gly Phe Phe Ser Phe Ile Gly Glu Ala Phe Gln Gly Ala Gly Asp Met
1               5                   10                  15

Trp Arg Ala Tyr
                20
```

```
<210> SEQ ID NO 56
<211> LENGTH: 11
<212> TYPE: PRT
<213> ORGANISM: Artificial Sequence
<220> FEATURE:
<223> OTHER INFORMATION: LDL receptor sequence.

<400> SEQUENCE: 56

Lys Ala Glu Tyr Lys Lys Asn Lys His Arg His
1               5                   10

<210> SEQ ID NO 57
<211> LENGTH: 11
<212> TYPE: PRT
<213> ORGANISM: Artificial Sequence
<220> FEATURE:
<223> OTHER INFORMATION: LDL receptor sequence.

<400> SEQUENCE: 57

Tyr Thr Arg Leu Thr Arg Lys Arg Gly Leu Lys
1               5                   10

<210> SEQ ID NO 58
<211> LENGTH: 18
<212> TYPE: PRT
<213> ORGANISM: Artificial Sequence
<220> FEATURE:
<223> OTHER INFORMATION: Modified 18A sequence.

<400> SEQUENCE: 58

Asp Trp Leu Lys Ala Phe Tyr Cys Lys Val Ala Glu Lys Leu Lys Glu
1               5                   10                  15

Ala Phe

<210> SEQ ID NO 59
<211> LENGTH: 18
<212> TYPE: PRT
<213> ORGANISM: Artificial Sequence
<220> FEATURE:
<223> OTHER INFORMATION: Modified 18A sequence.

<400> SEQUENCE: 59

Asp Trp Leu Lys Ala Phe Tyr Asp Lys Val Ala Glu Lys Leu Lys Cys
1               5                   10                  15

Ala Phe

<210> SEQ ID NO 60
<211> LENGTH: 19
<212> TYPE: PRT
<213> ORGANISM: Artificial Sequence
<220> FEATURE:
<223> OTHER INFORMATION: ApoA-I Milano sequence.

<400> SEQUENCE: 60

Tyr Ser Asp Gly Leu Arg Gln Cys Leu Ala Ala Arg Leu Asp Ala Leu
1               5                   10                  15

Lys Asp Arg

<210> SEQ ID NO 61
<211> LENGTH: 6
<212> TYPE: PRT
<213> ORGANISM: Artificial Sequence
<220> FEATURE:
<223> OTHER INFORMATION: 6x-His sequence.

<400> SEQUENCE: 61
```

```
His His His His His His
1               5

<210> SEQ ID NO 62
<211> LENGTH: 11
<212> TYPE: PRT
<213> ORGANISM: Artificial Sequence
<220> FEATURE:
<223> OTHER INFORMATION: Lactoferrin sequence.

<400> SEQUENCE: 62

Phe Gln Trp Gln Arg Asn Ile Arg Lys Val Arg
1               5                   10

<210> SEQ ID NO 63
<211> LENGTH: 29
<212> TYPE: PRT
<213> ORGANISM: Artificial Sequence
<220> FEATURE:
<223> OTHER INFORMATION: Synthetic peptide

<400> SEQUENCE: 63

Asp Leu Tyr Ser Lys Ser Thr Ala Ala Met Ser Thr Tyr Thr Gly Ile
1               5                   10                  15

Phe Thr Asp Gln Val Leu Ser Val Leu Lys Gly Glu Glu
            20                  25

<210> SEQ ID NO 64
<211> LENGTH: 24
<212> TYPE: PRT
<213> ORGANISM: Artificial Sequence
<220> FEATURE:
<223> OTHER INFORMATION: Synthetic peptide

<400> SEQUENCE: 64

Ser Thr Ala Ala Met Ser Thr Tyr Thr Gly Ile Phe Thr Asp Gln Val
1               5                   10                  15

Leu Ser Val Leu Lys Gly Glu Glu
            20

<210> SEQ ID NO 65
<211> LENGTH: 21
<212> TYPE: PRT
<213> ORGANISM: Artificial Sequence
<220> FEATURE:
<223> OTHER INFORMATION: Synthetic peptide

<400> SEQUENCE: 65

Ala Met Ser Thr Tyr Thr Gly Ile Phe Thr Asp Gln Val Leu Ser Val
1               5                   10                  15

Leu Lys Gly Glu Glu
            20

<210> SEQ ID NO 66
<211> LENGTH: 19
<212> TYPE: PRT
<213> ORGANISM: Artificial Sequence
<220> FEATURE:
<223> OTHER INFORMATION: Synthetic peptide

<400> SEQUENCE: 66

Ser Thr Tyr Thr Gly Ile Phe Thr Asp Gln Val Leu Ser Val Leu Lys
1               5                   10                  15

Gly Glu Glu
```

```
<210> SEQ ID NO 67
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (11)..(19)
<223> OTHER INFORMATION: Xaa can be any naturally occurring amino acid

<400> SEQUENCE: 67

Xaa Xaa Tyr Xaa Xaa Ile Xaa Xaa Asp Gln Xaa Xaa Xaa Xaa Xaa Xaa
1               5                   10                  15

Xaa Xaa Xaa

<210> SEQ ID NO 68
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 68

Ala Xaa Xaa Thr Tyr Xaa Gly Ile Xaa Xaa Asp Gln Val Leu Ser Val
1               5                   10                  15

Leu Lys Gly Glu Glu
            20

<210> SEQ ID NO 69
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
```

<400> SEQUENCE: 69

Xaa Xaa Tyr Xaa Xaa Ile Xaa Xaa Asp Gln
1               5                   10

<210> SEQ ID NO 70
<211> LENGTH: 48
<212> TYPE: PRT
<213> ORGANISM: Artificial Sequence
<220> FEATURE:
<223> OTHER INFORMATION: Synthetic peptide

<400> SEQUENCE: 70

Asp Trp Leu Lys Ala Phe Tyr Asp Lys Val Ala Glu Lys Leu Lys Glu
1               5                   10                  15

Ala Phe Pro Asp Leu Tyr Ser Lys Ser Thr Ala Ala Met Ser Thr Tyr
            20                  25                  30

Thr Gly Ile Phe Thr Asp Gln Val Leu Ser Val Leu Lys Gly Glu Glu
        35                  40                  45

<210> SEQ ID NO 71
<211> LENGTH: 43
<212> TYPE: PRT
<213> ORGANISM: Artificial Sequence
<220> FEATURE:
<223> OTHER INFORMATION: Synthetic peptide

<400> SEQUENCE: 71

Asp Trp Leu Lys Ala Phe Tyr Asp Lys Val Ala Glu Lys Leu Lys Glu
1               5                   10                  15

Ala Phe Pro Ser Thr Ala Ala Met Ser Thr Tyr Thr Gly Ile Phe Thr
            20                  25                  30

Asp Gln Val Leu Ser Val Leu Lys Gly Glu Glu
        35                  40

<210> SEQ ID NO 72
<211> LENGTH: 40
<212> TYPE: PRT
<213> ORGANISM: Artificial Sequence
<220> FEATURE:
<223> OTHER INFORMATION: Synthetic peptide

<400> SEQUENCE: 72

Asp Trp Leu Lys Ala Phe Tyr Asp Lys Val Ala Glu Lys Leu Lys Glu
1               5                   10                  15

Ala Phe Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 73
<211> LENGTH: 38
<212> TYPE: PRT
<213> ORGANISM: Artificial Sequence
<220> FEATURE:
<223> OTHER INFORMATION: Synthetic peptide

<400> SEQUENCE: 73

Asp Trp Leu Lys Ala Phe Tyr Asp Lys Val Ala Glu Lys Leu Lys Glu
1               5                   10                  15

Ala Phe Pro Ser Thr Tyr Thr Gly Ile Phe Thr Asp Gln Val Leu Ser
            20                  25                  30

```
Val Leu Lys Gly Glu Glu
        35

<210> SEQ ID NO 74
<211> LENGTH: 38
<212> TYPE: PRT
<213> ORGANISM: Artificial Sequence
<220> FEATURE:
<223> OTHER INFORMATION: Sythetic peptide
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (30)..(38)
<223> OTHER INFORMATION: Xaa can be any naturally occurring amino acid

<400> SEQUENCE: 74

Asp Trp Leu Lys Ala Phe Tyr Asp Lys Val Ala Glu Lys Leu Lys Glu
1               5                   10                  15

Ala Phe Pro Xaa Xaa Tyr Xaa Xaa Ile Xaa Xaa Asp Gln Xaa Xaa Xaa
            20                  25                  30

Xaa Xaa Xaa Xaa Xaa Xaa
        35

<210> SEQ ID NO 75
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid

<400> SEQUENCE: 75

Asp Trp Leu Lys Ala Phe Tyr Asp Lys Val Ala Glu Lys Leu Lys Glu
1               5                   10                  15

Ala Phe Pro Ala Xaa Xaa Thr Tyr Xaa Gly Ile Xaa Xaa Asp Gln Val
            20                  25                  30

Leu Ser Val Leu Lys Gly Glu Glu
        35                  40
```

PEPTIDES PROMOTING LIPID EFFLUX

CROSS REFERENCE TO RELATED APPLICATION

This is the U.S. National Stage of International Application No. PCT/US2009/040560, filed Apr. 14, 2009, which was published in English under PCT Article 21(2) on Oct. 22, 2009, which in turn claims the benefit of U.S. Provisional Application No. 61/045,213, filed Apr. 15, 2008, which is incorporated herein by reference in its entirety.

FIELD

This disclosure relates to peptides or peptide analogs with multiple amphipathic α-helical domains that promote lipid efflux from cells via an ABCA1-dependent pathway and activate lipoprotein lipase. The disclosure further relates to methods for characterizing multi-domain amphipathic α-helical peptides that promote lipid efflux from cells and activate lipoprotein lipase in cells. Multi-domain amphipathic α-helical peptides that promote lipid efflux from cells via an ABCA1-dependent pathway in a substantially non-cytotoxic manner (e.g., without causing significant hypertriglyceridemia) are useful in the treatment and prevention of dyslipidemic and vascular disorders.

BACKGROUND

Clearance of excess cholesterol from cells by high density lipoproteins (HDL) is facilitated by the interaction of HDL apolipoprotein with cell-surface binding sites or receptors (Mendez et al., *J. Clin. Invest.* 94:1698-1705, 1994), such as ABCA1 (Oram and Yokoyama, *J. Lipid Res.* 37:2473-2491, 1996). ABCA1 is a member of the ATP binding cassette transporter family (Dean and Chimini., *J. Lipid Res.* 42:1007-1017, 2001) and is expressed by many cell types (Langmann et al., *Biochem. Biophys. Res. Commun.* 257:29-33, 1999). Mutations in the ABCA1 transporter lead to Tangier disease, which is characterized by the accumulation of excess cellular cholesterol, low levels of HDL and an increased risk for cardiovascular disease (Rust et al., *Nat. Genet.* 22:352-355, 1999; Bodzioch et al., *Nat. Genet.* 22:347-351, 1999; Brooks-Wilson et al., *Nat. Genet.* 22:336-345, 1999; Remaley et al., *Proc. Natl. Acad. Sci. USA* 96:12685-12690, 1999; and Lawn et al., *J. Clin. Invest.* 104:R25-R31, 1999). Fibroblasts from Tangier disease patients are defective in the initial step of cholesterol and phospholipid efflux to extracellular apolipoproteins (Francis et al., *J. Clin. Invest.* 96:78-87, 1995 and Remaley et al., *Arterioscler. Thromb. Vasc. Biol.* 17:1813-1821, 1997).

Research has demonstrated an inverse correlation between the occurrence of atherosclerosis events and levels of HDL and its most abundant protein constituent, apolipoprotein A-I (apoA-I) (Panagotopulos et al., *J. Biol. Chem.* 277:39477-39484, 2002). ApoA-I has been shown to promote lipid efflux from ABCA1-transfected cells (Wang et al., *J. Biol. Chem.* 275:33053-33058, 2000; Hamon et al., *Nat. Cell Biol.* 2:399-406, 2000; and Remaley et al., *Biochem. Biophys. Res. Commun.* 280:818-823, 2001). However, the nature of the interaction between apoA-I and ABCA1 is not fully understood. Several other exchangeable-type apolipoproteins have also been shown to efflux lipid from ABCA1-transfected cells (Remaley et al., *Biochem. Biophys. Res. Commun.* 280:818-823, 2001). Although the exchangeable-type apolipoproteins do not share a similar primary amino acid sequence, they all contain amphipathic helices, a structural motif known to facilitate the interaction of proteins with lipids (Segrest et al., *J. Lipid Res.* 33:141-166, 1992 and Anantharamaiah et al., *J. Biol. Chem.* 260:10248-10255, 1985). Animal experiments have shown that intravenous injections of apoA-I or its variant, apoA-I Milano (which has a cysteine substitution at position 173 for arginine), produced significant regression of atherosclerosis (Rubin et al., *Nature* 353:265-267, 1991 and Nissen et al., *JAMA* 290:2292-2300, 2003). These results make apoA-1, or derivatives thereof, attractive as potential therapeutic compounds in the treatment and prevention of atherosclerosis.

Short synthetic peptide mimics of apolipoproteins have been used as a model for studying physical and biological properties of apolipoproteins (see, e.g., Fukushima et al., *J. Am. Chem. Soc.* 101:3703-3704, 1980; Kanellis et al., *J. Biol. Chem.* 255:11464-11472, 1980; and U.S. Pat. Nos. 4,643,988, and 6,376,464). These include, for instance, single helices taken from native apolipoproteins, synthetic amphipathic alpha helices (Kanellis et al., *J. Biol. Chem.* 255:11464-11472, 1980), and derivatives thereof. Examples of short synthetic amphipathic helical peptides have been shown to promote lipid efflux and inhibit atherosclerosis (Garber et al, *J. Lipid Res.* 42:545-552, 2001; Navab et al., *Circulation* 105:290-292, 2002; and U.S. Pat. No. 6,156,727). However, while some of these peptides exhibit beneficial effects in preventing atherosclerosis, they are also potentially cytotoxic (Remaley et al., *J. Lipid Res.* 44:828-836, 2003). It is believed that the cytotoxicity is caused by non-specific, ABCA1-independent lipid efflux from cells (Remaley et al., *J. Lipid Res.* 44:828-836, 2003). Therefore, there exists a need for non-cytotoxic synthetic peptide mimics of apolipoproteins that promote specific lipid efflux from cells by an ABCA1-dependent pathway for use in the treatment and prevention of cardiovascular diseases, such as atherosclerosis.

SUMMARY OF THE DISCLOSURE

Isolated peptides and peptide analogs including peptides with multiple amphipathic α-helical domains that promote lipid efflux from cells via an ABCA1-dependent pathway have been identified and are described herein. In various embodiments, a first amphipathic α-helical domain exhibits higher lipid affinity relative to a second amphipathic α-helical domain in the same peptide. In one example, the multi-domain peptide includes two amphipathic α-helical domains and the peptide comprises an amino acid sequence as set forth in any one of SEQ ID NOs: 3-45.

Also disclosed herein are isolated peptides and peptide analogs capable of promoting lipid efflux from cells by an ABCA1-dependent pathway which include a domain capable of activating lipoprotein lipase. In one embodiment, a peptide comprises a first domain that is an amphipathic α-helical domain that promotes lipid efflux from cells by an ABCA1-dependent pathway, and a second domain including an apoC-II protein, or a variant or fragment thereof that retains a lipoprotein lipase-activating property. For example, in some instances the first domain is an amphipathic α-helical domain with a hydrophobic moment score (Eisenberg scale; 100 degree-alpha helix) per residue of about 0.34 to about 0.60 and the second domain comprises an ApoC-II protein with an amino acid sequence set forth in any one of SEQ ID NOs: 63-69. In certain embodiments, the peptide or peptide analog includes an amino acid sequence as set forth in any one of SEQ ID NOs: 70-75. In other embodiments, these domains are provided in a single preparation (or mixture or combination of preparations), but the domains are not all covalently linked to each other; e.g., the domain capable of activating lipoprotein lipase is on a different peptide or protein than the domain(s) capable of promoting lipid efflux from cells by an ABAC1-dependent pathway.

Also described herein is a method of treating dyslipidemic and vascular disorders in a subject, including administering to the subject a therapeutically effective amount of the isolated multi-domain peptides or peptide analogs described herein. Dyslipidemic and vascular disorders amenable to treatment with the isolated multi-domain peptides disclosed herein include, but are not limited to, hyperlipidemia, hyperlipoproteinemia, hypercholesterolemia, hypertriglyceridemia, HDL deficiency, apoA-I deficiency, coronary artery disease, atherosclerosis, thrombotic stroke, peripheral vascular disease, restenosis, acute coronary syndrome, reperfusion myocardial injury, vasculitis, inflammation, or combinations of two or more thereof. In various embodiments, a peptide (or mixture of peptides) including a first domain with ABCA-1 dependent lipid efflux activity and a second domain with lipoprotein lipase activity is administered at a therapeutically effective concentration to prevent, inhibit or reduce a dyslipidemic or vascular disorder. In some embodiments, one of the disclosed peptides comprising an amino acid sequence set forth in any one of SEQ ID NOs: 70-75 is administered at a therapeutically effective concentration to prevent, inhibit or reduce a dylipidemic or vascular disorder. In other embodiments, one of the disclosed peptides including ABCA-1 dependent lipid efflux activity, such as a peptide comprising an amino acid sequence set forth in any one of SEQ ID NOs: 3-45, is administered at a therapeutically effective concentration in combination with a therapeutically effective concentration of a lipoprotein lipase activator, such as a peptide comprising an amino acid sequence set forth in any one of SEQ ID NOs:63-69, to prevent, inhibit or reduce a dylipidemic or vascular disorder. Optionally, such peptides are administered in combination with a peptide (or analog) that activates lipoprotein lipase. Representative lipoprotein lipase activating peptides are described.

A method for identifying substantially non-cytotoxic peptides that promotes ABCA1-dependent lipid efflux from cells and/or are capable of activating lipoprotein lipase is also described. In various embodiments, the method includes performing one of more cytotoxicity tests, one or more lipid efflux tests, and one or more lipoprotein lipase activity tests on ABCA1/liproprotein lipase-expressing and non-ABCA1/liproprotein lipase-expressing cells, thereby identifying one or more substantially non-cytotoxic peptides that promote ABCA1-dependent lipid efflux from cells and are capable of activating lipoprotein lipase in such cells. Example peptides for use in methods for identifying substantially non-cytotoxic peptides that promote ABCA1-dependent efflux from cells include peptides that contain two or more domains, such as an amphipathic α-helical domain that promotes lipid efflux from cells by an ABCA1-dependent pathway, and a ApoC-II protein domain, or a variant or fragment thereof that retains a lipoprotein lipase-activating property.

The foregoing and other features and advantages will become more apparent from the following detailed description of several embodiments, which proceeds with reference to the accompanying figures.

BRIEF DESCRIPTION OF THE FIGURES

FIGS. 1A-1F are a set of graphs illustrating lipid efflux by ABCA1 transfected cells and control cells treated with various peptides. ABCA1 transfected cells (closed circle) and control cells (open circle) were grown in alpha-MEM media with 10% FCS and were examined for their ability to efflux cholesterol (FIGS. 1A, 1C and 1E) and phospholipid (FIGS. 1B, 1D and 1F) over 18 hours to apoA-I (FIGS. 1A and 1B), L-37pA (FIGS. 1C and 1D), and D-37pA (FIGS. 1E and 1F). Results are expressed as the mean of triplicates ±1 SD.

FIGS. 4A-4B are a pair of graphs illustrating lipid efflux by ABCA1 transfected cells and control cells treated with mixed L- and D-amino acid 37pA peptides. ABCA1 transfected cells (closed symbols) and control cells (open symbols) were examined for their ability to efflux cholesterol (FIG. 4A) and phospholipid (FIG. 4B) over an 18 hour period when treated with 10 ng/ml L2D-37pA (closed circle, open circle) and 10 μg/ml L3D-37pA (closed square, open square). Results are expressed as the mean of triplicates ±1 SD.

FIG. 5 is a graph illustrating ABCA1-independent efflux of cholesterol from Tangier disease fibroblasts. Normal skin fibroblasts (open bars) and Tangier disease skin fibroblasts (solid bars) were examined for their ability to efflux cholesterol over an 18 hour period when treated with 10 μg/ml apoA-I (A), 10 μg/ml L-37pA (L), and 10 μg/ml D-37pA (D). Results are expressed as the mean of triplicates ±1 SD.

SEQUENCE LISTING

Figure 2A:
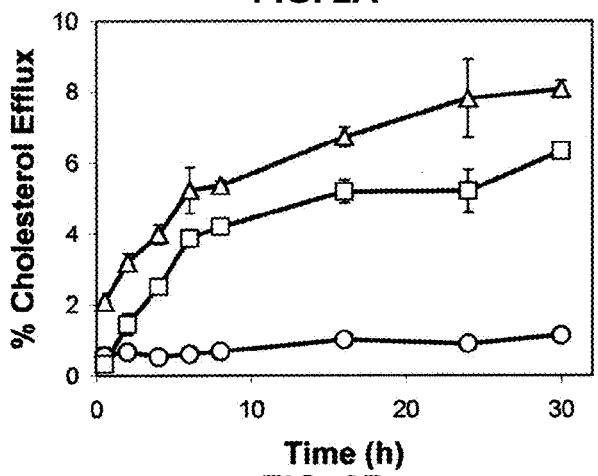
FIGS. 2A-2B are a pair of graphs illustrating the time course for lipid efflux by ABCA1 transfected cells and control cells treated with apoA-I and L-37pA. Cholesterol efflux from either ABCA1 transfected cells (FIG. 2A) or control cells (FIG. 2B) treated with 10 μg/ml apoA-I (square), 10 μg/ml L-37pA peptide (triangle), and blank media (circle) (α-MEM plus 1 mg/ml BSA) was determined at the time points indicated on the x axis. Results are expressed as the mean of triplicates ±1 SD.

The amino acid sequences listed in the accompanying sequence listing are shown using standard three letter code for amino acids, as defined in 37 C.F.R. §1.822. In the accompanying sequence listing:

SEQ ID NO: 1 shows the amino acid sequence of the 37pA peptide.

SEQ ID NO: 2 shows the amino acid sequence of the gamma crystalline peptide.

SEQ ID NOs: 3-45 show the amino acid sequences of a series of peptides with apoA-1-like activity; these are also discussed in Table 1.

SEQ ID NOs: 46-49 show the amino acid sequences of several cell recognition sequences.

SEQ ID NOs: 50-53 show the amino acid sequences of several cell internalization sequences.

SEQ ID NO: 54 shows the amino acid sequence of a neutral cholesterol esterase activation sequence.

SEQ ID NO: 55 shows the amino acid sequence of an ACAT inhibition sequence.

SEQ ID NOs: 56 and 57 show the amino acid sequences of a pair of LDL receptor sequences.

SEQ ID NOs: 58-60 show the amino acid sequences of several anti-oxidant sequences.

SEQ ID NOs: 61 and 62 show the amino acid sequences of a pair of metal chelation sequences.

SEQ ID NOs: 63-69 show the amino acid sequences of a series of apoC-II domains with apoC-II-like activity (e.g., lipoprotein lipase activating activity); these are also discussed in Tables 3 and 5.

SEQ ID NOs: 70-75 show the amino acid sequences of a series of peptides with apoA-1-like activity (e.g., promoting lipid efflux) and apoC-II like activity (e.g., lipoprotein lipase activating activity); these are also discussed in Table 4.

DETAILED DESCRIPTION

I. Abbreviations

ABCA1: ATP-binding cassette transporter A1
apoA-I: apolipoprotein A-I
apoC-II apolipoprotein C-II
DMPC: dimyristoyl phosphatidyl choline
FPLC: fast protein liquid chromatography
HDL: high-density lipoprotein
HPLC: high-pressure liquid chromatography
IV: intravenous
LDL: low-density lipoprotein
LPL: lipoprotein lipase
RBC: red blood cell
VLDL: very low density lipoprotein II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. The materials, methods and examples are illustrative only and not intended to be limiting.

In order to facilitate review of the various embodiments of this disclosure, the following explanations of specific terms are provided:

Alkane: A type of hydrocarbon, in which the molecule has the maximum possible number of hydrogen atoms, and therefore has no double bonds (i.e., they are saturated). The generic formula for acyclic alkanes, also known as aliphatic hydrocarbons is $C_nH_{2n+2}$; the simplest possible alkane is methane ($CH_4$).

Alkyl group: refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

Amphipathic: An amphipathic molecule contains both hydrophobic (non-polar) and hydrophilic (polar) groups. The hydrophobic group can be an alkyl group, such as a long carbon chain, for example, with the formula: $CH_3(CH_2)_n$, (where n is generally greater than or equal to about 4 to about 16). Such carbon chains also optionally comprise one or more branches, wherein a hydrogen is replaced with an aliphatic moiety, such as an alkyl group. A hydrophobic group also can comprise an aryl group. The hydrophilic group can be one or more of the following: an ionic molecule, such as an anionic molecule (e.g., a fatty acid, a sulfate or a sulfonate) or a cationic molecule, an amphoteric molecule (e.g., a phospholipid), or a non-ionic molecule (e.g., a small polymer).

One example of an amphipathic molecule is an amphipathic peptide. An amphipathic peptide can also be described as a helical peptide that has hydrophilic amino acid residues on one face of the helix and hydrophobic amino acid residues on the opposite face. Optionally, peptides described herein will form amphipathic helices in a physiological environment, such as for instance in the presence of lipid or a lipid interface.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology,* 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, e.g., Harlow and Lane, *Using Antibodies: A Laboratory Manual*, CSHL, New York, 1999).

Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Apolipoprotein C-II (apoC-II): A 79 amino acid protein, which plays a role in plasma lipid metabolism as an activator of lipoprotein lipase (LPL). This protein includes three amphipathic helices: helix 1, residues 16-38; helix 2, residues 45-58; and helix 3, residues 64-74. The lipase-activating region of apoC-II has previously been localized to the C-terminal domain of the sequence, from about residue 56, whereas the N-terminal domain (residues 1-50) of the sequence is involved in lipid binding.

In particular examples, apoC-II protein, fragment or variant thereof is capable of activating lipoprotein lipase. For example, an apoC-II protein, fragment or variant thereof is administered with apoA-1 or peptide mimics thereof to prevent, reduce or inhibit hypertriglyceridemia. Unless the context clearly indicates otherwise, the term apoC-II includes any apoC-II gene, cDNA, mRNA, or protein from any organism and is capable of activating lipoprotein lipase.

Nucleic acid and protein sequences for apoC-II are publicly available. For example, GenBank Accession No. NM_009695 (human) discloses an apoC-II nucleic acid sequence, and GenBank Accession Nos. AAH05348 (human), NP_001078821 (rat), NP_001095850 (bovine), and NP_033825 (mouse) disclose apoC-II protein sequences, all of which are incorporated by reference as provided by GenBank on Mar. 31, 2008.

In one example, apoC-II includes a full-length wild-type (or native) sequence. In other examples, apoC-II includes fragments of a wild-type (or native) sequence. In certain examples, apoC-II fragments include at least residues 51 to 79, such as 56 to 79, 59 to 79, or 61 to 79 of apoC-II.

In some examples, apoC-II variants include 19 amino acids with tyrosine at position 3, Ile at position 6, Asp at position 9, and Gln at position 10. In some examples, apoC-II has at least 20% sequence identity, for example, at least 25%, 30%, 40%, 45%, 50%, 55%, 60%, 70%, 80%, 85%, 90%, 95%, or 98% sequence identity to human apoC-II residues 59 to 79.

Domain: A domain of a protein is a part of a protein that shares common structural, physiochemical and functional features; for example hydrophobic, polar, globular, helical domains or properties, for example a DNA binding domain, an ATP binding domain, lipoprotein lipase activating domain, and the like. In a particular example, a peptide includes a first domain and a second domain (though they can occur in any order) in which the first domain is capable of promoting lipid efflux and the second domain is capable of activating lipoprotein lipase. For example, the first domain is an amphipathic α-helical domain which has a high hydrophobic moment and the second domain is an apoC-II protein, variant, or fragment thereof that is capable of activating lipoprotein lipase.

Dyslipidemic disorder: A disorder associated with any altered amount of any or all of the lipids or lipoproteins in the blood. Dyslipidemic disorders include, for example, hyperlipidemia, hyperlipoproteinemia, hypercholesterolemia, hypertriglyceridemia, HDL deficiency, apoA-I deficiency, and cardiovascular disease (i.e., coronary artery disease, atherosclerosis and restenosis).

Efflux: The process of flowing out. As applied to the results described herein, lipid efflux refers to a process whereby lipid, such as cholesterol and phospholipid, is complexed with an acceptor, such as an apolipoprotein or apolipoprotein peptide mimic, and removed from vesicles or cells. "ABCA1-dependent lipid efflux" (or lipid efflux by an "ABCA1-dependent pathway") refers to a process whereby apolipoproteins or peptide mimics of apolipoproteins bind to a cell and efflux lipid from the cell by a process that is facilitated by the ABCA1 transporter.

Helix: The molecular conformation of a spiral nature, generated by regularly repeating rotations around the backbone bonds of a macromolecule.

Hydrophobic: A hydrophobic (or lipophilic) group is electrically neutral and nonpolar, and thus prefers other neutral and nonpolar solvents or molecular environments. Examples of hydrophobic molecules include alkanes, oils and fats.

Hydrophobic moment ($\mu_H$): One measure of the degree of amphipathicity (i.e., the degree of asymmetry of hydrophobicity) in a peptide or other molecule; it is the vectorial sum of all the hydrophobicity indices for a peptide, divided by the number of residues. Thus, hydrophobic moment is the hydrophobicity of a peptide measured for different angles of rotation per amino acid residue. Methods for calculating $\mu_H$ for a particular peptide sequence are well-known in the art, and are described, for example, in Eisenberg et al., *Faraday Symp. Chem. Soc.* 17:109-120, 1982; Eisenberg et al., *J. Mol. Biol.* 179:125-142, 1984; and Kyte & Doolittle, *J. Mol. Biol.*, 157:105-132, 1982. The actual $\mu_H$ obtained for a particular peptide will depend on the type and total number of amino acid residues composing the peptide.

The amphipathicities of peptides of different lengths can be directly compared by way of the mean hydrophobic moment. The mean hydrophobic moment can be obtained by dividing $p_H$ by the number of residues in the helix.

The relative hydrophobic moment (μHrel) of a peptide is its hydrophobic moment relative to that of a perfectly amphipathic peptide. This measurement provides insight into the amphipathicity using different scales. For example, a value of 0.5 indicates that the peptide has about 50% of the maximum possible amphipathicity. For the CCS scale, the relative hydrophobic moment is calculated by creating a peptide made up only of Phe (Hi=+10) and Arg (Hi=−10), and placing them so as to obtain perfectly segregated hydrophobic/hydrophilic sectors on the Edmundson projection. For the K&D and Eisenberg scales, Ile and Arg are used. For α-helical peptides (projection angle=100°, an 18 residue peptide with 9 Arg, 9 Phe/Ile is used. This results in μHmax of 6.3, 2.8 and 0.83 for the CCS, K&D and Eisenberg scales, respectively. Table 1 provides the hydrophobicity values for the various amino acid residues using the various hydrophobicity scales.

TABLE 1

HYDROPHOBICITY SCALES

| Residue | Symbol | CCS | Kyte-Doolittle | Eisenberg |
|---------|--------|-----|----------------|-----------|
|         |        | Hi  | Hi             | Hi        |
| Ile     | I      | 8.7 | 4.5            | 0.73      |
| Leu     | L      | 9.7 | 3.8            | 0.53      |
| Trp     | W      | 9.7 | −0.9           | 0.37      |
| Phe     | F      | 10.0| 2.8            | 0.61      |
| Val     | V      | 4.1 | 4.2            | 0.54      |
| Met     | M      | 4.6 | 1.9            | 0.26      |
| Tyr     | Y      | 2.5 | −1.3           | 0.02      |
| Ala     | A      | −1.1| 1.8            | 0.25      |
| Pro     | P      | −0.2| −1.6           | −0.07     |
| Thr     | T      | −3.8| −0.7           | −0.18     |
| Ser     | S      | −4.3| −0.8           | −0.26     |
| Cys     | C      | −2.3| 2.5            | 0.04      |
| Gly     | G      | −2.4| −0.4           | 0.16      |
| Asn     | N      | −7.1| −3.5           | −0.64     |
| Asp     | D      | −8.3| −3.5           | −0.72     |
| Gln     | Q      | −6.0| −3.5           | −0.69     |
| Glu     | E      | −8.3| −3.5           | −0.62     |
| His     | H      | −3.8| −3.2           | −0.40     |
| Lys     | K      | −9.9| −3.9           | −1.10     |
| Arg     | R      | −10 | −4.5           | −1.80     |
| Nle     | Z      | 9.1 | norleucine     | —         |
| Deg     | 1      | 13.7| dipropylglycine| —         |
| Deg     | 2      | 6.0 | diethylglycine | —         |
| Nva     | 3      | 5.3 | norvaline      | —         |
| Aib     | B      | 1.1 | aminoisobutyric acid | —   |
| Abu     | U      | 1.7 | aminobutyric acid | —      |
| Orn     | O      | −9  | ornithine      | —         |
| Hse     | 5      | −3.5| homoserine     | —         |
| Dap     | 5      | −9.5| diaminopropionic acid | —  |
| Dab     | 6      | −9.3| diaminobutyric acid | —    |
| Acp     | 5      | 6.2 | aminocyclopentanoic acid | — |

Peptide analysis tool programs (including programs available on the internal can be used to calculate hydrophobic moment of amphipathic sequences. See, for instance, the peptide sequence analysis tool created by Alex Tossi and Luca Sandri available on the World Wide Web (www) at bbcm.univ.trieste.it/~tossi/HydroCalc/HydroMCalc.html (maintained by the University of Trieste, Italy). This tool is also discussed in Tossi et al. ("New Consensus hydrophobicity scale extended to non-proteinogenic amino acids", PEPTIDES 2002, *Proc. of 27th European Peptide Symposium*, Sorrento, 2002), incorporated herein by reference. In particular, this tool utilizes a Java applet that calculates the mean hydrophobicity, the mean hydrophobic moment and the relative hydrophobic moment for peptides using a selected scale and a selected projection angle; this program is known as HydroMCalc.

Ordinary skilled artisans will recognize other ways in which hydrophobic moment and other comparative measurements of amphipathicity can be calculated.

Hydrophilic: A hydrophilic (or lipophobic) group is electrically polarized and capable of H-bonding, enabling it to dissolve more readily in water than in oil or other "non-polar" solvents.

Implant: A support device. For example, an implant is a device that is employed to enhance and support existing passages, channels, and conduits such as the lumen of a blood vessel. In an example, an implant is an endovascular support. In a particular example, an implant is a stent. In one example, an implant is effective to maintain a vessel open. In the present disclosure, an implant can be coated with or impregnated with one or more of the disclosed peptides to assist with the treatment of a dyslipidemic or vascular disorder.

Inhibiting or treating a disease: Inhibiting the full development of a disease, disorder or condition, for example, in a subject who is at risk for a disease such as atherosclerosis and cardiovascular disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated/purified: An "isolated" or "purified" biological component (such as a nucleic acid, peptide or protein) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell. Preferably, a preparation is purified such that the biological component represents at least 50%, such as at least 70%, at least 90%, at least 95%, or greater of the total biological component content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker: A molecule that joins two other molecules, either covalently, or through ionic, van der Waals or hydrogen bonds. In particular examples, a linker comprises glycine, proline or alanine. In one specific example, the linker is a sequence of one or more prolines.

Lipid: A class of water-insoluble, or partially water insoluble, oily or greasy organic substances, that are extractable from cells and tissues by nonpolar solvents, such as chloroform or ether. Types of lipids include triglycerides (i.e., natural fats and oils composed of glycerin and fatty acid chains), phospholipids (e.g., phosphatidylethanolamine, phosphatidylcholine, phosphatidylserine, and phosphatidylinositol), sphingolipids (e.g., sphingomyelin, cerebrosides and gangliosides), and sterols (e.g., cholesterol).

Lipid affinity: A measurement of the relative binding affinity of an amphipathic α-helix for lipids. Any number of methods well know to one of skill in the art can be used to determine lipid affinity. In one embodiment, the lipid affinity of an amphipathic α-helix is determined by calculating the hydrophobic moment score of the amphipathic α-helix. For example, an amphipathic α-helix with relatively high lipid affinity will have a hydrophobic moment score per residue greater than or equal to about 0.34 on the Eisenberg scale (100 degree alpha helix), while an amphipathic α-helix with relatively low lipid affinity will have a hydrophobic moment score per residue of less than about 0.34 on the Eisenberg scale (Eisenberg et al., *Faraday Symp. Chem. Soc.* 17:109-120, 1982). In an alternative embodiment, an amphipathic α-helix with relatively high lipid affinity has a hydrophobic moment score per residue of about 0.40 to about 0.60 on the Eisenberg consensus scale, while a low lipid affinity helix will have a hydrophobic moment score per residue of about 0.20 to about 0.40 on the consensus scale (Eisenberg et al., *PNAS* 81:140-144, 1984 and Eisenberg et al., *J. Mol. Biol.* 179:125-142, 1984). With any one peptide or peptide analog with multiple amphipathic α-helical domains, it is to be understood that the difference between the hydrophobic moment scores of the amphipathic α-helix with the relatively high lipid affinity and the amphipathic α-helix with the relatively low lipid affinity is at least 0.01 on the consensus scale. In some embodiments, the difference is higher than 0.01, such as 0.02, 0.05, 0.08 or 0.1.

In other embodiments, the lipid affinity of an amphipathic α-helix is determined by one or more functional tests. Specific, non-limiting examples of functional tests include: retention time on reverse phase HPLC, surface monolayer exclusion pressure (Palgunachari et al., *Arterioscler. Thromb. Vasc. Biol.* 16:328-338, 1996), binding affinity to phospholipid vesicles (Palgunachari et al., *Arterioscler. Thromb. Vasc. Biol.* 16:328-338, 1996), and DMPC vesicle solubilization (Remaley et al., *J. Lipid Res.* 44:828-836, 2003).

Further non-limiting examples of alternative methods of calculating the lipid affinity of an amphipathic α-helix include: total hydrophobic moment, total peptide hydrophobicity, total peptide hydrophobicity per residue, hydrophobicity of amino acids on the hydrophobic face, mean relative hydrophobic moment, hydrophobicity per residue of amino acids on the hydrophobic face, and calculated lipid affinity based on predicted peptide penetration into phospholipid bilayers (Palgunachari et al., *Arterioscler. Thromb. Vasc. Biol.* 16:328-338, 1996). Different types of hydrophobicity scales for amino acids also can be used for calculating hydrophobic moments of amphipathic helices, which can result in a different relative ranking of their lipid affinity (Kyte et al., *J. Mol. Biol.* 157:105-132, 1982).

Lipoprotein lipase (LPL): An enzyme that hydrolyzes lipids in lipoproteins, such as those present in chylomicrons and very low-density lipoproteins (VLDLs), into three free fatty acids and one glycerol molecule. A deficiency in lipoprotein lipase activity can lead to hypertriglyceridemia. In an example, LPL is activated (e.g., stimulated or turned-on) by an apoC-II protein, such as a fragment of an apoC-II protein including the third helix of apoC-II. For example, LPL is activated by a polypeptide that includes a domain with an amino acid sequence set forth in any of SEQ ID NOs: 63-69. LPL activation can be measured by methods known of those to skill in the art including those described in detail in Example 10. In an example, LPL activation can be determined in vivo by obtaining a sample from a subject and measuring triglyceride levels in such sample prior to and after treatment with one or more of the disclosed peptides. A peptide that increases triglyceride levels above the baseline value by more than 3 times (x's; e.g., 3×) the coefficient of variation of the assay, which for most triglycerides assays would be approximately 2-5%, is considered a peptide that inhibits LPL. Any peptide that lowers the serum triglyceride compared to the result obtained with the in vivo administration of the 5A peptide by more than 3× the coefficient of variation of triglyceride assay is considered a peptide that activates LPL. A potentially clinically useful LPL-activating peptide is a peptide that, when administered to subjects, results in a triglyceride level of less than 150 mg/dl, such as less than 145 mg/dl, 140 mg/dl, 135 mg/dl, 130 mg/dl, 125 mg/dl or 120 mg/dl.

Non-cytotoxic: A non-cytotoxic compound is one that does not substantially affect the viability or growth characteristics of a cell at a dosage normally used to treat the cell or a subject. Furthermore, the percentage of cells releasing intracellular contents, such as LDH or hemoglobin, is low (e.g., about 10% or less) in cells treated with a non-cytotoxic compound. Lipid efflux from a cell that occurs by a non-cytotoxic compound results in the removal of lipid from a cell by a process that maintains the overall integrity of the cell membrane and does not lead to significant cell toxicity.

Non-polar: A non-polar compound is one that does not have concentrations of positive or negative electric charge. Non-polar compounds, such as, for example, oil, are not well soluble in water.

Peptide: A polymer in which the monomers are amino acid residues which are joined together through amide bonds. When the amino acids are alpha-amino acids, either the L-optical isomer or the D-optical isomer can be used. The terms "peptide" or "polypeptide" as used herein are intended to encompass any amino acid sequence and include modified sequences such as glycoproteins. The term "peptide" is specifically intended to cover naturally occurring peptides, as well as those which are recombinantly or synthetically produced. The term "residue" or "amino acid residue" includes reference to an amino acid that is incorporated into a peptide, polypeptide, or protein.

Pharmaceutically acceptable carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more multi-domain peptides or peptide analogs and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phospholipid: A phospholipid consists of a water-soluble polar head, linked to two water-insoluble non-polar tails (by a negatively charged phosphate group). Both tails consist of a fatty acid, each about 14 to about 24 carbon groups long. When placed in an aqueous environment, phospholipids form a bilayer or micelle, where the hydrophobic tails line up against each other. This forms a membrane with hydrophilic heads on both sides. A phospholipid is a lipid that is a primary component of animal cell membranes.

Polar: A polar molecule is one in which the centers of positive and negative charge distribution do not converge. Polar molecules are characterized by a dipole moment, which measures their polarity, and are soluble in other polar compounds and virtually insoluble in nonpolar compounds.

Recombinant nucleic acid: A sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of the nucleic acid.

Therapeutically effective amount: A quantity of a specified agent (or combination of agents) sufficient to achieve a desired effect in a subject being treated with that agent. For example, this can be the amount of a multi-domain peptide or peptide analog useful in preventing, ameliorating, and/or treating a dyslipidemic disorder (e.g., atherosclerosis) in a subject. Ideally, a therapeutically effective amount of an agent is an amount sufficient to prevent, ameliorate, and/or treat a dyslipidemic disorder (e.g., atherosclerosis) in a subject without causing a substantial cytotoxic effect (e.g., membrane microsolubilization) in the subject. The effective amount of an agent useful for preventing, ameliorating, and/or treating a dyslipidemic disorder (e.g., atherosclerosis) in a subject will be dependent on the subject being treated, the severity of the disorder, and the manner of administration of the therapeutic composition. In an example, a therapeutically effective amount of one of the disclosed peptides (or peptide mixtures, such as a peptide including a first domain capable of promoting lipid efflux and a second domain having lipoprotein lipase activity) results in a triglyceride level of at least less than 150 mg/dl, such as less than 145 mg/dl, less than 140 mg/dl, less than 135 mg/dl, less than 130 mg/dl, less than 125 mg/dl or less than 120 mg/dl.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

III. Overview of Several Embodiments

Isolated peptides and peptide analogs with multiple amphipathic α-helical domains that promote lipid efflux from cells via an ABCA1-dependent pathway are disclosed herein. In one embodiment, the multi-domain peptides include multiple amphipathic α-helical domains, wherein a first amphipathic α-helical domain exhibits higher lipid affinity compared to a second amphipathic α-helical domain (as measured, e.g., by their hydrophobic moments; see Eisenberg et al., *Faraday Symp. Chem. Soc.* 17:109-120, 1982; Eisenberg et al., *PNAS* 81:140-144, 1984; and Eisenberg et al., *J. Mol. Biol.* 179:125-142, 1984), and wherein the peptide or peptide analog promotes lipid efflux from cells by an ABCA1-dependent pathway.

In specific, non-limiting examples, the first amphipathic α-helical domain has a hydrophobic moment score (Eisenberg scale; 100 degree-alpha helix) per residue of about 0.3 to about 0.60 and the second amphipathic α-helical domain has a hydrophobic moment score per residue of about 0.1 to about 0.33, wherein the difference between the hydrophobic moment scores of the first amphipathic α-helix and the second amphipathic α-helix is at least 0.01. In some embodiments, the difference is higher than 0.01, such as 0.02, 0.05, 0.08 or 0.1. For example, the 5A peptide (SEQ ID NO: 3) has a hydrophobic moment score (Eisenberg scale; 100 degree-alpha helix) per reside of 0.34 for the N-terminal lipid affinity helix and a hydrophobic moment score per residue of 0.28 for the C-terminal low lipid affinity helix. Using an alternative scale calculation, the 5A peptide (SEQ ID NO: 3) has a hydrophobic moment score 0.4905 for the N-terminal high lipid affinity helix and a hydrophobic moment score per residue of 0.3825 for the C-terminal low lipid affinity helix. Optionally, the order of relatively high and relatively low amphipathic helices can be reversed in the peptide.

Using a relative mean hydrophobic moment score, which is normalized to a "perfect" amphipathic helix with a maximum score of 0.83, the two helices of the 5A peptide (SEQ ID NO: 3) have values of 0.42 and 0.34. It is well recognized that different physical properties, however, can be used for determining the hydrophobicity of amino acids, which results in different scales for calculating the hydrophobic moment of peptides. Calculations with these different scales can change the absolute value of the hydrophobicity scores and the relative ranking of the lipid affinity of amphipathic helices. For example, using the Kyte & Doolittle scale (Kyte et al., *J. Mol. Biol.* 157:105-132, 1982), the N-terminal and C-terminal helices of the 5A peptide would be seen to have hydrophobic moment scores of 1.47 and 1.26, with a relative mean hydrophobic moment scores of 0.51 and 0.44 (perfect helix: 2.8). Using a combined consensus scale, which is a hybrid of several different scoring systems, the N-terminal and C-terminal helices of the 5A peptide would have hydrophobic moment scores of 4.01 and 2.02, with a relative mean hydrophobic moment score of 0.64 an 0.32 (perfect helix: 6.3). All such scales, calculations, and measurements can be used, converted and interchanged, as recognized by those of ordinary skill in the art.

Other representative non-limiting example peptides with multiple amphipathic α-helical domains are shown in SEQ ID NOs: 4-45.

Optionally, the isolated peptides and peptide analogs that promote ABCA1-dependent lipid efflux from cells are also substantially non-cytotoxic, for instance, do not significantly increase triglycerides (e.g., triglyceride levels less than 150 mg/dl or do not show a statically significant increase above baseline triglycerides values. Disclosed herein are also isolated peptides and peptide analogs (or combinations of peptides or analogs, which are not necessarily covalently linked one to another) capable of promoting lipid efflux from cells by an ABCA1-dependent pathway and activating lipoprotein lipase. In one embodiment, the isolated peptides and peptide analogs (or mixtures) include a first domain that promotes lipid efflux and a second domain that activates lipoprotein lipase; optionally, these domains are covalently linked, with or without the presence of a linking peptide or other bridging molecule.

In specific non-limiting examples, the first domain is an amphipathic α-helical domain with a hydrophobic moment score (Eisenberg scale; 100 degree-alpha helix) per residue of about 0.34 to about 0.60 and the second domain is an amphipathic α-helical domain of apoC-II protein or a variant or fragment thereof that retains a lipoprotein lipase-activating property, such as a domain comprising an amino acid sequence set forth in any one of SEQ ID NOs: 63-69. Representative non-limiting example peptides with both lipid efflux promoting activity and lipoprotein lipase activating activity are shown in SEQ ID NOs: 70-75. In one example, a peptide has the amino acid sequence set forth in SEQ ID NO: 70. LPL activation can be measured by methods known of those to skill in the art including those described in detail in Example 10. In an example, LPL activation can be determined in vivo by obtaining a sample from a subject and measuring triglyceride levels in such sample prior to and after treatment with one or more of the disclosed peptides. A triglyceride level of less than 150 mg/dl following treatment of a subject (such as a human subject) with a test compound indicates that the compound (e.g., apoC-II protein, fragment or variant thereof) is a LPL activator.

The isolated peptides and peptide analogs disclosed herein can also include an additional functional domain or peptide. Specific, non-limiting examples of the additional functional domains or peptides include a heparin binding site, an integrin binding site, a P-selectin site, a TAT HIV sequence, a panning sequence, a penatratin sequence, a SAA C-terminus sequence, a SAA N-terminus sequence, a LDL receptor sequence, a modified 18A sequence, an apoA-I Milano sequence, a 6x-His sequence, a lactoferrin sequence, a lipoprotein lipase activating domain (such as a fragment or variant of apoC-II) or combinations of two or more thereof.

Pharmaceutical compositions are disclosed that include one or more isolated peptides or peptide analogs with multiple amphipathic α-helical domains that promote lipid efflux from cells via an ABCA1-dependent pathway. Representative peptides with multiple amphipathic α-helical domains are shown in SEQ ID NOs: 3-45. Pharmaceutical compositions are also disclosed that include one or more isolated peptides or peptide analogs that promote lipid efflux from cells via an ABCA1-dependent pathway and activate lipoprotein lipase, such as representative peptides shown in SEQ ID NOs: 70-75. In one specific example, the pharmaceutical composition includes a peptide with the amino acid sequence of SEQ ID NO: 70.

Methods are provided for treating or inhibiting dyslipidemic and vascular disorders in a subject. In one embodiment, this method includes administering to the subject a therapeutically effective amount of a pharmaceutical composition that includes one or more isolated peptides or peptide analogs with two or more amphipathic α-helical domains that promote lipid efflux from cells via an ABCA1-dependent pathway and activate lipoprotein lipase. In specific, non-limiting examples, the dyslipidemic and vascular disorders include hyperlipidemia, hyperlipoproteinemia, hypercholesterolemia, hypertriglyceridemia, HDL deficiency, apoA-I deficiency, coronary artery disease, atherosclerosis, thrombotic stroke, peripheral vascular disease, restenosis, acute coronary syndrome, and reperfusion myocardial injury.

In certain examples of the provided method, the isolated peptide includes two amphipathic α-helical domains in which the first domain has lipid efflux promoting activity and the second domain has lipoprotein lipase activity (such as an apoC-II protein, fragment or variant with an amino acid sequence as set forth in SEQ ID NOs: 63-69). In one example, the isolated peptide includes the amino sequence of SEQ ID NO: 70. In other examples of the provided method, the isolated peptide includes two or more amphipathic α-helical domain capable of promoting lipid efflux with an apoC-II variant or fragment (such as provided in SEQ ID NO: 69) attached to the C-terminal end of at least one of the lipid efflux promoting amphipathic α-helical domains.

In other non-limiting examples of the provided method, the method includes administering to the subject a therapeutically effective amount of a pharmaceutical composition that includes at least one isolated peptide (or peptide analog) with multiple amphipathic α-helical domains and that promotes lipid efflux from cells via an ABCA1-dependent pathway (such as an isolated peptide that includes two amphipathic α-helical domains and has an amino acid sequence as set forth in SEQ ID NOs: 3-45) and a separate lipoprotein lipase activating agent, such as an apoC-II protein, variant or fragment thereof (e.g., peptide) that retains lipoprotein lipase activity (e.g., results in triglyceride levels of less than 150 mg/dl). The peptide that promotes efflux need not be covalently linked to the peptide that has LPL activating activity.

Methods for identifying non-cytotoxic peptides that promote ABCA1-dependent lipid efflux from cells and/or peptides that activate lipoprotein lipase in cells (or peptides that have both activities) are also disclosed.

IV. Multi-Domain Amphipathic Peptides

Isolated peptides and peptide analogs including peptides with multiple amphipathic α-helical domains that promote lipid efflux from cells via an ABCA1-dependent pathway have been identified and are described in, for instance, PCT Publication No. WO 2006/044596 (PCT/US2005/036933), as well as the corresponding U.S. National Stage application (U.S. patent application Ser. No. 11/577,259), which are incorporated herein by reference in their entirety. Various peptides described therein included a first amphipathic α-helical domain exhibited higher lipid affinity relative to a second amphipathic α-helical domain, in the same peptide.

ApoA-I, the predominant protein constituent of HDL (Panagotopulos et al., *J. Biol. Chem.* 277:39477-39484, 2002), is believed to promote lipid efflux from cells by a detergent-like extraction process (Remaley et al., *J. Lipid Res.* 44:828-836, 2003). The ABCA1 transporter has been proposed to facilitate this process by creating a lipid microdomain that promotes the binding of apoA-I to cells and creates a lipid domain that is susceptible for removal by apoA-I by a detergent-like extraction process. ApoA-I, like most of the other natural exchangeable type apolipoproteins, is almost completely dependent upon the presence of ABCA1 for promoting lipid efflux (Remaley et al., *Biochem. Biophys. Res. Commun.* 280:818-823, 2001). Furthermore, when lipid efflux occurs by apoA-I and the other natural exchangeable type apolipoproteins, it occurs by a non-cytotoxic process, whereby the integrity of the cell membrane is maintained (Remaley et al., *J. Lipid Res.* 44:828-836, 2003). ApoA-I contains at least 8 large amphipathic helical domains, which have a wide range of lipid affinity (Gillote et al., *J. Biol. Chem.* 274:2021-2028, 1999).

Synthetic peptides of each helix of apoA-I have been made, and it has been shown that only 2 of the 8 large amphipathic helices of apoA-I, which have relatively high lipid affinity, can by themselves promote lipid efflux from cells in culture (Gillote et al., *J. Biol. Chem.* 274:2021-2028, 1999 and Palgunachari et al., *Arterioscler. Thromb. Vasc. Biol.* 16:328-338, 1996). Additionally, synthetic peptide mimics of apolipoproteins have been shown to have anti-inflammatory and anti-oxidant properties (Van Lenten et al., *Trends Cardiovasc. Med.* 11:155-161, 2001; Navab et al., *Cur. Opin. Lipidol.* 9:449-456, 1998; Barter et al., *Cur. Opin. Lipidol.* 13:285-288, 2002).

Previously, synthetic peptide mimics of apolipoproteins have been designed to have high lipid affinity (Remaley et al., *J. Lipid Res.* 44:828-836, 2003; Segrest et al., *J. Lipid Res.* 33:141-166, 1992; Anantharamaiah et al., *J. Biol. Chem.* 260: 10248-10255, 1985; Garber et al, *J. Lipid Res.* 42:545-552, 2001; Navab et al., *Circulation* 105:290-292, 2002; and U.S. Pat. No. 6,156,727), because high lipid affinity has been shown to be a necessary feature for a peptide to mediate lipid efflux by the ABCA1 transporter (Remaley et al., *J. Lipid Res.* 44:828-836, 2003). It has also been shown, however, that peptide mimics of apoA-I with high lipid affinity can also promote lipid efflux independent of the ABCA1 transporter (Remaley et al., *J. Lipid Res.* 44:828-836, 2003). Such peptides have been shown to promote lipid efflux from cells not expressing the ABCA1 transporter, and from Tangier disease cells that do not contain a functional ABCA1 transporter (Remaley et al., *J. Lipid Res.* 44:828-836, 2003). Furthermore, synthetic peptide mimics of apoA-I that posses high lipid affinity can also extract lipid by a passive physical process, based on their ability to remove lipid from cells that have been fixed with paraformaldehyde (Remaley et al., *J. Lipid Res.* 44:828-836, 2003). Lipid efflux from cells by this ABCA1-independent pathway has been shown to be cytotoxic to cells, based on the cellular release of LDH (Remaley et al., *J. Lipid Res.* 44:828-836, 2003).

In addition to the undesirable cytotoxic effect on cells, ABCA1-independent lipid efflux may also reduce the therapeutic benefit of such peptides by reducing their in vivo capacity for removing lipid from cells affected by the atherosclerotic process. For example, even in subjects with dyslipidemic and vascular disorders, most cells do not have excess cellular cholesterol and, therefore, do not express the ABCA1 transporter. Cells, such as macrophages, endothelial cells and smooth muscle cells, which are present in atherosclerotic plaques, are all prone to lipid accumulation, and express ABCA1 when loaded with excess cholesterol. The expression of ABCA1 by these cells has been shown to be exquisitely regulated by the cholesterol content of cells (Langmann et al., *Biochem. Biophys. Res. Commun.* 257:29-33, 1999). Induction of the ABCA1 transporter by intracellular cholesterol is a protective cellular mechanism against excess intracellular cholesterol and has been shown to be critical in preventing the development of atherosclerosis (Dean and Chimini, *J. Lipid Res.* 42:1007-1017, 2001). Peptide mimics of apolipoproteins that are not specific for removing cholesterol by the ABCA1 transporter would be less therapeutically effective in removing cholesterol from ABCA1 expressing cells because any cholesterol removed by the peptides from the more abundant non-ABCA1 expressing cells will reduce the overall total cholesterol binding capacity of these peptides. The selective and non-cytotoxic removal of lipid from only cells that express the ABCA1 transporter would, therefore, be a desirable property for therapeutic peptide mimics of apolipoproteins.

The current disclosure provides isolated multi-domain peptides or peptide analogs that specifically efflux lipids from cells by the ABCA1 transporter in a non-cytotoxic manner. In one embodiment, such peptides or peptide analogs contain an amphipathic α-helical domain that exhibits relatively high lipid affinity (e.g., a hydrophobic moment score (Eisenberg scale; 100 degree-alpha helix) per residue of about 0.3 to about 0.60) and a second amphipathic α-helical domain with relatively low lipid affinity (e.g., a hydrophobic moment score per residue of about 0.1 to about 0.33), wherein the difference between the hydrophobic moment scores of the amphipathic α-helix with the relatively high lipid affinity and the amphipathic α-helix with the relatively low lipid affinity is at least 0.01. In some embodiments, the difference is higher than 0.01, such as 0.02, 0.05, 0.08 or 0.10.

Peptides containing one amphipathic α-helix with a relatively high lipid affinity, when coupled to another α-helix with a relatively low lipid affinity, are specific for removing lipids from cells by the ABCA1 transporter. In particular examples, these peptides are not only specific for removing lipids from cells by the ABCA1 transporter, but are also capable of activating lipoprotein lipase.

The degree of amphipathicity (i.e., degree of asymmetry of hydrophobicity) in the multi-domain peptides or peptide analogs can be conveniently quantified by calculating the hydrophobic moment ($\mu_H$) of each of the amphipathic α-helical domains. Methods for calculating $\mu_H$ for a particular peptide sequence are well-known in the art, and are described, for example in Eisenberg et al., *Faraday Symp. Chem. Soc.* 17:109-120, 1982; Eisenberg et al., *PNAS* 81:140-144, 1984; and Eisenberg et al., *J. Mol. Biol.* 179:125-142, 1984. The actual $\mu_H$ obtained for a particular peptide sequence will depend on the total number of amino acid residues composing the peptide. The amphipathicities of peptides of different lengths can be directly compared by way of the mean hydrophobic moment. The mean hydrophobic moment per residue can be obtained by dividing $\mu_H$ by the number of residues in the peptide.

In another embodiment, such peptides or peptide analogs contain an amphipathic α-helical domain that exhibits relatively high lipid affinity (e.g., a hydrophobic moment score (Eisenberg scale; 100 degree-alpha helix) per residue of about 0.30 to about 0.60) and a second amphipathic α-helical domain with moderate lipid affinity (e.g., a hydrophobic moment score (Eisenberg scale; 100 degree-alpha helix) per residue of about 0.29 to about 0.33), wherein the difference between the hydrophobic moment scores of the amphipathic α-helix with the relatively high lipid affinity and the amphipathic α-helix with the relatively moderate lipid affinity is at least 0.01. In some embodiments, the difference is higher than 0.01, such as 0.02, 0.05, 0.08 or 0.1. Such peptides have reduced specificity for the ABCA1 transporter, as compared to peptides containing one amphipathic α-helix with a relatively high lipid affinity and one amphipathic α-helix with a relatively low lipid affinity, but are still less cytotoxic to cells than peptides that contain two amphipathic α-helical domains with relatively high lipid affinity.

Specific, non-limiting examples of multi-domain peptides with multiple amphipathic α-helical domains that mediate ABCA1-dependent cholesterol efflux from cells are shown in Table 2.

TABLE 2

Exemplary multi-domain peptides that mediate ABCA1-dependent cholesterol efflux from cells.

| Peptide | Sequence | SEQ ID NO: |
|---|---|---|
| 5A-37pA | DWLKAFYDKVAEKLKEAFPDWAKAAYDKAAEKAKEAA | 3 |
| 1A-37pA | DWLKAFYDKVAEKLKEAFPDWLKAFYDKVAEKAKEAF | 4 |
| 2A-37pA | DWLKAFYDKVAEKLKEAFPDWLKAFYDKVAEKAKEAA | 5 |
| 3A-37pA | DWLKAFYDKVAEKLKEAFPDWLKAAYDKVAEKAKEAA | 6 |
| 4A-37pA | DWLKAFYDKVAEKLKEAFPDWLKAAYDKAAEKAKEAA | 7 |
| Pep1 | DWLKAFYDKVAEKLKEAFPDWGKAGYDKGAEKGKEAG | 8 |
| Pep2 | DWLKAFYDKVAEKLKEAFPDWGKAGYDKGAEKGKEAF | 9 |
| Pep3 | DWGKAGYDKGAEKGKEAGDWLKAFYDKVAEKLKEAF | 10 |
| Pep4 | DWLKAFYDKVAEKLKEAFPDWLKAFYDKVAEKLK | 11 |
| Pep5 | KAFYDKVAEKLKEAFPDWLKAFYDKVAEKLKEAF | 12 |
| Pep6 | DWLKAFYDKVAEKLKEAFPDWLKAFYDKVA | 13 |
| Pep7 | DKVAEKLKEAFPDWLKAFYDKVAEKLKEAF | 14 |
| Pep8 | DWLKAFYDKVAEKLKEAFPDWLKAFYKVAEKLKEAF | 15 |
| Pep9 | DWLKAFYDKVAEKLKEAFPDWLKAFYVAEKLKEAF | 16 |
| Pep10 | DWLAFYDKVAEKLKEAFPDWLKAFYDKVAEKLKEAF | 17 |
| Pep11 | DWLFYDKVAEKLKEAFPDWLKAFYDKVAEKLKEAF | 18 |
| Pep12 | DWLKAFYDKVAEKLKEAFPDWLAKAFYDKVAEKLKEAF | 19 |
| Pep13 | DWLKAFYDKVAEKLKEAFPDWLAAKAFYDKVAEKLKEAF | 20 |
| Pep14 | DWLKAAFYDKVAEKLKEAFPDWLKAFYDKVAEKLKEAF | 21 |
| Pep15 | DWLKAAAFYDKVAEKLKEAFPDWLKAFYDKVAEKLKEAF | 22 |
| Pep16 | DWLKAFYDKVAEKLKEAFPDWLEAFYDKVAKKLKEAF | 23 |
| Pep17 | DWLKAFYDKVAEKLKEAFPDWLEAFYDEVAKKLKKAF | 24 |
| Pep18 | DWLEAFYDKVAKKLKEAFPDWLKAFYDKVAEKLKEAF | 25 |
| Pep19 | DWLEAFYDEVAKKLKKAFPDWLKAFYDKVAEKLKEAF | 26 |
| Pep20 | DWLKAFYDKVAEKLKEAFPDWLKAFYDKVAEKLKEAF | 27 |
| Pep21 | DWLKAFYDKVAEKLKEAFPDWLKAFYDKVAEKLKEAF | 28 |
| Pep22 | DWLKAFYDKVAEKLKEAFPDWLKAFYDKVAEKLKEAF | 29 |
| Pep23 | DWLKAFYDKVAEKLKEAFPDWLKAFYDKVAEKLKEAF | 30 |
| Pep24 | LLDNWDSVTSTFSKLREQPDWAKAAYDKAAEKAKEAA | 31 |
| Pep25 | LESFKVSFLSALEEYTKKPDWAKAAYDKAAEKAKEAA | 32 |
| Pep26 | DWAKAAYDKAAEKAKEAAPLLDNWDSVTSTFSKLREQ | 33 |
| Pep27 | DWAKAAYDKAAEKAKEAAPLESFKVSFLSALEEYTKK | 34 |
| Pep28 | DWLKAFYDKVAEKLKEAFPSDELRQRLAARLEALKEN | 35 |
| Pep29 | DWLKAFYDKVAEKLKEAFPRAELQEGARQKLHELQEK | 36 |
| Pep30 | SDELRQRLAARLEALKENPDWLKAFYDKVAEKLKEAF | 37 |
| Pep31 | RAELQEGARQKLHELQEKPDWLKAFYDKVAEKLKEAF | 38 |
| Pep32 | LLDNWDSVTSTFSKLREQPSDELRQRLAARLEALKEN | 39 |
| Pep33 | LESFKVSFLSALEEYTKKPRAELQEGARQKLHELQEK | 40 |
| Pep34 | SDELRQRLAARLEALKENPLLDNWDSVTSTFSKLREQ | 41 |
| Pep35 | LLDNWDSVTSTFSKLREQPLESFKVSFLSALEEYTKK | 42 |
| Pep36 | DWLKAFYDKVAEKLKEAFPDWLRAFYDKVAEKLKEAF | 43 |
| Pep37 | DWLKAFYDKVAEKLKEAFPDWLRAFYDRVAEKLKEAF | 44 |
| Pep38 | DWLKAFYDKVAEKLKEAFPDWLRAFYDRVAEKLREAF | 45 |

Specific, non-limiting examples of α-helical domains capable of activating lipoprotein lipase are shown in Table 3.

TABLE 3

Exemplary domains that activate lipoprotein lipase in cells.

| Domain | Sequence | SEQ ID NO: |
|---|---|---|
| apoC-II (residue 51-79) | DLYSKSTAAMSTYTGIFTDQVLSVLKGEE | 63 |
| apoC-II (residue 56-79) | STAAMSTYTGIFTDQVLSVLKGEE | 64 |
| apoC-II (residue 59-79) | AMSTYTGIFTDQVLSVLKGEE | 65 |
| apoC-II (residue 61-79) | STYTGIFTDQVLSVLKGEE | 66 |
| Consensus apoC-II (residue 61-79) | xxYxxIxxDQxxxxxxxxx; wherein x is any amino acid that will form an amphipathic helix, will conserve the relative position of these 4 residues with respect to their position in a helical wheel plot and allow the domain to activate lipoprotein lipase. | 67 |
| Consensus apoC-II (residue 59-79) | AxxTYxGIxxDQVLSVLKGEE; wherein x is any amino acid that will form an amphipathic helix, will conserve the relative position of these 4 residues with respect to their position in a helical wheel plot and allow the domain to activate lipoprotein lipase. | 68 |

Specific, non-limiting examples of multi-domain peptides with multiple amphipathic α-helical domains capable of mediating ABCA1-dependent cholesterol efflux from cells and activating lipoprotein lipase are shown in Table 4.

TABLE 4

Exemplary multi-domain peptides that mediate ABCA1-dependent cholesterol efflux from cells and are capable of activating lipoprotein lipase.

| Peptide | Sequence | SEQ ID NO: |
|---|---|---|
| 5A-P-apoC-II (residue 51-79); Referred to as 18A-C-II | DWLKAFYDKVAEKLKEAFPDLYSKSTAAMSTYTGIFTDQVLSVLKGEE (using DLYSKSTAAMSTYTGIFTDQVLSVLKGEE-mean hydrophobic moment: CCS scale: 1.86 µH; Kyte & Doolittle: 0.41 µH; and Eisenberg: 0.17 µH; mean hydrophobicity: CCS scale: -1.13 H; Kyte & Doolittle: -0.36 H; Eisenberg: -0.12 H; mean relative hydrophobic moment: CCS scale: 0.29 µHrel; Kyte & Doolittle: 0.14 µHrel; Eisenberg: 0.21 µHrel) | 70 |
| 5A-P-apoC-II (residue 56-79) | DWLKAFYDKVAEKLKEAFPSTAAMSTYTGIFTDQVLSVLKGEE (using STAAMSTYTGIETDQVLSVLKGEE-mean hydrophobic moment: CCS scale: 1.3 µH; Kyte & Doolittle: 0.21 µH; Eisenberg: 0.12 µH; mean hydrophobicity: CCS scale: -0.94 H; Kyte & Doolittle:-0.18 H; Eisenberg: -0.05 H; mean relative hydrophobic moment: CCS scale: 0.2 µHrel; Kyte & Doolittle: 0.07 µHrel; Eisenberg: 0.15 µHrel) | 71 |
| 5A-P-apoC-II (residue 59-79) | DWLKAFYDKVAEKLKEAFPAMSTYTGIFTDQVLSVLKGEE (using AMSTYTGIFTDQVLSVLKGEE-mean hydrophobic moment: CCS scale: 1.66 µH; Kyte & Doolittle: 0.37 µH; Eisenberg: 0.16 µH; mean hydrophobicity: CCS scale: -0.63 H; Kyte & Doolittle: -0.22 H; Eisenberg: -0.05 H; mean relative hydrophobic moment: CCS scale: 0.26 µHrel; Kyte & Doolittle: 0.12 µHrel; Eisenberg: 0.2 µHrel) | 72 |
| 5A-P-apoC-II (residue 61-79) | DWLKAFYDKVAEKLKEAFPSTYTGIFTDQVLSVLKGEE (using STYTGIFTDQVLSVLKGEE-mean hydrophobic moment: CCS scale: 1.61 µH; Kyte & Doolittle: 0.31 µH; Eisenberg: 0.16 µH; mean hydrophobicity: CCS scale: -0.88 H; Kyte & Doolittle: -0.43 H; Eisenberg: -0.08 H; mean relative hydrophobic moment: CCS scale: 0.25 µHrel; Kyte & Doolittle: 0.11 µHrel; Eisenberg: 0.2 µHrel) | 73 |
| 5A-P-apoC-II (residue 61-79) | DWLKAFYDKVAEKLKEAFPxxYxxIxxDQxxxxxxxxx | 74 |
| 5A-apoC-II (residue 59-79) | DWLKAFYDKVAEKLKEAFPAxxTYxGIxxDQVLSVLKGEE | 75 |

In the multi-domain peptides disclosed herein, the linkage between amino acid residues can be a peptide bond or amide linkage (i.e., —C—C(O)NH—). Alternatively, one or more amide linkages are optionally replaced with a linkage other than amide, for example, a substituted amide. Substituted amides generally include, but are not limited to, groups of the formula —C(O)NR—, where R is ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, ($C_5$-$C_{20}$) aryl, substituted ($C_5$-$C_{20}$) aryl, ($C_6$-$C_{26}$)alkaryl, substituted ($C_6$-$C_{26}$)alkaryl, 5-20 membered heteroaryl, substituted 5-20 membered heteroaryl, 6-26 membered alkheteroaryl, and substituted 6-26 membered alkheteroaryl. Additionally, one or more amide linkages can be replaced with peptidomimetic or amide mimetic moieties which do not significantly interfere with the structure or activity of the peptides. Suitable amide mimetic moieties are described, for example, in Olson et al., *J. Med. Chem.* 36:3039-3049, 1993.

Additionally, in representative multi-domain peptides disclosed herein, the amino- and carboxy-terminal ends can be modified by conjugation with various functional groups. Neutralization of the terminal charge of synthetic peptide mimics of apolipoproteins has been shown to increase their lipid affinity (Yancey et al., *Biochem.* 34:7955-7965, 1995; Venkatachalapathi et al., *Protein: Structure, Function and Genetics* 15:349-359, 1993). For example, acetylation of the amino terminal end of amphipathic peptides increases the lipid affinity of the peptide (Mishra et al., *J. Biol. Chem.* 269:7185-7191, 1994). Other possible end modifications are described, for example, in Brouillette et al., *Biochem. Biophys. Acta* 1256:103-129, 1995: Mishra et al., *J. Biol. Chem.* 269:7185-7191, 1994; and Mishra et al., *J. Biol. Chem.* 270: 1602-1611, 1995.

Furthermore, in representative multi-domain peptides disclosed herein, the amino acid proline is used to link the multiple amphipathic α-helices. However, other suitable amino acids (such as glycine, serine, threonine, and alanine) that functionally separate the multiple amphipathic α-helical domains can be used. In some embodiments, the linking amino acid will have the ability to impart a β-turn at the linkage, such as glycine, serine, threonine, and alanine. In addition, larger linkers containing two or more amino acids or bifunctional organic compounds, such as $H_2N(CH_2)_nCOOH$, where n is an integer from 1 to 12, can also be used. Examples of such linkers, as well as methods of making such linkers and peptides incorporating such linkers, are well-known in the art (see, e.g., Hunig et al., *Chem. Ber.* 100:3039-3044, 1974 and Basak et al., *Bioconjug. Chem.* 5:301-305, 1994).

Also encompassed by the present disclosure are modified forms of the multi-domain peptides, wherein one or more amino acids in the peptides are substituted with another amino acid residue. The simplest modifications involve the substitution of one or more amino acids for amino acids having similar physiochemical and/or structural properties. These so-called conservative substitutions are likely to have minimal impact on the activity and/or structure of the resultant peptide. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the peptide backbone in the area of the substitution, for example, as a helical conformation, (b) the charge or hydrophobicity of the molecule at the target site, or (c) the bulk of the side chain.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having non-polar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Additional amino acids that are classified in each of the above groups are known to those of ordinary skill in the art.

The substitutions which in general are expected to produce the greatest changes in peptide properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

As the lipid affinity of an amphipathic helix is largely due to the hydrophobicity of the amino acid residues on the hydrophobic face of the helix (Eisenberg et al., *PNAS* 81:140-144, 1984 and Eisenberg et al., *J. Mol. Biol.* 179:125-142, 1984), the overall lipid affinity of an amphipathic helix can be reduced by replacing hydrophobic amino acids with more polar amino acids. In one embodiment, hydrophobic amino acids on the hydrophobic face of the 37-pA peptide (e.g., Phe, Leu or Val) were replaced with Ala, which is less hydrophobic than Phe, Leu and Val (Eisenberg et al., *PNAS* 81:140-144, 1984 and Eisenberg et al., *J. Mol. Biol.* 179:125-142, 1984). Specific, non-limiting examples include the 5A-37pA peptide (SEQ ID NO: 3), the 1A-37pA peptide (SEQ ID NO: 4), the 2A-37pA peptide (SEQ ID NO: 5), the 3A-37pA peptide (SEQ ID NO: 6), and the 4A-37pA peptide (SEQ ID NO: 7).

In another embodiment, hydrophobic amino acids on the hydrophobic face of the 37-pA peptide (e.g., Phe, Leu or Val) can be replaced with Gly, which is less hydrophobic than Phe, Leu and Val (Eisenberg et al., *PNAS* 81:140-144, 1984 and Eisenberg et al., *J. Mol. Biol.* 179:125-142, 1984). Specific, non-limiting examples include those peptides shown in SEQ ID NOs: 8-10. Other slightly hydrophobic amino acids can be used in place of Ala or Gly for the substitutions (Eisenberg et al., *PNAS* 81:140-144, 1984 and Eisenberg et al., *J. Mol. Biol.* 179:125-142, 1984).

In addition to the naturally occurring genetically encoded amino acids, amino acid residues in the multi-domain peptides may be substituted with naturally occurring non-encoded amino acids and synthetic amino acids. Certain commonly encountered amino acids which provide useful substitutions include, but are not limited to, β-alanine and other omega-amino acids, such as 3-aminopropionic acid, 2,3-diaminopropionic acid, 4-aminobutyric acid and the like; α-aminoisobutyric acid; ε-aminohexanoic acid; δ-aminovaleric acid; N-methylglycine or sarcosine; ornithine; citrulline; t-butylalanine; t-butylglycine; N-methylisoleucine; phenylglycine; cyclohexylalanine; norleucine; naphthylalanine; 4-chlorophenylalanine; 2-fluorophenylalanine; 3-fluorophenylalanine; 4-fluorophenylalanine; penicillamine; 1,2,3,4-tetrahydroisoquinoline-3-carboxylic acid; β-2-thienylalanine; methionine sulfoxide; homoarginine; N-acetyl lysine; 2,4-diaminobutyric acid; 2,3-diaminobutyric acid; p-aminophenylalanine; N-methyl valine; homocysteine; homophenylalanine; homoserine; hydroxyproline; homoproline; N-methylated amino acids; and peptoids (N-substituted glycines).

While in certain embodiments, the amino acids of the multi-domain peptides will be substituted with L-amino acids, the substitutions are not limited to L-amino acids. Thus, also encompassed by the present disclosure are modified forms of the multi-domain peptides, wherein an L-amino acid is replaced with an identical D-amino acid (e.g., L-Arg→D-Arg) or with a conservatively-substituted D-amino acid (e.g., L-Arg→D-Lys), and vice versa. Specific, non-limiting examples include those peptides shown in SEQ ID NOs: 27-30 (see Table 2; substituted amino acids are underlined).

In addition to making amino acid substitutions, other methods can be used to reduce the lipid affinity of an amphipathic α-helical domain. Examples of such methods include shortening the helical domain (specific, non-limiting examples include those peptides shown in SEQ ID NOs: 11-14), adding or deleting one or more amino acids to change the helix's phase (specific, non-limiting examples include those peptides shown in SEQ ID NOs: 19-22 and 15-18, respectively), and changing the Type A amphipathic helical charge distribution of the polar face by switching the location of the positive and negative charge residues (specific, non-limiting examples include those peptides shown in SEQ ID NOs: 23-26; Segrest et al., *Adv. Protein Chem.* 45:303-369, 1994). Additional methods include, for example, combining natural high lipid affinity helices with artificially designed low lipid affinity helices (specific, non-limiting examples include those peptides shown in SEQ ID NOs: 31-34), combining natural low lipid affinity helices with artificially designed high lipid affinity helices (specific, non-limiting examples include those peptides shown in SEQ ID NOs: 35-38), and combining non-contiguous natural low lipid affinity helices with natural high lipid affinity helices (specific, non-limiting examples include those peptides shown in SEQ ID NOs: 39-42). Replacing Lys residues at the interface between the hydrophobic and hydrophilic face with Arg (which decreases the ability of amphipathic peptides to insert in phospholipid bilayers, Palgunachari et al., *Arterioscler. Thromb. Vasc. Biol.* 16:328-338, 1996), is an additional method of reducing the lipid affinity of an amphipathic α-helical domain (specific, non-limiting examples include those peptides shown in SEQ ID NOs: 43-45).

Many of these changes to the amphipathic helix will be reflected in a decrease in the hydrophobic moment of the peptide. However, some modifications (e.g., D-amino acid substitutions, changes to the charge distribution of the polar face residues and replacing Lys residues with Arg residues) of the amphipathic helix may not alter the calculated hydrophobic moment, but will reduce the lipid affinity of the peptide. In such instances, a functional test of lipid affinity, such as retention time on reverse phase HPLC can be used to assess the impact of any change on the lipid affinity of the peptide (see, e.g., FIG. 8). Additional, non-limiting examples of functional tests that can be used to measure the lipid affinity of the multi-domain peptides disclosed herein include: surface monolayer exclusion pressure (Palgunachari et al., *Arterioscler. Thromb. Vasc. Biol.* 16:328-338, 1996), binding affinity to phospholipid vesicles (Palgunachari et al., *Arterioscler. Thromb. Vasc. Biol.* 16:328-338, 1996) and DMPC vesicle solubilization (Remaley et al., *J. Lipid Res.* 44:828-836, 2003). Further examples of alternative methods of calculating the predicted lipid affinity of the multi-domain peptides include: total hydrophobic moment, total peptide hydrophobicity, total peptide hydrophobicity per residue, hydrophobicity of amino acids on the hydrophobic face, hydrophobicity per residue of amino acids on the hydrophobic face, and calculated lipid affinity based on predicted peptide penetration into phospholipid bilayers (Palgunachari et al., *Arterioscler. Thromb. Vasc. Biol.* 16:328-338, 1996). Regardless of the parameter(s) used to assess the lipid affinity of the multi-domain peptides, those peptides that contain at least two or more helices, with at least one helix having relatively high lipid affinity and one helix having relatively low lipid affinity, are considered to be encompassed by the present disclosure. If alternative tests or alternative calculations are used instead of the hydrophobic moment calculation for calculating lipid affinity, the optimal value of lipid affinity for the high and low lipid affinity helices can be functionally determined by performing cytotoxicity assays (see, e.g., FIG. 9) and lipid efflux assays on non-ABCA1 expressing and ABCA1 expressing cells (see, e.g., FIG. 10).

Also encompassed by the present disclosure are multi-domain peptides or peptide analogs, wherein the multiple amphipathic α-helical domains are comprised of dimers, trimers, tetramers and even higher order polymers (i.e., "multimers") comprising the same or different sequences. Such multimers may be in the form of tandem repeats. The amphipathic α-helical domains may be directly attached to one another or separated by one or more linkers. The amphipathic α-helical domains can be connected in a head-to-tail fashion (i.e., N-terminus to C-terminus), a head-to-head fashion, (i.e., N-terminus to N-terminus), a tail-to-tail fashion (i.e., C-terminus to C-terminus), and/or combinations thereof. In one embodiment, the multimers are tandem repeats of two, three, four, and up to about ten amphipathic α-helical domains, but any number of amphipathic α-helical domains that has the desired effect of specifically promoting ABCA1 lipid efflux with low cytotoxicity can be used.

Additional aspects of the disclosure include analogs, variants, derivatives, and mimetics based on the amino acid sequence of the multi-domain peptides disclosed herein. Typically, mimetic compounds are synthetic compounds having a three-dimensional structure (of at least part of the mimetic compound) that mimics, for example, the primary, secondary, and/or tertiary structural, and/or electrochemical characteristics of a selected peptide, structural domain, active site, or binding region (e.g., a homotypic or heterotypic binding site, a catalytic active site or domain, a receptor or ligand binding interface or domain, or a structural motif) thereof. The mimetic compound will often share a desired biological activity with a native peptide, as discussed herein (e.g., the ability to interact with lipids). Typically, at least one subject biological activity of the mimetic compound is not substantially reduced in comparison to, and is often the same as or greater than, the activity of the native peptide on which the mimetic was modeled.

A variety of techniques well known to one of skill in the art are available for constructing peptide mimetics with the same, similar, increased, or reduced biological activity as the corresponding native peptide. Often these analogs, variants, derivatives and mimetics will exhibit one or more desired activities that are distinct or improved from the corresponding native peptide, for example, improved characteristics of solubility, stability, lipid interaction, susceptibility to hydrolysis or proteolysis (see, e.g., Morgan and Gainor, *Ann. Rep. Med. Chem.* 24:243-252, 1989) and/or lipoprotein lipase activity. For example, a peptide mimetic with lipoprotein lipase activity may be generated by incorporating apoC-II amino acid residues known to be involved in apoC-II lipoprotein lipase activation (such as one or more of the amino acids provided in SEQ ID NO:69) into one of the disclosed multi-domain peptides. In one particular example, a peptide mimetic with lipid efflux activity and lipoprotein lipase activating activity is a peptide with an amino acid sequence provided by SEQ ID NOs: 70-75, such as SEQ ID NO: 70.

In addition, mimetic compounds of the disclosure can have other desired characteristics that enhance their therapeutic application, such as increased cell permeability, greater affinity and/or avidity for a binding partner, and/or prolonged biological half-life. The mimetic compounds of the disclosure can have a backbone that is partially or completely non-peptide, but with side groups identical to the side groups of the amino acid residues that occur in the peptide on which the mimetic compound is modeled. Several types of chemical bonds, for example, ester, thioester, thioamide, retroamide, reduced carbonyl, dimethylene and ketomethylene bonds, are known in the art to be generally useful substitutes for peptide bonds in the construction of protease-resistant mimetic compounds.

In one embodiment, multi-domain peptides useful within the disclosure are modified to produce peptide mimetics by replacement of one or more naturally occurring side chains of the 20 genetically encoded amino acids (or D-amino acids) with other side chains, for example with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, 5 to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,689; 4,301,144; 4,670,417; 4,791,192; and 4,179,337.

Other peptide analogs and mimetics within the scope of the disclosure include glycosylation variants, and covalent or aggregate conjugates with other chemical moieties. Covalent derivatives can be prepared by linkage of functionalities to groups which are found in amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues (e.g., lysine or arginine). Acyl groups are selected from the group of alkyl-moieties including C3 to C18 normal alkyl, thereby forming alkanoyl aroyl species. Also embraced are versions of a native primary amino acid sequence which have other minor modifications, including phosphorylated amino acid residues, for example, phosphotyrosine, phosphoserine, or phosphothreonine, or other moieties, including ribosyl groups or cross-linking reagents.

In another embodiment, a detectable moiety can be linked to the multi-domain peptides or peptide analogs disclosed herein, creating a peptide/peptide analog-detectable moiety conjugate. Detectable moieties suitable for such use include any composition detectable by spectroscopic, photochemical, biochemical, immunochemical, electrical, optical or chemical means. The detectable moieties contemplated for the present disclosure can include, but are not limited to, an immunofluorescent moiety (e.g., fluorescein, rhodamine, Texas red, and the like), a radioactive moiety (e.g., $^3$H, $^{32}$P, $^{125}$I, $^{35}$S), an enzyme moiety (e.g., horseradish peroxidase, alkaline phosphatase), a colorimetric moiety (e.g., colloidal gold, biotin, colored glass or plastic, and the like). The detectable moiety can be liked to the multi-domain peptide or peptide analog at either the N- and/or C-terminus Optionally, a linker can be included between the multi-domain peptide or peptide analog and the detectable moiety.

Means of detecting such moieties are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In another embodiment, an additional functional domain or peptide can be linked to the multi-domain peptides or peptide analogs disclosed herein, creating a peptide/peptide analog-additional functional domain/peptide conjugate. The additional functional domain or peptide can be linked to the multi-domain peptide or peptide analog at either the N- and/or C-terminus. Optionally, a linker can be included between the multi-domain peptide or peptide analog and the additional functional domain or peptide. The additional functional domain or peptide can enhance the ability of the multi-domain peptide or peptide analog to efflux lipids from cells in a non-cytotoxic manner, and/or enhance its therapeutic efficacy. Exemplary additional functional domains/peptides include those shown in Table 5.

TABLE 5

Exemplary additional functional domains.

| Functional Domain or Peptide | Sequence |
|---|---|
| Cell recognition sequences | |
| Heparin binding site | RKNR; (SEQ ID NO: 46) KKWVR (SEQ ID NO: 47) |
| Integrin binding site | RGD (and variants) (SEQ ID NO: 48) |
| P-selectin site | DVEWVDVSY (SEQ ID NO: 49) |
| Internalization sequences | |
| TAT HIV sequence | RKKRRQRRRPPQ; (SEQ ID NO: 50) RRRQRRKKR (SEQ ID NO: 51) |
| Panning sequence | RRPXR (SEQ ID NO: 52) |
| Penatratin sequence | RQIKIWFQNRRMKWKK (SEQ ID NO: 53) |
| Neutral cholesterol esterase activation | |
| SAA C-terminus sequence | GHEDTMADQEANRHGRSGGDPNYYRPPGGY (SEQ ID NO: 54) |
| Inhibition of ACAT | |
| SAA N-terminus sequence | GFFSFIGEAFQGAGDMWRAY (SEQ ID NO: 55) |
| Increase liver affinity | |
| LDL receptor sequence | KAEYKKNKHRH; (SEQ ID NO: 56) YTRLTRKRGLK (SEQ ID NO: 57) |
| Anti-oxidant activity | |
| Modified 18A sequence | DWLKAFYCKVAEKLKEAF; (SEQ ID NO: 58) DWLKAFYDKVAEKLKCAF (SEQ ID NO: 59) |
| ApoA-I Milano sequence | YSDGLRQCLAARLDALKDR (SEQ ID NO: 60) |

TABLE 5-continued

Exemplary additional functional domains.

| Functional Domain or Peptide | Sequence |
|---|---|
| Heavy metal chelation | |
| 6x-His sequence | HHHHHH (SEQ ID NO: 61) |
| Lactoferrin sequence | FQWQRNIRKVR (SEQ ID NO: 62) |
| Lipoprotein Lipase activation sequence | |
| apoC-II (residue 61-70) | xxYxxIxxDQ; (SEQ ID NO: 69) wherein x is any amino acid that will allow the domain to activate lipoprotein lipase |

Cell recognition sequences can increase the ability of the multi-domain peptides or peptide analogs containing these sequences to bind to cells, the prerequisite first step in ABCA1-mediated cholesterol efflux (Remaley et al., *Biochem. Biophys. Res. Commun.* 280:818-823, 2001). Cell internalization sequences, can increase the cellular uptake of the multi-domain peptides or peptide analogs into intracellular compartments, where the initial lipidation of the peptides has been proposed to occur (Neufeld et al., *J. Biol. Chem.* 279:15571-15578, 2004), thus facilitating lipid efflux. Sequences that activate neutral cholesterol hydrolase (Kisilevsky et al., *J. Lipid Res.* 44:2257-2269, 2003) can increase the amount of intracellular free cholesterol, the form of cholesterol that effluxes from cells. Similarly, the inhibition of ACAT blocks the esterification of cholesterol to cholesteryl ester, thus increasing the pool of free cholesterol for efflux by the multi-domain peptides or peptide analogs (Kisilevsky et al., *J. Lipid Res.* 44:2257-2269, 2003). Sequences that target the multi-domain peptides or peptide analogs to the liver can facilitate the last step of reverse cholesterol transport, the hepatic uptake and excretion of cholesterol into the bile (Collet et al., *J. Lipid Res.* 40:1185-1193, 1999). Part of the beneficial effect of apoA-I and synthetic peptide mimics is believed to be due to their anti-inflammatory and anti-oxidant properties (Van Lenten et al., *J. Clin. Invest.* 96:2758-2767, 1995). Sequences containing domains that sequester oxidized lipids (Datta et al., *J. Biol. Chem.* 279:26509-26517, 2004), that act as antioxidants (Bielicki et al., *Biochem.* 41:2089-2096, 2002), or that chelate heavy metals (Wakabayashi et al., *Biosci. Biotechnol. Biochem.* 63:955-957, 1999), which promote lipid oxidation, can compliment the lipid efflux properties of the multi-domain peptides or peptide analogs by also preventing lipid oxidation. Lipoprotein lipase activation sequences can prevent, reduce or inhibit hypertriglyceridemia associated with administration of any of the disclosed multi-domain peptides or peptide analogs. In an example, lipoprotein lipase activation sequences result in triglyceride levels of no greater than 200 mg/dl.

LPL activation can be determined by methods known to those of skill in the art. In a particular example, an assay mixture of 200 μl containing 2 mg of triacylglycerols from a lipid emulsion can be used. The medium can contain 0.1 M NaCl, 0.1 M Tris-Cl, 20 μg of heparin, and 12 mg of bovine serum albumin (pH 8.5). To study the activation, peptides can be dissolved in 5 M urea, 10 mM Tris-Cl (pH 8.2). Known activators of LPL, such as apoC-II, can be used as a positive control. The protein concentration can be determined by a bicinchoninic acid protein assay. Five μl of the stock solution of apoCII, or the same volume of dilutions in 5 M urea, 10 mM Tris (pH 8.2), can be added to the incubations. The reactions can be started by addition of LPL and stopped after incubation for 15 min at 25° C. by addition of organic solvents for extraction of the labeled free fatty acids. The lipase activity can be expressed in units/mg of LPL, where 1 unit corresponds to release of 1 μmol of fatty acid per min. An at least 10% increase in LPL activity, which is more than 3× the coefficient of variation of most LPL assay, in the presence of a test peptide as compared to LPL activity in the absence of the test peptide, identifies the peptide as an LPL activating peptide.

In particular embodiments, the ability of the test peptides to activate LPL in vivo, can be determined by administering one or more of the peptides. Triglycerides levels in a sample taken from a subject receiving the peptide alone can then be compared to those levels present in a sample taken prior to the subject receiving the peptide or compared to a reference sample containing a known amount of triglycerides. Triglyceride levels of less than 150 mg/dl following peptide administration indicate that the peptide is an LPL activator or a peptide that causes a statistically significant decrease in the baseline triglyceride level when tested in vivo. The linkers contemplated by the present disclosure can be any bifunctional molecule capable of covalently linking two peptides to one another. Thus, suitable linkers are bifunctional molecules in which the functional groups are capable of being covalently attached to the N- and/or C-terminus of a peptide. Functional groups suitable for attachment to the N- or C-terminus of peptides are well known in the art, as are suitable chemistries for effecting such covalent bond formation.

The linker may be flexible, rigid or semi-rigid. Suitable linkers include, for example, amino acid residues such as Pro or Gly or peptide segments containing from about 2 to about 5, 10, 15, 20, or even more amino acids, bifunctional organic compounds such as $H_2N(CH_2)_nCOOH$ where n is an integer from 1 to 12, and the like. Examples of such linkers, as well as methods of making such linkers and peptides incorporating such linkers, are well-known in the art (see, e.g., Hunig et al., *Chem. Ber.* 100:3039-3044, 1974 and Basak et al., *Bioconjug. Chem.* 5:301-305, 1994).

Conjugation methods applicable to the present disclosure include, by way of non-limiting example, reductive amination, diazo coupling, thioether bond, disulfide bond, amidation and thiocarbamoyl chemistries. In one embodiment, the amphipathic α-helical domains are "activated" prior to conjugation. Activation provides the necessary chemical groups for the conjugation reaction to occur. In one specific, non-limiting example, the activation step includes derivatization with adipic acid dihydrazide. In another specific, non-limiting example, the activation step includes derivatization with the N-hydroxysuccinimide ester of 3-(2-pyridyl dithio)-propionic acid. In yet another specific, non-limiting example, the activation step includes derivatization with succinimidyl 3-(bromoacetamido) propionate. Further, non-limiting examples of derivatizing agents include succinimidylformylbenzoate and succinimidyllevulinate.

V. Synthesis and Purification of the Peptides

The single and multi-domain peptides or peptide analogs of the disclosure can be prepared using virtually any technique known to one of ordinary skill in the art for the preparation of peptides. For example, the peptides can be prepared using step-wise solution or solid phase peptide syntheses, or recombinant DNA techniques, or the equivalents thereof.

A. Chemical Synthesis

Peptides of the disclosure having either the D- or L-configuration can be readily synthesized by automated solid phase procedures well known in the art. Suitable syntheses can be performed by utilizing "T-boc" or "F-moc" procedures. Techniques and procedures for solid phase synthesis are described in *Solid Phase Peptide Synthesis: A Practical Approach*, by E. Atherton and R. C. Sheppard, published by IRL, Oxford University Press, 1989. Alternatively, the multi-domain peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). This is particularly the case with glycine containing peptides. Other methods useful for synthesizing the multi-domain peptides of the disclosure are described in Nakagawa et al., *J. Am. Chem. Soc.* 107:7087-7092, 1985.

Additional exemplary techniques known to those of ordinary skill in the art of peptide and peptide analog synthesis are taught by Bodanszky, M. and Bodanszky, A., *The Practice of Peptide Synthesis*, Springer Verlag, New York, 1994; and by Jones, J., *Amino Acid and Peptide Synthesis*, 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups.

Peptides of the disclosure having either the D- or L-configuration can also be readily purchased from commercial suppliers of synthetic peptides. Such suppliers include, for example, Advanced ChemTech (Louisville, Ky.), Applied Biosystems (Foster City, Calif.), Anaspec (San Jose, Calif.), and Cell Essentials (Boston, Mass.).

B. Recombinant Synthesis

If the peptide is composed entirely of gene-encoded amino acids, or a portion of it is so composed, the multi-domain peptide or the relevant portion can also be synthesized using conventional recombinant genetic engineering techniques. For recombinant production, a polynucleotide sequence encoding the multi-domain peptide is inserted into an appropriate expression vehicle, that is, a vector which contains the necessary elements for the transcription and translation of the inserted coding sequence, or in the case of an RNA viral vector, the necessary elements for replication and translation. The expression vehicle is then transfected into a suitable target cell which will express the multi-domain peptide. Depending on the expression system used, the expressed peptide is then isolated by procedures well-established in the art. Methods for recombinant protein and peptide production are well known in the art (see, e.g., Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, Ch. 17 and Ausubel et al. *Short Protocols in Molecular Biology*, $4^{th}$ ed., John Wiley & Sons, Inc., 1999).

To increase efficiency of production, the polynucleotide can be designed to encode multiple units of the multi-domain peptide separated by enzymatic cleavage sites. The resulting polypeptide can be cleaved (e.g., by treatment with the appropriate enzyme) in order to recover the peptide units. This can increase the yield of peptides driven by a single promoter. In one embodiment, a polycistronic polynucleotide can be designed so that a single mRNA is transcribed which encodes multiple peptides, each coding region operatively linked to a cap-independent translation control sequence, for example, an internal ribosome entry site (IRES). When used in appropriate viral expression systems, the translation of each peptide encoded by the mRNA is directed internally in the transcript, for example, by the IRES. Thus, the polycistronic construct directs the transcription of a single, large polycistronic mRNA which, in turn, directs the translation of multiple, individual peptides. This approach eliminates the production and enzymatic processing of polyproteins and can significantly increase yield of peptide driven by a single promoter.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus (CaMV) or tobacco mosaic virus (TMV)) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrp-lac hybrid promoter) and the like can be used. When cloning in insect cell systems, promoters such as the baculovirus polyhedron promoter can be used. When cloning in plant cell systems, promoters derived from the genome of plant cells (e.g., heat shock promoters, the promoter for the small subunit of RUBISCO, the promoter for the chlorophyll a/b binding protein) or from plant viruses (e.g., the 35S RNA promoter of CaMV, the coat protein promoter of TMV) can be used. When cloning in mammalian cell systems, promoters derived from the genome of mammalian cells (e.g., metallothionein promoter) or from mammalian viruses (e.g., the adenovirus late promoter, the vaccinia virus 7.5 K promoter) can be used.

C. Purification

The peptides or peptide analogs of the disclosure can be purified by many techniques well known in the art, such as reverse phase chromatography, high performance liquid chromatography, ion exchange chromatography, size exclusion chromatography, affinity chromatography, gel electrophoresis, and the like. The actual conditions used to purify a particular multi-domain peptide or peptide analog will depend, in part, on synthesis strategy and on factors such as net charge, hydrophobicity, hydrophilicity, and the like, and will be apparent to those of ordinary skill in the art.

For affinity chromatography purification, any antibody which specifically binds the multi-domain peptide or peptide analog may be used. For the production of antibodies, various host animals, including but not limited to, rabbits, mice, rats, and the like, may be immunized by injection with a multi-domain peptide or peptide analog. The multi-domain peptide or peptide analog can be attached to a suitable carrier (e.g., BSA) by means of a side chain functional group or linker attached to a side chain functional group. Various adjuvants may be used to increase the immunological response, depending on the host species, including but not limited to, Freund's (complete and incomplete), mineral gels (e.g., aluminum hydroxide), surface active substances (e.g., lysolecithin, pluronic polyols, polyanions, and oil emulsions), keyhole limpet hemocyanin, dinitrophenol, and potentially useful human adjuvants such as BCG (bacilli Calmette-Guerin) and *Corynebacterium parvum*.

Booster injections can be given at regular intervals, and antiserum harvested when the antibody titer thereof, as determined semi-quantitatively, for example, by double immunodiffusion in agar against known concentrations of the antigen, begins to fall. See, e.g., Ouchterlony et al., *Handbook of Experimental Immunology*, Wier, D. (ed.), Chapter 19, Blackwell, 1973. A plateau concentration of antibody is usually in the range of 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

Monoclonal antibodies to a peptide or peptide analog may be prepared using any technique which provides for the production of antibody molecules by continuous cell lines in culture, for example the classic method of Kohler & Milstein (*Nature* 256:495-97, 1975), or a derivative method thereof. Briefly, a mouse is repetitively inoculated with a few micrograms of the selected protein immunogen (e.g., a multi-domain peptide or peptide analog) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as enzyme-linked immunosorbent assay (ELISA), as originally described by Engvall (*Meth. Enzymol.*, 70:419-39, 1980), or a derivative method thereof. Selected positive clones can be expanded and their monoclonal antibody product harvested for use. Detailed procedures for monoclonal antibody production are described in Harlow and Lane, *Using Antibodies: A Laboratory Manual*, CSHL, New York, 1999. Polyclonal antiserum containing antibodies can be prepared by immunizing suitable animals with a polypeptide comprising at least one multi-domain peptide or peptide analog, which can be unmodified or modified, to enhance immunogenicity.

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178:476-96, 1989; Glockshuber et al., *Biochemistry* 29:1362-67, 1990; and U.S. Pat. No. 5,648,237 (Expression of Functional Antibody Fragments); U.S. Pat. No. 4,946,778 (Single Polypeptide Chain Binding Molecules); and U.S. Pat. No. 5,455,030 (Immunotherapy Using Single Chain Polypeptide Binding Molecules), and references cited therein. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., *Current Protocols in Immunology*, Wiley, N.Y., 1995), agglutination assays, flocculation assays, cell panning, etc., as are well known to one of skill in the art.

VI. Pharmaceutical Compositions and Uses Thereof

The peptides or peptide analogs of the disclosure (and mixtures thereof) can be used to treat any disorder in animals, especially mammals (e.g., humans), for which promoting lipid efflux is beneficial, including promoting lipid efflux without inducing hypertriglyceridemia or with reduced hypertriglyceridemia. Such conditions include, but are not limited to, hyperlipidemia (e.g., hypercholesterolemia), cardiovascular disease (e.g., atherosclerosis), restenosis (e.g., atherosclerotic plaques), peripheral vascular disease, acute coronary syndrome, reperfusion myocardial injury, and the like. The peptides or peptide analogs of the disclosure can also be used during the treatment of thrombotic stroke and during thrombolytic treatment of occluded coronary artery disease. In some examples, peptides or peptide analogs including lipid efflux activity and lipoprotein lipase activating activity, such as a peptide with an amino acid sequence provided by any one of SEQ ID NOs: 70-75, can be used to treat any of the aforementioned disorders.

The peptides or peptide analogs can be used alone or in combination therapy with other lipid lowering compositions or drugs used to treat the foregoing conditions, or with agents (such as peptides) that activate LPL activity. Such combination therapies include, but are not limited to simultaneous or sequential administration of the drugs involved. For example, in the treatment of hypercholesterolemia or atherosclerosis, the peptide or peptide analog formulations can be administered with any one or more of the cholesterol lowering therapies currently in use, for example, bile-acid resins, niacin and statins.

In other embodiments, the multi-domain peptide or peptide analog formulations can be administered with a lipoprotein lipase activating agent, such as an apoC-II protein, variant or fragment thereof, to prevent, reduce or inhibit hypertriglyceridemia associated with the administration of any of the disclosed peptides or peptide analogs.

In another embodiment, the multi-domain peptides or peptide analogs can be used in conjunction with statins or fibrates to treat hyperlipidemia, hypercholesterolemia and/or cardiovascular disease, such as atherosclerosis. In yet another embodiment, the multi-domain peptides or peptide analogs of the disclosure can be used in combination with an anti-microbials agent and/or an anti-inflammatory agent. In a further embodiment, the multi-domain peptides can also be expressed in vivo, by using any of the available gene therapy approaches.

A. Administration of Peptides or Peptide Analogs

In some embodiments, multi-domain peptides or peptide analogs can be isolated from various sources and administered directly to the subject. For example, a multi-domain peptide or peptide analog can be expressed in vitro, such as in an *E. coli* expression system, as is well known in the art, and isolated in amounts useful for therapeutic compositions.

In exemplary applications, therapeutic compositions are administered to a subject suffering from a dyslipidemic or vascular disorder, such as hyperlipidemia, hyperlipoproteinemia, hypercholesterolemia, hypertriglyceridemia, HDL deficiency, apoA-I deficiency, coronary artery disease, atherosclerosis, thrombotic stroke, peripheral vascular disease, restenosis, acute coronary syndrome, or reperfusion myocardial injury, in an amount sufficient to inhibit or treat the dyslipidemic or vascular disorder. Amounts effective for this use will depend upon the severity of the disorder and the general state of the subject's health. A therapeutically effective amount of the compound is that which provides either subjective relief of a symptom(s) or an objectively identifiable improvement as noted by the clinician or other qualified observer.

A multi-domain peptide or peptide analog can be administered by any means known to one of skill in the art (see, e.g., Banga, "Parenteral Controlled Delivery of Therapeutic Peptides and Proteins," in *Therapeutic Peptides and Proteins*, Technomic Publishing Co., Inc., Lancaster, Pa., 1995), such as by intramuscular, subcutaneous, or intravenous injection, but even oral, nasal, or anal administration is contemplated. In one embodiment, administration is by subcutaneous or intramuscular injection. To extend the time during which the multi-domain peptide or peptide analog is available to inhibit or treat a dyslipidemic or vascular disorder, the multi-domain peptide or peptide analog can be provided as an implant, an oily injection, or as a particulate system. The particulate system can be a microparticle, a microcapsule, a microsphere, a nanocapsule, or similar particle (Banga, "Parenteral Controlled Delivery of Therapeutic Peptides and Proteins," in *Therapeutic Peptides and Proteins*, Technomic Publishing Co., Inc., Lancaster, Pa., 1995).

In one specific, non-limiting example, a multi domain peptide is administered that includes one or more of the amino acid sequences shown in SEQ ID NOs: 3-45 and 70-75. In another specific, non-limiting example, a multi domain peptide is administered that includes one or more of the amino acid sequences shown in SEQ ID NOs: 3-45, which promotes lipid efflux, in combination with a lipoprotein lipase activating agent, such as an apoC-II protein, fragment or variant thereof (e.g., a peptide with an amino acid sequence set forth in any one of SEQ ID NOs: 63-69); such LPL activating agent need not be covalently linked, or even administered simultaneously with, the peptide that promotes lipid efflux.

B. Administration of Nucleic Acid Molecules

In some embodiments where the therapeutic agent is composed entirely of gene-encoded amino acids, or a portion of it is so composed, administration of the multi-domain peptide or mixture of peptides, or the relevant portion, can be achieved by an appropriate nucleic acid expression vector (or combination of vectors) which is administered so that it becomes intracellular, for example, by use of a retroviral vector (see U.S. Pat. No. 4,980,286), or by direct injection, or by use of microparticle bombardment (e.g., a gene gun; Biolistic, DuPont), or coating with lipids or cell-surface receptors or transfecting agents, or by administering it in linkage to a homeobox-like peptide which is known to enter the nucleus (see e.g., Joliot et al., *Proc. Natl. Acad. Sci.*, 88:1864-1868, 1991). Alternatively, the nucleic acid can be introduced intracellularly and incorporated within host cell DNA for expression, for example, by homologous or non-homologous recombination.

Use of a DNA expression vector (e.g., the vector pCDNA) is an example of a method of introducing the foreign cDNA into a cell under the control of a strong viral promoter (e.g., cytomegalovirus) to drive the expression. However, other vectors can be used. Other retroviral vectors (such as pRETRO-ON, BD Biosciences, Palo Alto, Calif.) also use this promoter but have the advantages of entering cells without any transfection aid, integrating into the genome of target cells only when the target cell is dividing. It is also possible to turn on the expression of a therapeutic nucleic acid by administering tetracycline when these plasmids are used. Hence these plasmids can be allowed to transfect the cells, then administer a course of tetracycline to achieve regulated expression.

Other plasmid vectors, such as pMAM-neo (BD Biosciences, Palo Alto, Calif.) or pMSG (Invitrogen, Carlsbad, Calif.) use the MMTV-LTR promoter (which can be regulated with steroids) or the SV10 late promoter (pSVL, Invitrogen, Carlsbad, Calif.) or metallothionein-responsive promoter (pBPV, Invitrogen, Carlsbad, Calif.) and other viral vectors, including retroviruses. Examples of other viral vectors include adenovirus, AAV (adeno-associated virus), recombinant HSV, poxviruses (vaccinia) and recombinant lentivirus (such as HIV). All these vectors achieve the basic goal of delivering into the target cell the cDNA sequence and control elements needed for transcription.

Retroviruses have been considered a preferred vector for gene therapy, with a high efficiency of infection and stable integration and expression (Orkin et al., *Prog. Med. Genet.* 7:130-142, 1988). A nucleic acid encoding the multi-domain peptide can be cloned into a retroviral vector and driven from either its endogenous promoter (where applicable) or from the retroviral LTR (long terminal repeat). Other viral transfection systems may also be utilized for this type of approach, including adenovirus, AAV (McLaughlin et al., *J. Virol.* 62:1963-1973, 1988), vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

In addition to delivery of a nucleic acid encoding the multi-domain peptide to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.*, 11:175-180, 1999; Lee and Huang, *Crit. Rev. Ther. Drug Carrier Syst.*, 14:173-206, 1997; and Cooper, *Semin. Oncol.*, 23:172-187, 1996). For instance, cationic liposomes have been analyzed for their ability to transfect monocytic leukemia cells, and shown to be a viable alternative to using viral vectors (De Lima et al., *Mol. Membr. Biol.*, 16:103-109, 1999). Such cationic liposomes can also be targeted to specific cells through the inclusion of, for instance, monoclonal antibodies or other appropriate targeting ligands (Kao et al., *Cancer Gene Ther.*, 3:250-256, 1996).

C. Representative Methods of Administration, Formulations and Dosage

The provided multi-domain peptides or peptide analogs, constructs, or vectors encoding such peptides, can be combined with a pharmaceutically acceptable carrier (e.g., a phospholipid or other type of lipid) or vehicle for administration to human or animal subjects. In some embodiments, more than one multi-domain peptide or peptide analog can be combined to form a single preparation. The multi-domain peptides or peptide analogs can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The pharmaceutical compositions provided herein, including those for use in treating dyslipidemic and vascular disorders, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes. In one embodiment, multi-domain peptides or peptide analogs with suitable features of ABCA1-specificity and low cytotoxicity can be precomplexed with phospholipids or other lipids into either discoidal or spherical shape particles prior to administration to subjects.

In another embodiment, it may be desirable to administer the pharmaceutical compositions locally to the area in need of treatment. This may be achieved by, for example, and not by way of limitation, local or regional infusion or perfusion during surgery, topical application (e.g., wound dressing), injection, catheter, suppository, or implant (e.g., implants formed from porous, non-porous, or gelatinous materials, including membranes, such as sialastic membranes or fibers), and the like.

In a specific embodiment, one or more of the disclosed peptides capable of promoting lipid efflux and activating lipoprotein lipase may be associated either by coating or impregnating an implant such as stent to treat a dyslipidemic or vascular disorder. These peptides are prepared and purified as described herein. In an example, the implant can be partially or completely coated with the peptide. For instance, the luminal surface of the implant may be coated with the peptide. Such configuration is believed to reduce atherosclerotic plaques in arteries often associated with atherosclerosis while minimizing the amount of coating material and time required to prepare the implant. The peptide may be attached to the implant by any chemical or mechanical bond or force, including linking agents. Alternatively, the coating may be directly linked (tethered) to the first surface, such as through silane groups. In other examples, the implant may be impregnated with at least one peptide by methods known to those of skill in the art so that multiple surfaces (such as the outer and inner surfaces) of the implant include the peptide.

In an additional embodiment, the implant may be coated or impregnated with materials in addition to the disclosed peptides to further enhance their bio-utility. Examples of suitable coatings are medicated coatings, drug-eluting coatings, hydrophilic coatings, smoothing coatings.

In one embodiment, administration can be by direct injection at the site (or former site) of a tissue that is to be treated, such as the heart or the peripheral vasculature. In another embodiment, the pharmaceutical compositions are delivered in a vesicle, in particular liposomes (see, e.g., Langer, *Science* 249:1527-1533, 1990; Treat et al., in *Liposomes in the Therapy of Infectious Disease and Cancer*, Lopez-Berestein and Fidler (eds.), Liss, N.Y., pp. 353-365, 1989).

In yet another embodiment, the pharmaceutical compositions can be delivered in a controlled release system. In one embodiment, a pump can be used (see, e.g., Langer *Science* 249:1527-1533, 1990; Sefton *Crit. Rev. Biomed. Eng.* 14:201-240, 1987; Buchwald et al., *Surgery* 88:507-516, 1980; Saudek et al., *N. Engl. J. Med.* 321:574-579, 1989). In another embodiment, polymeric materials can be used (see, e.g., Ranger et al., *Macromol. Sci. Rev. Macromol. Chem.* 23:61-64, 1983; Levy et al., *Science* 228:190-192, 1985; During et al., *Ann. Neurol.* 25:351-356, 1989; and Howard et al., *J. Neurosurg.* 71:105-112, 1989). Other controlled release systems, such as those discussed in the review by Langer (*Science* 249:1527-1533, 1990), can also be used.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. An example of such a dosage range is 0.1 to 200 mg/kg body weight in single or divided doses. Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration. By way of example, intramuscular injections may range from about 0.1 ml to about 1.0 ml. Those of ordinary skill in the art will know appropriate volumes for different routes of administration.

The subject matter of the present disclosure is further illustrated by the following non-limiting Examples.

EXAMPLES

Example 1

Lipid Efflux from Cells Mediated by Synthetic Peptides

This example demonstrates the ability of synthetic peptides containing amphipathic helices to efflux lipid from ABCA1-expressing cells.

HeLa cells stably transfected with human ABCA1 cDNA (ABCA1 cells) and HeLa cells transfected with only a hygromycin-resistant control plasmid (control cells) were produced and grown in α-modified Eagle's medium (αMEM) plus 10% fetal calf serum, as described by Remaley et al.

(*Biochem. Biophys. Res. Commun.* 280:818-823, 2001). Cholesterol and phospholipid efflux was performed for 18 hours on noncholesterol-loaded cells radiolabeledwith either cholesterol or choline (Remaley et al., *Arterioscler. Thromb. Vasc. Biol.* 17:1813-1821, 1997). Percentage efflux was calculated after subtracting the radioactive counts in the blank media (αMEM plus 1 mg/ml of BSA), and expressed as the percent of total radioactive counts removed from the cells during the efflux period.

Cell fixation was performed by a 10 minute treatment with 3% paraformaldehyde in phosphate buffered saline (PBS), followed by three washes with blank media. Lactate dehydrogenase (LDH) release from cells into the media was measured enzymatically (Roche Diagnostics, Indianapolis, Ind.) and expressed, after subtraction of LDH released into blank media, as the percentage of total cell LDH. Total cell LDH was determined after cell solubilization with 1% Triton X-100.

The 37pA peptide: DWLKAFYDKVAEKLKEAFPD-WLKAFYDKVA EKLKEAF (SEQ ID NO: 1) was synthesized by a solid-phase procedure, using a Fmoc/DIC/HOBt protocol on a Biosearch 9600 peptide synthesizer (Applied Biosystems, Foster City, Calif.). Both L-amino acid (L-37pA) and D-amino acid (D-37pA) enantiomers were synthesized. All peptides were purified to greater than 98% homogeneity by reverse-phase HPLC on an Aquapore RP-300 column.

ABCA1 cells were used to assess the ability of apoA-I and synthetic peptides to efflux lipid from cells (FIG. 1). As previously described (Hamon et al., *Nat. Cell Biol.* 2:399-406, 2000 and Remaley et al., *Biochem. Biophys. Res. Commun.* 280:818-823, 2001), control cells do not efflux significant amounts of cholesterol and phospholipid to apoA-I, but do so after transfection with ABCA1 (FIGS. 1A, B). The L-37pA peptide, which was synthesized with all L-amino acids and only has two amphipathic helices in contrast to the 10 present in apoA-I, effluxed approximately 2- to 4-fold more cholesterol and phospholipid from ABCA1 cells than from control cells (FIGS. 1C, D). Both the L-37pA peptide and apoA-I began to show saturation for lipid efflux at approximately the same protein concentration of 10 µg/ml, but because the L-37pA peptide is significantly smaller in molecular weight than apoA-I, this corresponds to a molar concentration of 2 µM for L-37pA and 0.36 µM for apoA-I. The 37pA peptide synthesized with all D-amino acids, D-37pA, was also effective in promoting cholesterol and phospholipid efflux from ABCA1 cells (FIGS. 1E, F). D-37pA had a similar dose-response curve as L-37pA, suggesting that there is not a need for a stereoselective interaction between the 37-pA peptide and the ABCA1 transporter for lipid efflux. Both L-37pA and D-37pA also consistently removed more cholesterol (5% at 40 µg/ml) and phospholipids (8% at 40 µg/ml) from control cells (FIG. 1C-F) than did apoA-I (FIGS. 1A, B).

Example 2

Lipid Efflux Time Course

This example demonstrates the cholesterol efflux time course from ABCA1-expressing cells to apoA-I and synthetic peptides containing amphipathic helices.

Figure 2B:
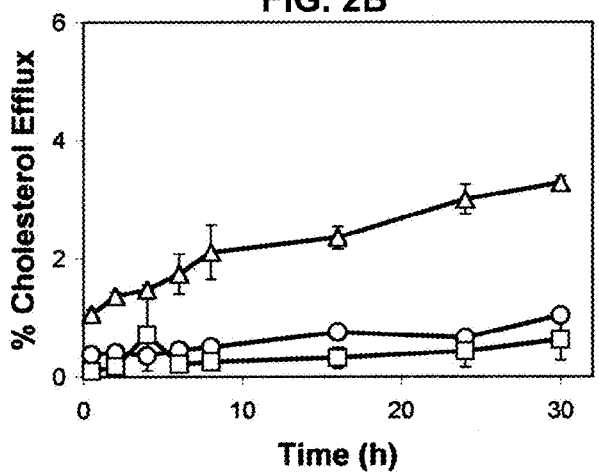

Cholesterol efflux from ABCA1 cells to apoA-I was first detectable after 2 hours and continued to increase throughout the 30 hour efflux period (FIG. 2A). In contrast, there was no significant increase above background in cholesterol efflux to apoA-I from control cells (FIG. 2B). Overall, the kinetics for cholesterol efflux to L-37pA from ABCA1 cells was similar to that of apoA-I, except that cholesterol efflux was first detectable after 30 minutes (FIG. 2A). L-37pA peptide, unlike apoA-I, also promoted cholesterol efflux from control cells but at approximately half the rate (FIG. 2B). A small amount of cholesterol efflux to L-37pA from control cells was first detectable at 30 minutes, and then it slowly continued to increase throughout the efflux period, similar to what was observed for L-37pA with ABCA1 cells.

Example 3

Importance of Amphipathic α Helices

This example demonstrates the importance of amphipathic α helices in peptide-lipid affinity and in the ability of peptides to promote lipid efflux from cells.

Figure 3:
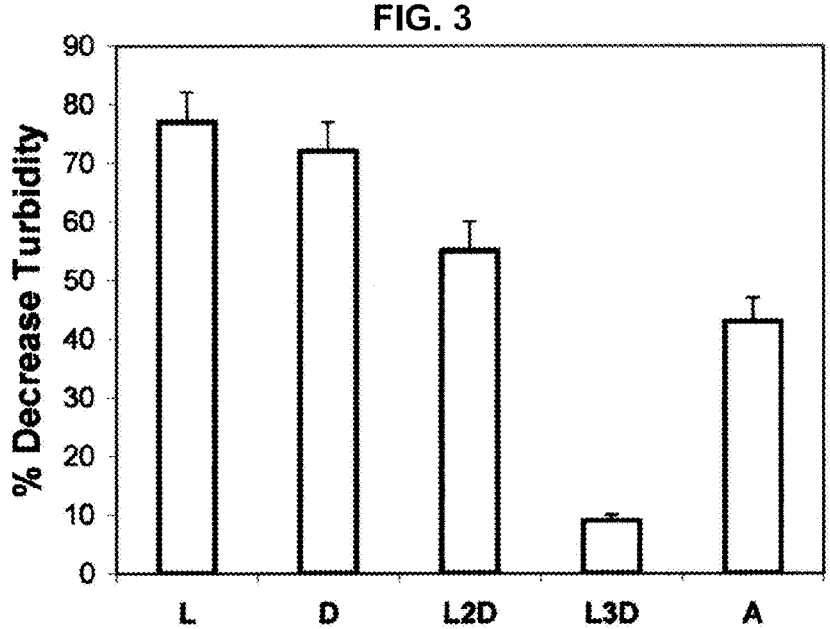
FIG. 3 is a graph illustrating solubilization of DMPC vesicles by synthetic peptides. The indicated peptides (L-37pA (L), D-37pA (D), L2D-37pA (L2D), L3D-37pA (L3D), and apoA-I (A)) at a final concentration of 0.4 mg/ml were incubated with DMPC vesicles (2 mg/ml) for 2 hours and the decrease in turbidity (indicative of vesicle lysis) was monitored at an absorbance of 350 nm. Results are expressed as the mean of triplicates ±1 SD.

The introduction of D-amino acids into a peptide that otherwise contains L-amino acids is known to interfere with the ability of a peptide to form an alpha helix (Chen et al., *J. Pept. Res.* 59:18-33, 2002). In order to test the importance of amphipathic alpha helices in peptide lipid affinity and in the ability of peptides to promote lipid efflux from cells, the following 2 peptides with the same sequence as 37pA were made with a mixture of L- and D-amino acids: (1) L2D-37pA, all L-amino acids except that D-amino acids were used for valine and tyrosine; and (2) L3D-37pA, all L-amino acids except that D-amino acids were used for alanine, lysine, and aspartic acid. The L2D-37pA and L3D-37pA peptides had lower lipid affinity, as assessed by monitoring their ability to act as detergents in the solubilization of dimyristoyl phosphatidyl choline (DMPC) vesicles. The solubilization of multilamellar DMPC vesicles (2 mg/ml) by the peptides (0.4 mg/ml) was performed in the presence of 8.5% NaBr, and the absorbance at 350 nm was measured after a 2 hour incubation at room temperature, as previously described (Jonas, *Methods of Enzymology* 128:553-581, 1986). After the 2 hour incubation, the L-37pA and D-37pA peptides nearly completely solubilized the DMPC vesicles, whereas the L3D-37pA peptide caused only a minimal decrease in turbidity (FIG. 3). The L2D-37pA peptide and apoA-I caused an intermediate level of DMPC vesicle solubilization compared to the L-37pA and L3D-37pA peptides.

When the L2D-37pA peptide was tested for lipid efflux, the substitution of D-amino acids for valine and tyrosine residues caused a greater than 75% reduction in cholesterol and phospholipid efflux from ABCA1 cells compared to the L-37pA peptide, which contains all L-amino acids (Compare FIG. 4 with FIGS. 1C, D). Even though lipid efflux was reduced from ABCA1 cells to the L2D-37pA peptide compared to apoA-1, the peptide still retained some ability to efflux lipid from ABCA1 cells, but it was unable, like apoA-I, to promote any lipid efflux from control cells (FIGS. 1A, B). In contrast, L3D-37pA, which caused only minimal DMPC vesicle solubilization (FIG. 3), was also unable to promote detectable amounts of lipid efflux from either ABCA1 cells or control cells (FIG. 4). A peptide based on the gamma crystalline protein (RMRITERDDFRGQMSEITDDCPSLQDRF-HLTEVHSLRVLEGS (SEQ ID NO: 2); Hay et al., *Biochem Biophys. Res. Commun.* 146:332-338, 1987), which contains two non-amphipathic alpha helices of approximately the same length as the helices on 37pA, was tested and also found to be completely ineffective in promoting cholesterol and phospholipid efflux from either cell line. These results are consistent with previous studies that demonstrated the importance of the amphipathic alpha helix in promoting lipid efflux (see, e.g., Gillotte et al., *J. Biol. Chem.* 274:2021-2028, 1999 and Gillotte et al., *J. of Lipid Res.* 39:1918-1928, 1998). However, the relative level of lipid efflux from the two cell lines (FIGS. 1 and 4) demonstrates that amphipathic helical peptides can promote lipid efflux in an ABCA1-dependent and an ABCA1-independent manner, although the expression of ABCA1 is necessary for those apolipoproteins and peptides, such as apoA-I and L2D-37pA, with only moderate lipid affinity, as assessed by DMPC vesicle solubilization (FIG. 3).

Example 4

Evaluation of the ABCA1-Independent Lipid Efflux Pathway

This example demonstrates that amphipathic helical peptides with high lipid affinity can promote lipid efflux in an ABCA1-independent manner.

In order to confirm that the residual lipid efflux from the control cells to L-37pA and D-37pA (see FIG. 1) was not due to a low level of endogenous ABCA1, a Tangier disease fibroblast cell line with a truncated non-functional ABCA1 transporter (Remaley et al., *Proc. Natl. Acad. Sci. USA* 96:12685-12690, 1999) was evaluated for lipid efflux (FIG. 5). ApoA-I, L-37pA, and D-37pA all effluxed cholesterol from normal fibroblasts, but apoA-I did not efflux significant amounts of cholesterol from Tangier disease fibroblasts (see also, Francis et al., *J. Clin. Invest.* 96:78-87, 1995 and Remaley et al., *Arterioscler. Thromb. Vasc. Biol.* 17:1813-1821, 1997). In contrast, both L-37pA and D-37pA were still able to efflux cholesterol from Tangier disease fibroblasts, albeit at a reduced level, thus confirming the ability of these peptides to efflux lipid from cells in the absence of ABCA1.

Figure 6A:
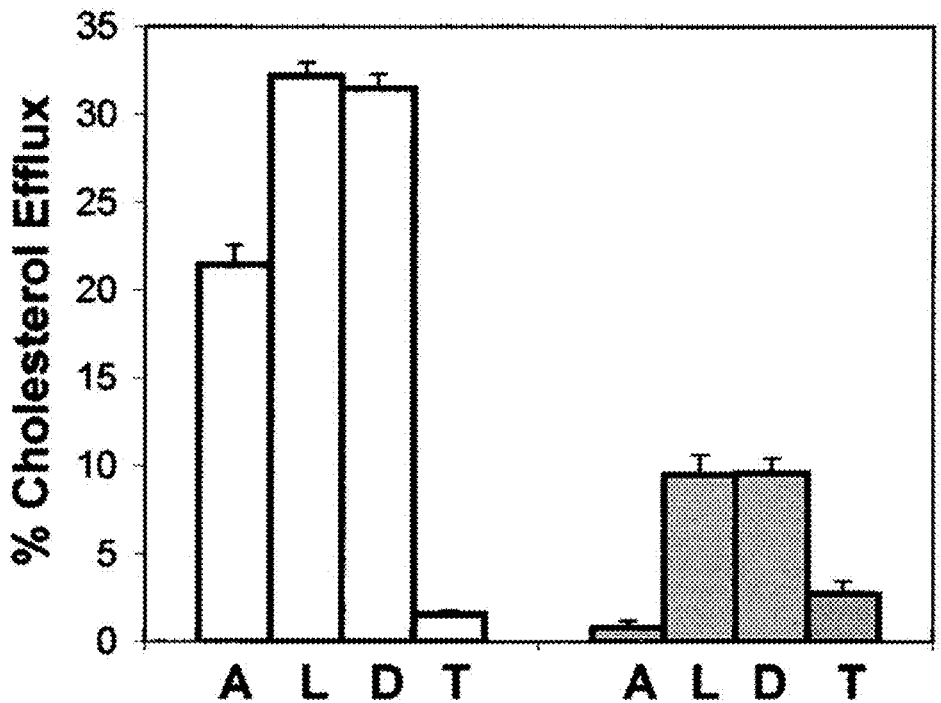
FIGS. 6A-6B are a pair of graphs illustrating the effect of cell fixation on cholesterol efflux from ABCA1 transfected cells and control cells. ABCA1 transfected cells (FIG. 6A) and control cells (FIG. 6B) were examined for their ability to efflux cholesterol when treated with apoA-I (A), L-37pA (L), D-37pA (D), and (0.02%) taurodeoxycholate (T) before (open bars) and after (solid bars) fixation with 3% paraformaldehyde. Synthetic peptides and apoA-I were used at a concentration of 10 μg/ml, and cholesterol efflux was measured after 18 hours. Efflux due to taurodeoxycholate treatment was measured after 1 hour. Results are expressed as the mean of triplicates ±1 SD.
Figure 6B:
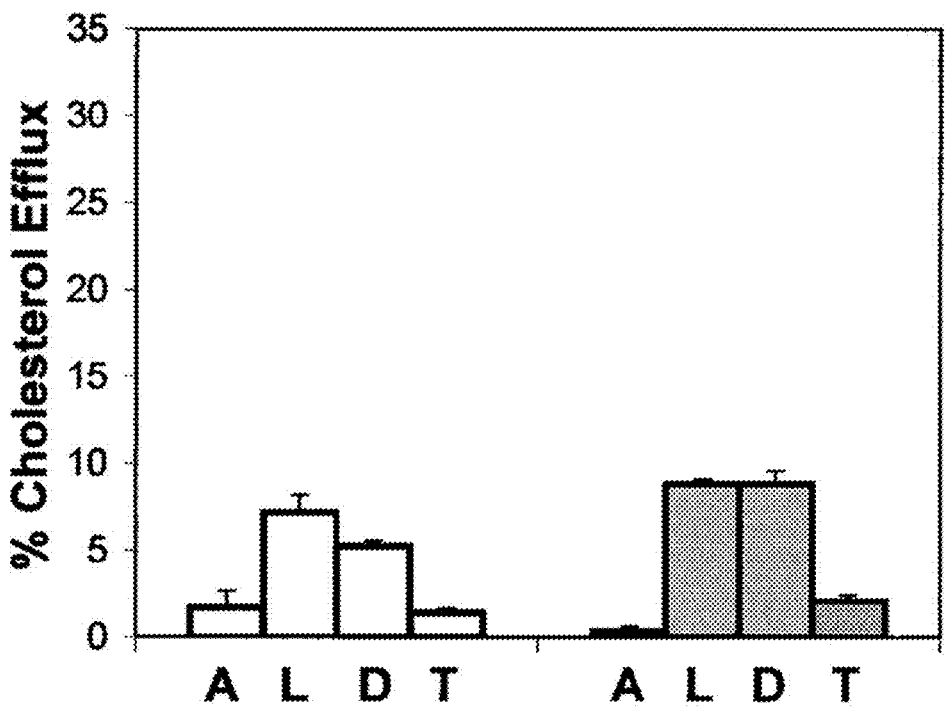

The ABCA1-independent pathway for lipid efflux was further evaluated by examining the effect of cell fixation with paraformaldehyde on cholesterol efflux to apoA-I (A), L-37pA (L), and D-37pA (D) (FIG. 6). In addition, 0.02% of taurodeoxycholate (T) was also tested for lipid efflux after 1 hour, in order to determine if a sublytic concentration of a simple detergent would also promote more lipid efflux from ABCA1 cells than from control cells. As expected, based on the ATP requirement of the ABCA1 transporter (Dean et al., *J. Lipid Res.* 42:1007-1017, 2001; Mendez, *J. Lipid Res.* 38:1807-1821, 1997), fixation of ABCA1 cells with paraformaldehyde completely blocked the ability of apoA-I to efflux cholesterol (FIG. 6A). In contrast, cell fixation of ABCA1 cells only partially reduced cholesterol efflux to the L-37pA and D-37pA peptides; approximately 30% of the baseline cholesterol efflux was still retained after cell fixation. When cholesterol efflux was tested on non-fixed control cells, the level of cholesterol efflux to L-37pA and D-37pA was similar to the level obtained with fixed ABCA1 cells (compare FIGS. 6B and 6A). Furthermore, unlike ABCA1 cells, fixation of control cells did not further reduce cholesterol efflux to the two peptides (FIG. 6B). These results indicate that lipid efflux by the peptides from ABCA1 cells occurs by both an ABCA1-dependent and an ABCA1-independent pathway, whereas lipid efflux from control cells only occurs by the ABCA1-independent pathway, which is a passive, energy-independent process that does not require viable cells.

The addition of a relatively low concentration (0.02%) of taurodeoxycholate to the cell culture efflux media for 1 hour did not alter the morphology of the cells, as assessed by light microscopy, but did result in a small amount of cholesterol efflux from ABCA1 cells (FIG. 6A), which slightly increased after fixation. Approximately the same amount of cholesterol efflux also occurred from control cells after the taurodeoxycholate treatment (FIG. 6B). Nearly identical results were also obtained with several other detergents (TX-100, NP-40, CHAPS) when tested at sublytic concentrations. This indicates that ABCA1 promotes lipid efflux to amphipathic helical proteins but does not increase the overall propensity of cells to efflux lipids to simple detergents.

The inability to completely block peptide mediated lipid efflux by cell fixation (FIG. 6) and the correlation between DMPC vesicle solubilization by the peptides with lipid efflux (FIGS. 1 and 3), suggests that lipid efflux from control cells occurs as the result of the microsolubilization of the cell membrane lipids by the detergent-like action of the amphipathic helices on the peptides. The microsolubilization of the plasma membrane of cells could, therefore, be potentially cytotoxic, but no morphologic effect was observed on the cells after incubation with the peptides or apoA-I, during the efflux experiments. Incubation of the cells with L-37pA and D-37pA at the maximum concentration and time used for the efflux studies (40 µg/ml for 18 hours) did, however, consistently result in the release of a small amount of LDH from both cell lines (control cells: L-37pA (6.1%±0.2), D-37pA (6.6%±0.1); ABCA1 cells: L-37pA (4.3%±0.04), D-37pA (5.7%±0.1)). In contrast, L2D-37pA, L3D-37pA, and apoA-1, which did not cause lipid efflux from control cells (FIGS. 2 and 3) and, therefore, appear to be incapable of effluxing lipid by the ABCA1-independent pathway, also did not cause any significant release of cell LDH above baseline (<0.5%) from either cell line.

Example 5

Competition of Peptides/apoA-I for Binding of Radiolabeled L-37pA

This example demonstrates the lack of stereoselectivity in the binding of the 37pA peptide to either ABCA1 cells or control cells.

The L-37pA peptide was labeled with $^{125}$I using iodine monochloride. Confluent cells grown on 12-well plates were incubated for 3 hours at 4° C. with the indicated concentration of the unlabeled competitor peptide in αMEM media plus 10 mg/ml of BSA (FIG. 7). The cells were then washed three times and incubated for 1 hour at 4° C. with 1 µg/ml of the radiolabeled L-37pA peptide dissolved in αMEM media plus 10 mg/ml of BSA. Cells were washed three times, and cell bound counts were determined after solubilization with 0.1 N NaOH.

Figure 7A:
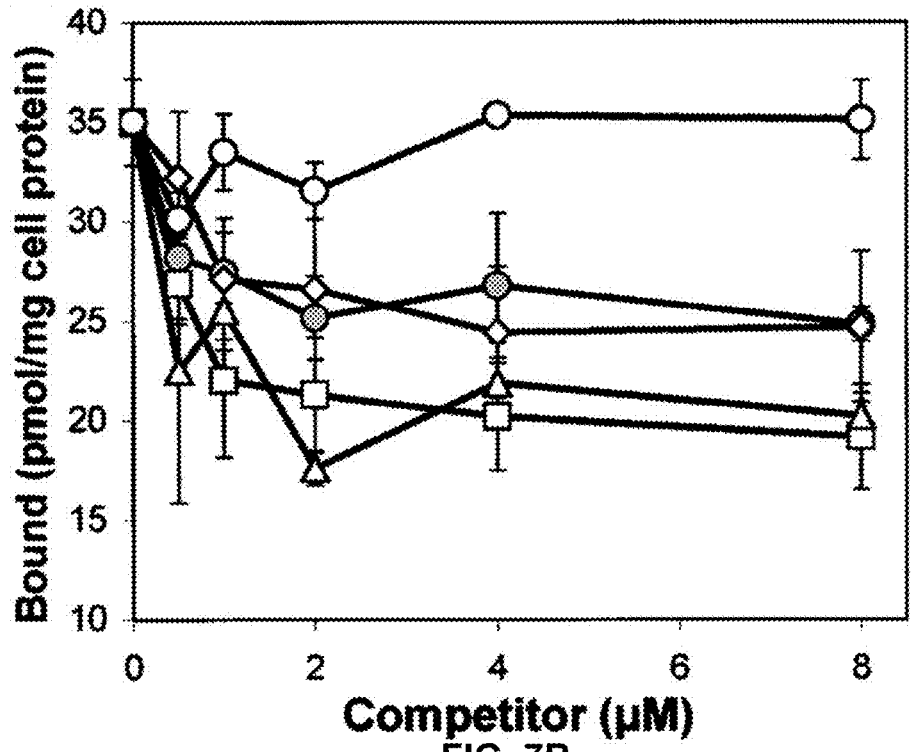
FIGS. 7A-7B are a pair of graphs illustrating the competitive binding of L-37pA peptide to ABCA1 transfected cells and control cells. ABCA1 cells (FIG. 7A) and control cells (FIG. 7B) were incubated for 3 hours at 4° C. with the indicated concentration of the competitor proteins [L-37pA (triangle), D-37pA (open square), apoA-I (closed circle), L2D-37pA (star), and L3D-37pA (open circle)] and were then washed and incubated for 1 hour at 4° C. with 1 μg/ml of radiolabeled L-37pA peptide. Results are expressed as the mean of triplicates ±1 SD.
Figure 7B:
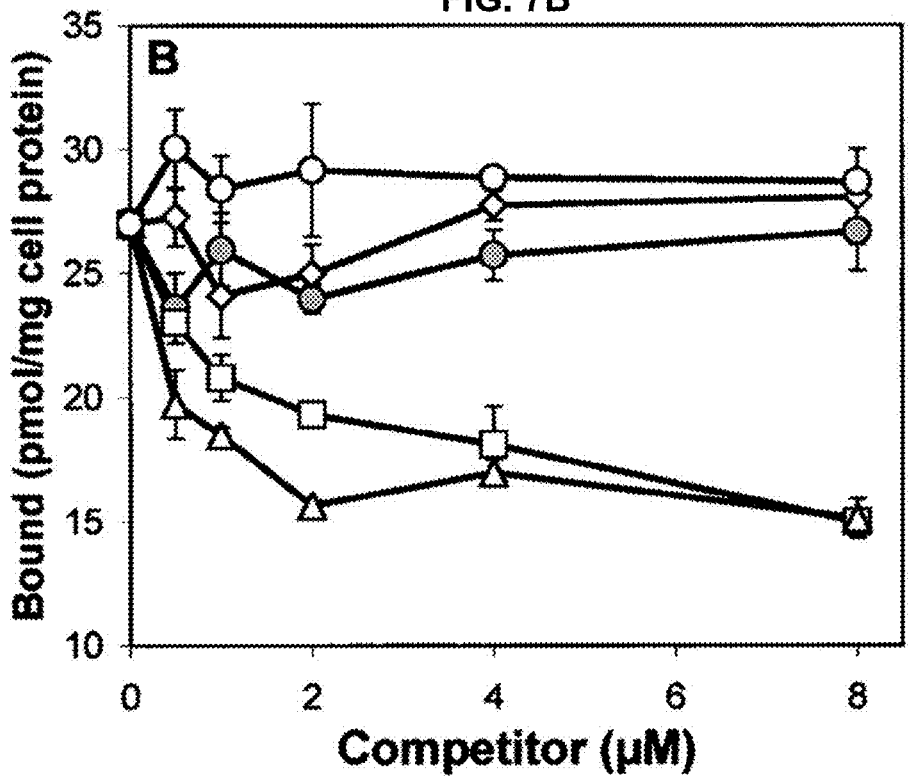

A two-step sequential competitive binding assay was performed in order to prevent any potentially interfering interaction of the radiolabeled peptide with the competitor proteins (Mendez et al., *J. Clin. Invest.* 94:1698-1705, 1994). The cells were first incubated with the competitor proteins for 3 hours, washed, and then the cell binding of the radiolabeled L-37 peptide was measured. At 8 µM, the maximum concentration tested, which is equivalent to the maximum peptide protein concentration of 40 µg/ml used in the lipid efflux studies (FIG. 1), the unlabelled L-37pA peptide blocked the binding of approximately 40% of the labeled L-37pA peptide (FIG. 7A). D-37pA was similarly effective in competing for the binding of L-37pA, indicating a lack of stereoselectivity in the binding of the peptides to ABCA1 cells. L3D-37pA, in contrast, was completely ineffective in competing for the binding of L-37pA. L2D-37pA and apoA-I acted as intermediate competitors; they each reduced the binding of radiolabeled L-37pA to ABCA1 cells by approximately 30% (FIG. 7A). Control cells also showed relatively high specific binding of L-37pA (FIG. 7B), but in the absence of a competitor, the control cells bound 23% less radiolabeled L-37pA peptide than ABCA1 cells (control cells 27±0.6 µmol/mg cell protein; ABCA1 cells 35±2.2 µmol/mg cell protein). Similar to ABCA1 cells, unlabelled L-37pA and D-37pA competed equally well for the binding of radiolabeled L-37pA. In contrast, L2D-37pA and apoA-I were less effective in control cells than in ABCA1 cells for competing for the binding of radiolabeled L-37pA. At the maximum concentration tested, both peptides blocked less than 5% of the radiolabeled L-37pA from binding to control cells, similar to the result obtained with the inactive L3D-37pA peptide. Overall, these results indicate that there is a lack of stereoselectivity in the binding of the 37pA peptide to either ABCA1 cells or control cells and that the cell binding of the peptides is at least partly dependent upon their lipid affinity.

Example 6

Effect of Asymmetry in Lipid Affinity of Multi-Domain Amphipathic Peptides on Lipid Efflux and Cell Cytotoxicity This example demonstrates that asymmetry in lipid affinity of multi-domain amphipathic peptides is an important structural determinant for specificity of ABCA1-dependent cholesterol efflux by multi-domain peptides.

Figure 8:
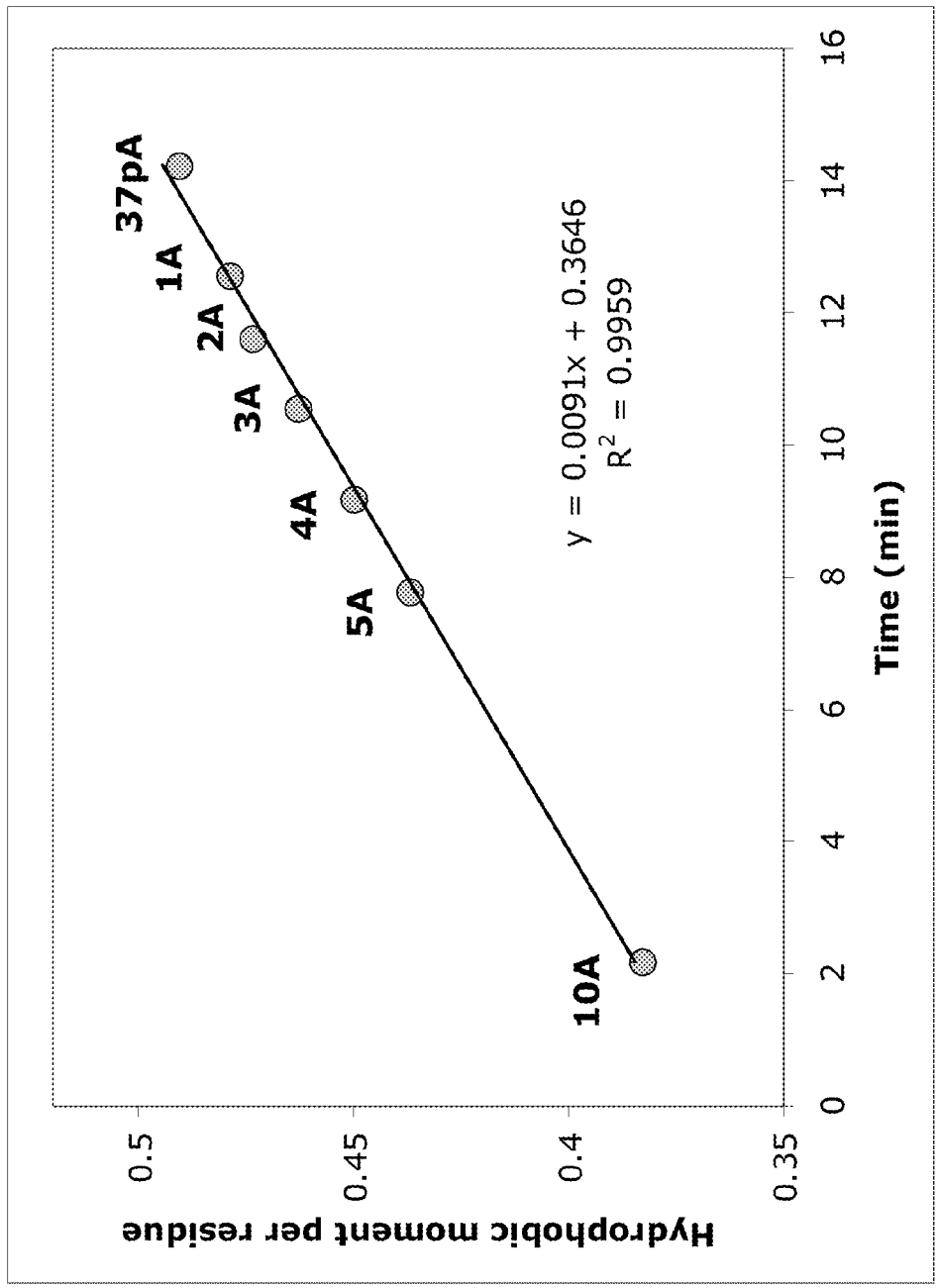
FIG. 8 is a graph plotting the calculated hydrophobic moment of the 37pA peptide and derivative peptides (1A, 2A, 3A, 4A, 5A, and 10A) with their retention time on a reverse phase HPLC. Approximately 1 mg of each of the peptides was injected on a C-18 reverse phase HPLC column and eluted with 25-85% gradient of acetonitrile containing 0.1% TFA.

The 37pA peptide was modified by making 5 Ala substitutions for hydrophobic residues (F18, L14, L3, V10, F6) in either the C-terminal helix (5A) or both helices (10A). Reverse phase HPLC retention times closely correlated with their predicted lipid affinity, as calculated by the hydrophobic moment of the modified peptides (FIG. 8). Four additional peptides with 1 (L14, 1A), 2 (L14, F18, 2A), 3 (L14, F18, F6, 3A) and 4 (L14, F18, F6, V10, 4A) Ala substitutions in the C-terminal helix were also synthesized. The 37pA had the longest retention time and with each additional Ala substitution there was a decrease in lipid affinity based on the retention time (FIG. 8).

Figure 9:
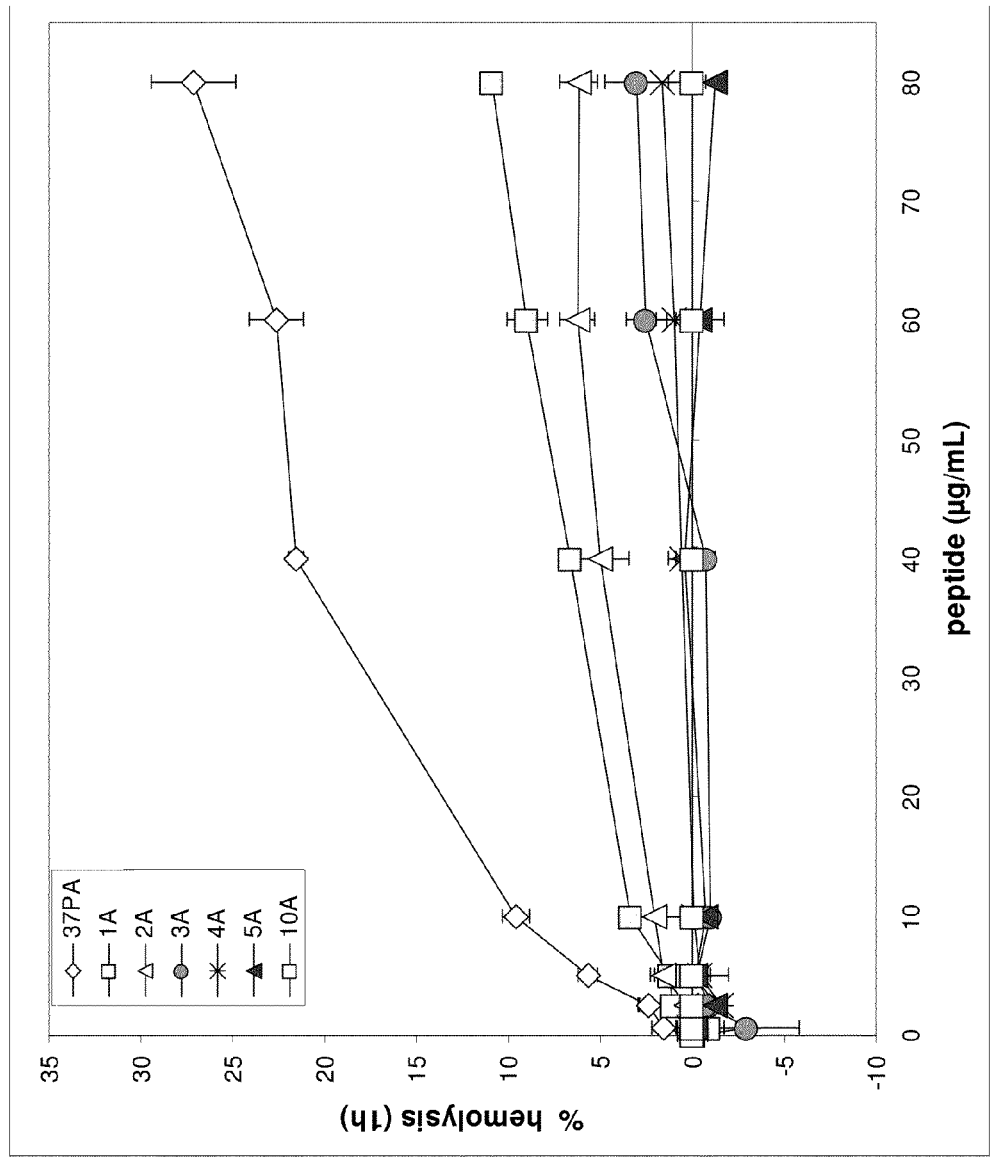
FIG. 9 is a graph illustrating red blood cell lysis by the 37pA peptide and derivative peptides (1A, 2A, 3A, 4A, 5A, and 10A). Red blood cells were incubated with the indicated concentration of the peptides for 1 hour at 37° C. Results are expressed as the mean of triplicates ±1 SD.

The 37pA peptide and all of the modified peptides were then tested for cytotoxicity, using a red blood cell hemolysis assay (FIG. 9). Similar to results previously observed via monitoring LDH release, the 37pA was found to be cytotoxic. Approximately 25% of the red blood cells were lysed after 1 hour at the maximum dose tested (FIG. 9). Overall, the modified peptides containing the Ala substitutions were less cytotoxic, and the degree of cytotoxicity closely correlated with the number of Ala substitutions. The 4A, and 5A peptides showed no appreciable hemolysis of the red blood cells, whereas the 1A, 2A and 3A peptides showed a moderate degree of hemolysis when compared to 37pA (FIG. 9). Based on these results, the optimum hydrophobic moment score per residue for the amphipathic α-helix with relatively low lipid affinity, in terms of reducing cytotoxicity, is less than about 0.34 (Eisenberg et al., *PNAS* 81:140-144, 1984 and Eisenberg et al., *J. Mol. Biol.* 179:125-142, 1984).

Figure 10:
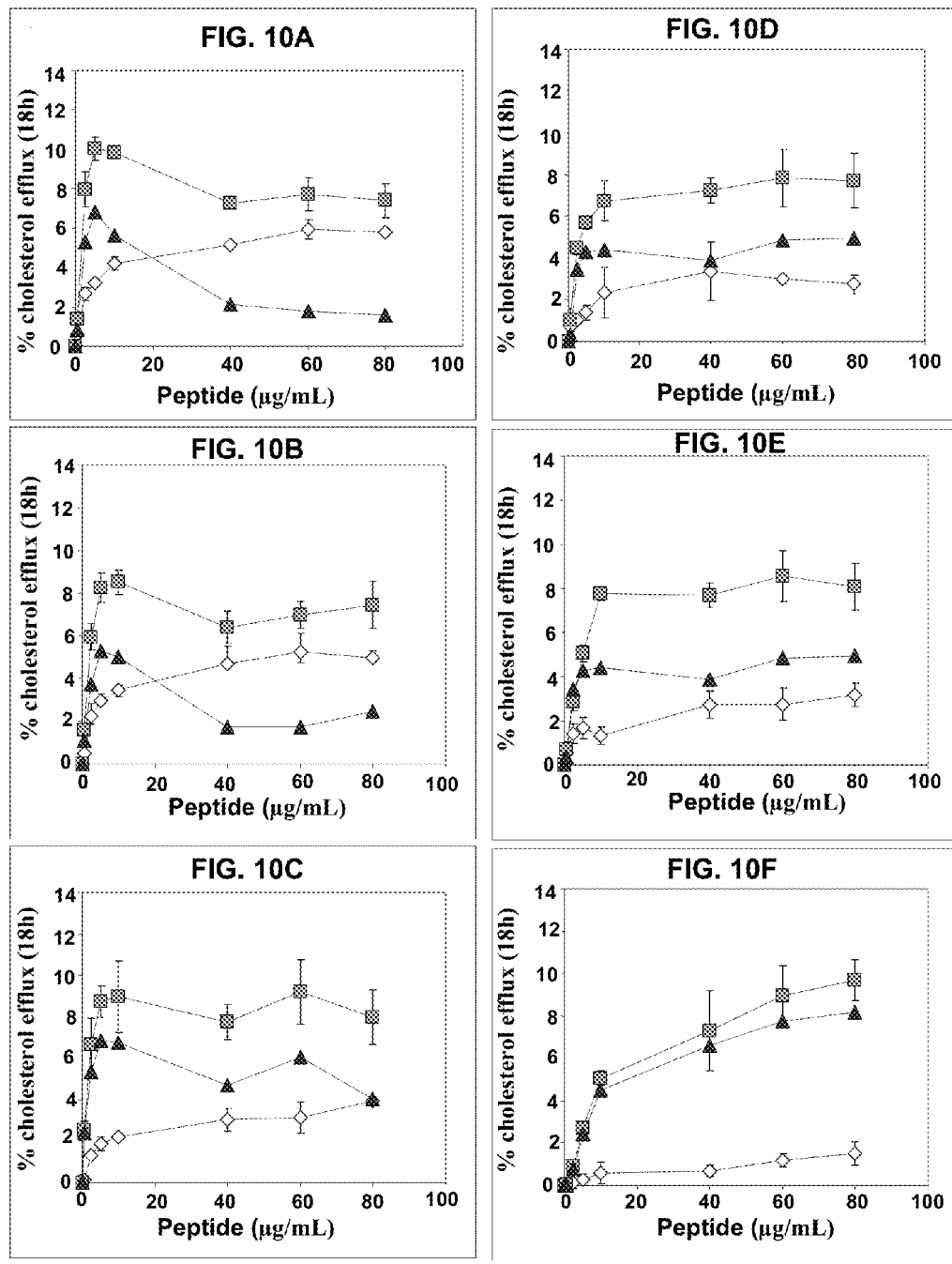
FIGS. 10A-10F are a set of graphs illustrating cholesterol efflux by ABCA1 transfected cells and control cells when treated with the 37pA peptide and derivative peptides (37pA, FIG. 10A; 1A, FIG. 10B; 2A, FIG. 10C; 3A, FIG. 10D; 4A, FIG. 10E; and 5A, FIG. 10F). ABCA1 transfected cells (grey squares) and control cells (solid triangles) were examined for their ability to efflux cholesterol over an 18 hour period when treated with the indicated concentration of peptide. ABCA1-specific efflux was calculated by subtracting the cholesterol efflux results from the ABCA1 transfected cells from the control cells (open diamonds). Results are expressed as the mean of triplicates ±1 SD.

The 37pA peptide and the modified peptides were also tested for their specificity for cholesterol efflux by the ABCA1 transporter (FIG. 10). The 37pA peptide promoted ABCA1-mediated cholesterol efflux, but it was also able to mediate cholesterol efflux from a control HeLa cell line that does not express the ABCA1 transporter. When cholesterol efflux was performed with the modified peptides, they were observed to have two different features than the 37pA peptide. First, there was a progressive rightward shift in the dose response curve with the Ala substitutions compared to the 37pA peptide. A greater concentration of the modified peptides was needed to get the maximum amount of cholesterol efflux. In addition, the percent of total cholesterol efflux attributable to the ABCA1 transporter progressively increased by making the Ala substitutions in the 37pA peptide. Without wishing to be bound by theory, it is believed that this is due to the fact that the modified peptides still retained their ability to remove cholesterol from the ABCA1-transfected cells, but were less effective in removing cholesterol from the control cells via non-ABCA1 cholesterol efflux pathways. The 5A peptide was completely specific for only causing cholesterol efflux by the ABCA1 transporter. Based on these results, the optimum hydrophobic moment score (Eisenberg scale; 100 degree-alpha helix) per residue for the amphipathic helix with relatively low lipid affinity, in terms of ABCA1-specificity for cholesterol efflux, is between about 0.1 and about 0.33.

Example 7

Identification of Non-Cytotoxic Peptides that Promote Abca1-Dependent Lipid Efflux This example illustrates a method for identifying non-cytotoxic peptides that promote ABCA1-dependent lipid efflux from cells.

Peptide Design:

Based on the principals and procedures described in the present application, an amino acid sequence can be designed for a multi-domain peptide that contains two or more amphipathic α-helices, one with relatively high lipid affinity and one with relatively low lipid affinity.

Peptide Production:

Peptides to be tested can be produced synthetically or by recombinant DNA methods, as described in the present application, and purified by reverse phase HPLC or other suitable techniques well known to one of skill in the art.

Peptide Cytotoxicity Testing:

Peptides can be tested for cytotoxicity by any number of methods well known to one of skill in the art, such as the release of intracellular LDH (Example 4) or the release of hemoglobin from red blood cells (Example 6). Such studies are performed by incubating various concentrations of the peptides with a cell line, a vesicle or red blood cells, as described herein.

Peptide ABCA1-Specificity for Lipid Efflux:

Peptides to be tested can be added to serum-free cell culture media in the approximate concentration range of 1-20 micromolar and incubated with a control cell line that does not express the ABCA1 transporter and the same cell line after transfection with human cDNA for the ABCA1 transporter, as described herein. Alternatively, cells, such as macrophages, that either express or do not express the ABCA1 transporter depending on their cholesterol content and/or exposure to agents that induce the ABCA1 transporter (e.g., cAMP and LXR agonists) can also be used. After a suitable period of approximately 4 to 24 hours, the conditioned media can be removed from the cells and the amount of cholesterol and or phospholipid effluxed can be quantified, as described herein. ABCA1-specific lipid efflux is calculated by subtracting the total lipid efflux from the ABCA1 expressing cell line from the results obtained from the cell line that does not express the ABCA1 transporter.

Example 8

In Vivo Effects of 5A-Peptide in Mice

This example illustrates the in vivo effects of 5A-POPC (1-palmitoyl-2-oleoyl-sn-phosphatidylcholine) peptide in mice.

The 5A peptide (SEQ ID NO: 3) was complexed with POPC at a 1:7 molar ratio using a co-lyophilization procedure by which the free peptide and POPC were co-dissolved in glacial acetic acid and lyophilized. The dry powder was reconstituted with saline and heated between 37° C. to 50° C. to reconstitution, which results in a clear solution of particles containing both the 5A peptide and POPC.

Figure 11:
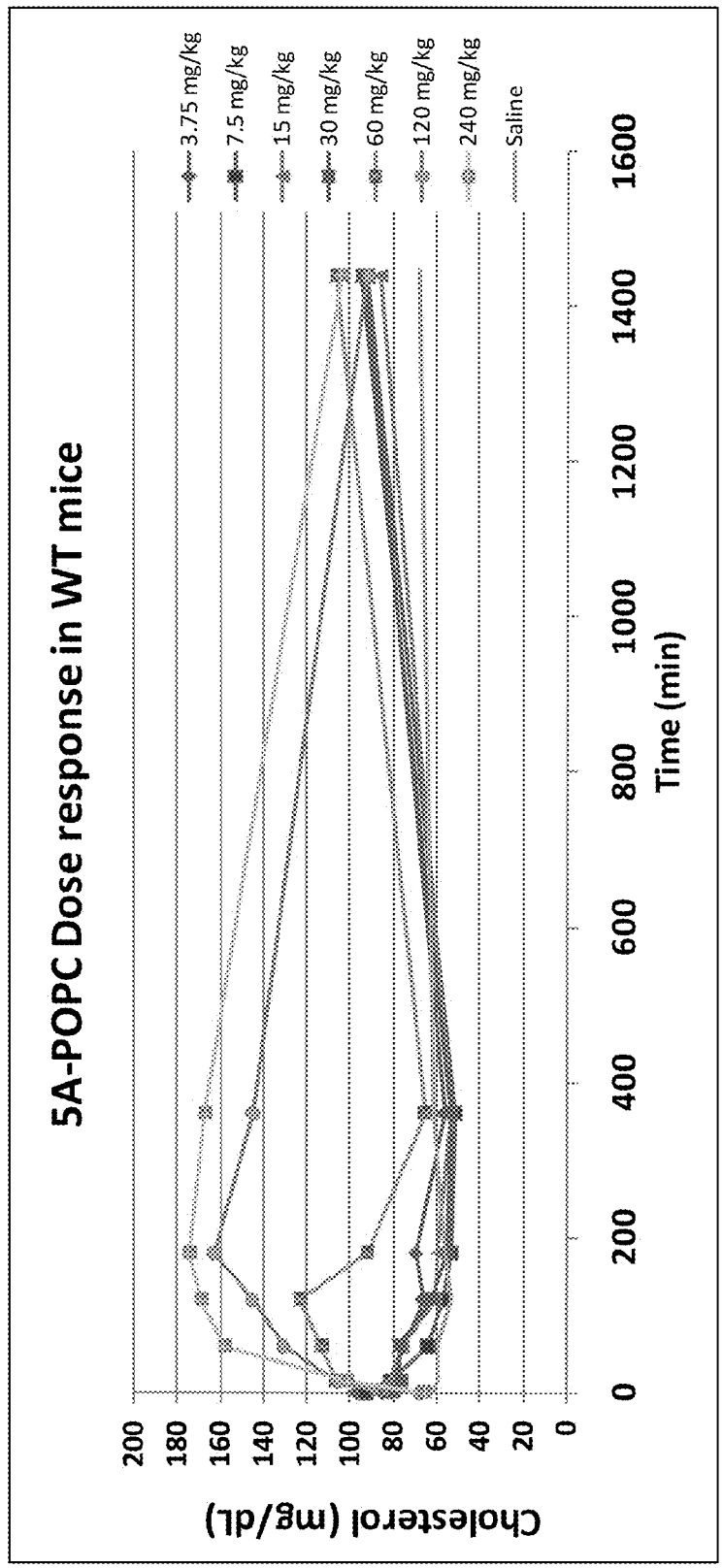
FIG. 11 is a graph illustrating 5A-POPC (1-palmitoyl-2-oleoyl phosphatidylcholine peptide-mediated alterations in plasma cholesterol after IV infusion of increasing doses of 5A peptide in wild-type mice over 24 hours. Increasing doses of the peptide resulted in increased plasma HDL as result of ABCA-1 mediated efflux.

Increasing concentrations (3.75 mg/kg; 7.5 mg/kg; 15 mg/kg; 30 mg/kg; 60 mg/kg; 120 mg/kg; or 240 mg/kg) of 5A-POPC peptide were administered intravenously to wild-type mice over a 24 hour period. Plasma cholesterol levels were then measured. As illustrated in FIG. 11, a dose response relationship between total cholesterol and the 5A peptide was observed. Based on fast protein liquid chromatography (FPLC) analysis, almost all of this increase in cholesterol was due to an increase in the cholesterol content of HDL, which is consistent with the ability of the peptide to in vitro promote cholesterol efflux from cells.

Figure 12:
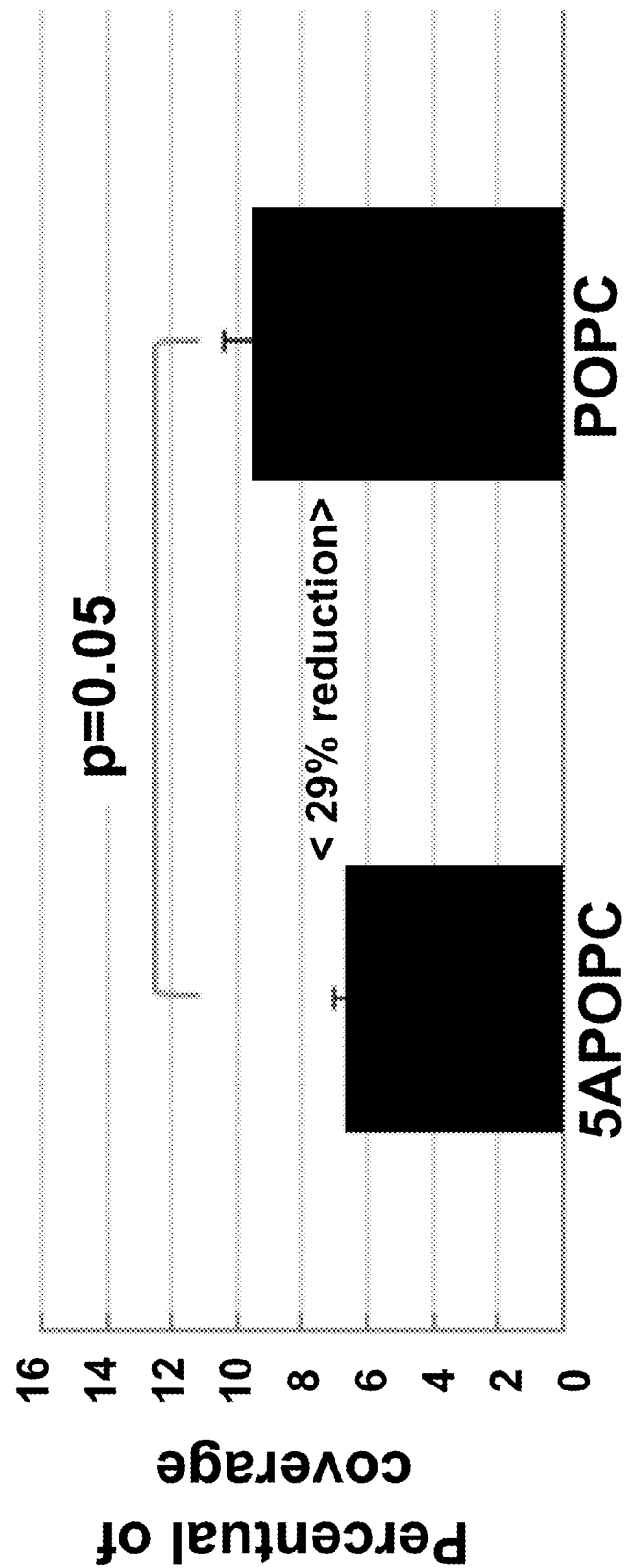
FIG. 12 is a graph illustrating atherosclerosis measurement in ApoE KO mice treated for 12 weeks with 5A peptide versus POPC control. A significant difference of 29% was observed in female mice that received 30 mg/kg of peptide. This dose showed only modest changes in cholesterol efflux to plasma (see FIG. 11), suggesting that higher doses of the peptide could lead to further reduction and possibly regression of plaques.
Figure 13:
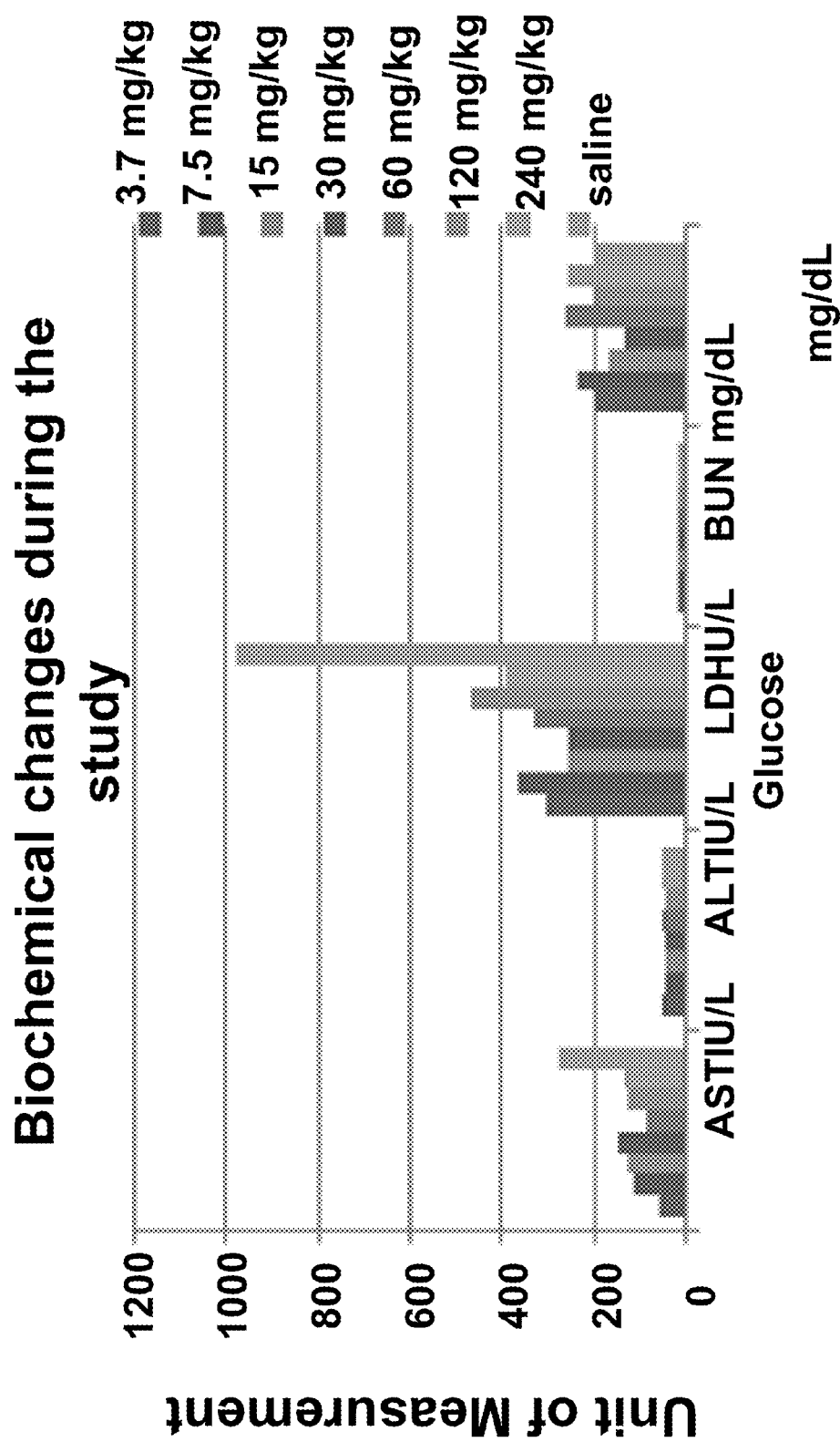
FIG. 13 is a series of graphs illustrating changes in liver enzymes, hemolytic parameter, kidney function and glucose levels in wild-type mice receiving increasing doses of the 5A peptide. No significant changes were observed in the measured parameters, including weight during the study. Some of the parameters did show improvement compared to control and baseline.
Figure 14:
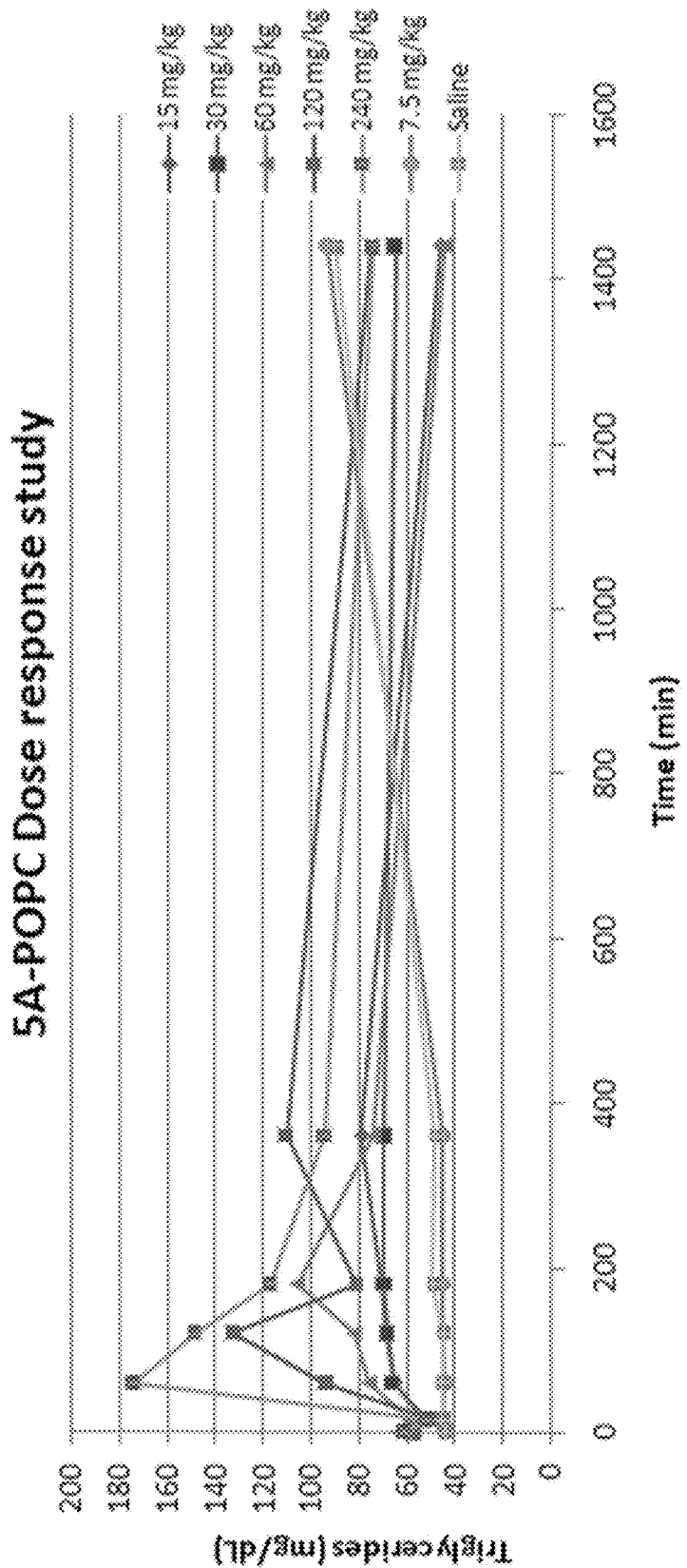
FIG. 14 is a graph illustrating the change in plasma triglycerides after intravenous (IV) infusion of increasing doses of 5A-POPC peptide over 24 hours, after over night fasting in wild-type mice. The increasing doses of the 5A-POPC peptide led to a proportional increase in triglyceride levels, up to 3 fold the baseline value. This effect has also been observed after the injection of the native ApoA-I lipoprotein.
Figure 15:
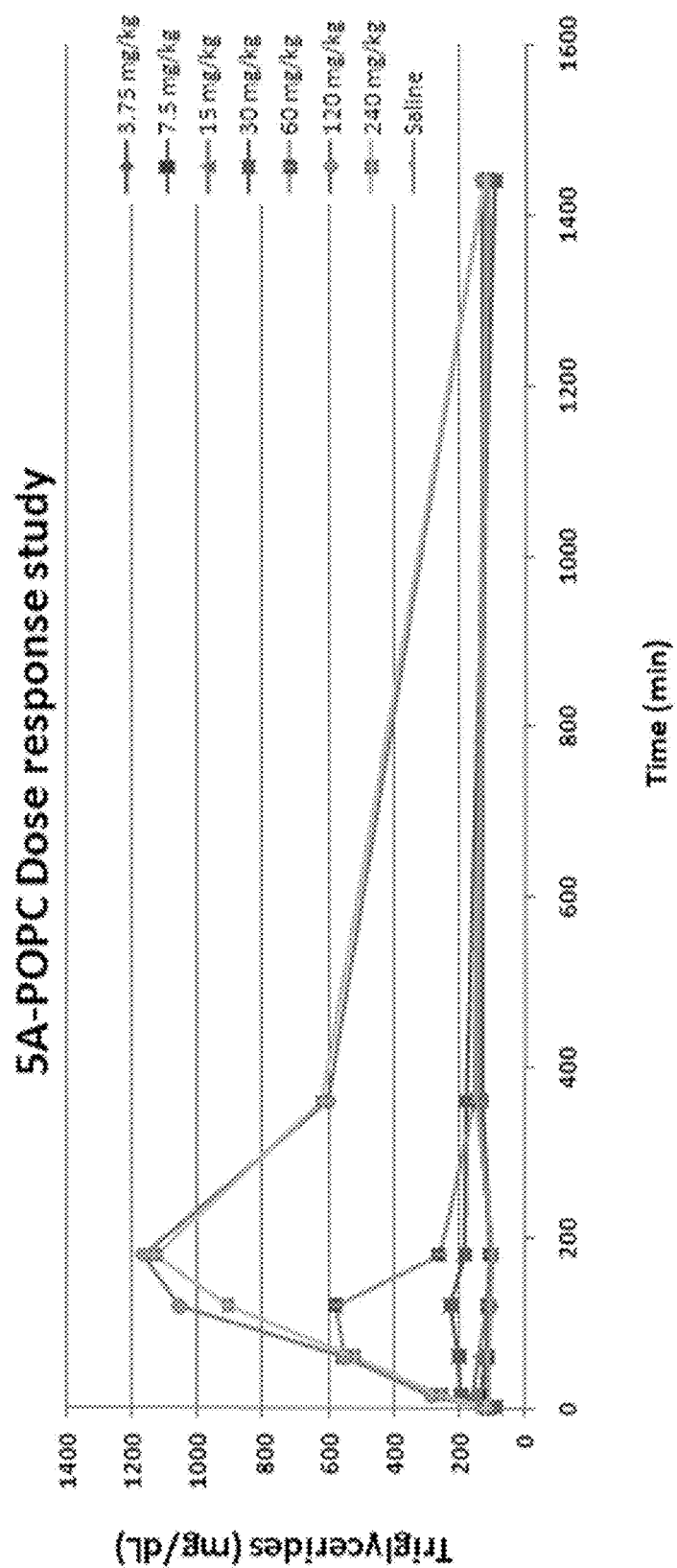
FIG. 15 is a graph illustrating the change in plasma triglycerides after IV infusion of increasing doses of 5A-POPC peptide over 24 hours, in non-fasting mice. Unlike a maximal 3 fold increase in plasma triglycerides, when mice were not fasting an increase of up to 20 times was observed. No signs of toxicity were observed in mice receiving up to 240 mg/kg of peptide during the study.

As illustrated in FIG. 12, treatment of mice with the 5A peptide (SEQ ID NO: 3) reduced atherosclerosis. Treatment with the 5A peptide also appeared to be non-toxic based on measurement of various serum biomarkers (FIG. 13). However, 5A peptide caused a transient increase in triglycerides (FIGS. 14 and 15). Similar effects on triglycerides have also been measured for apoA-I and various apoA-I mimetic peptides.

Hypertriglyceridemia is a side effect of various drugs and can be due to liver toxicity, but it often occurs after chronic administration of the drug and is persistent. In this case, the hypertriglyceridemia occurred almost immediately after administration of the peptide and was transient (less than 8 hours) and there was no evidence of increased markers of liver damage (FIG. 13). FPLC analysis indicated that the increase in triglycerides occurred on VLDL, which may be a consequence of the ability of the 5A peptide to induce reverse cholesterol transport back to the liver and stimulate VLDL secretion.

Figure 16:
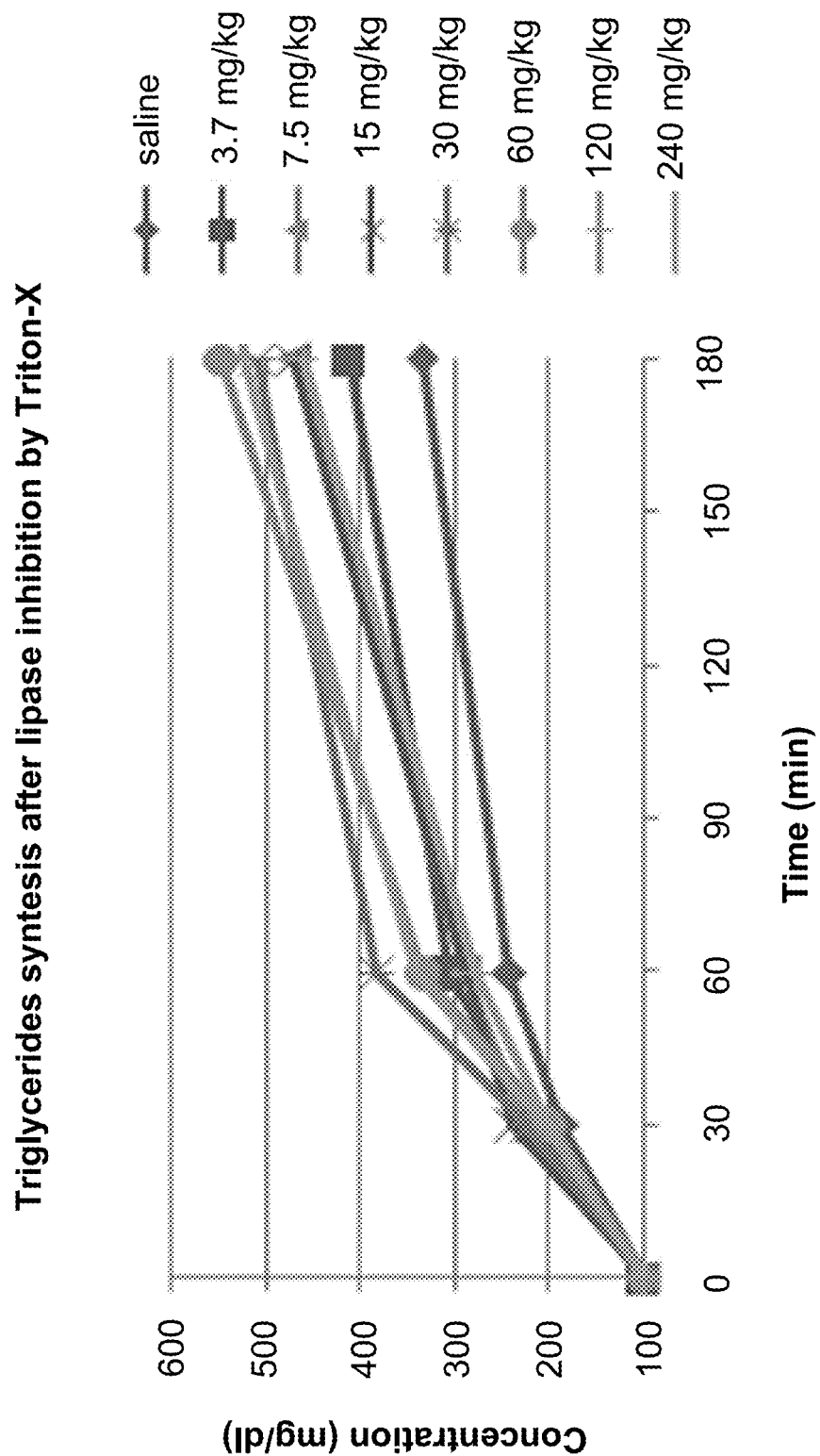
FIG. 16 is a graph illustrating triglyceride synthesis in mice after lipase inhibition by Triton-WR 1339. Increasing doses of the 5A peptide led to no significant changes in triglycerides synthesis suggesting that the hypertriglyceridemia observed after 5A injection resulted from decreased catabolism of ApoB-containing lipoproteins.

Additional studies (see FIGS. 16 and 17) indicated that the increase in triglycerides was due to inhibition of lipoprotein lipase, the main serum enzyme that hydrolyzes triglycerides on VLDL and chylomicrons. First, as illustrated in FIG. 15, the increase in triglycerides was significant in non-fasting mice (i.e., over a 10-fold increase was observed and the reactant level of serum triglycerides exceeded 1000 mg/dL). In contrast, triglyceride levels in fasting mice were only increased by 3-fold (FIG. 14). As illustrated in FIG. 16, increasing doses of the 5A peptide led to no significant changes in triglycerides synthesis in mice treated with Triton-WR 1339 (a detergent that inhibits lipoprotein lipase). These studies suggest that the hypertriglyceridemia observed after 5A injection resulted from decreased catabolism of apoB-containing lipoproteins.

Figure 17:
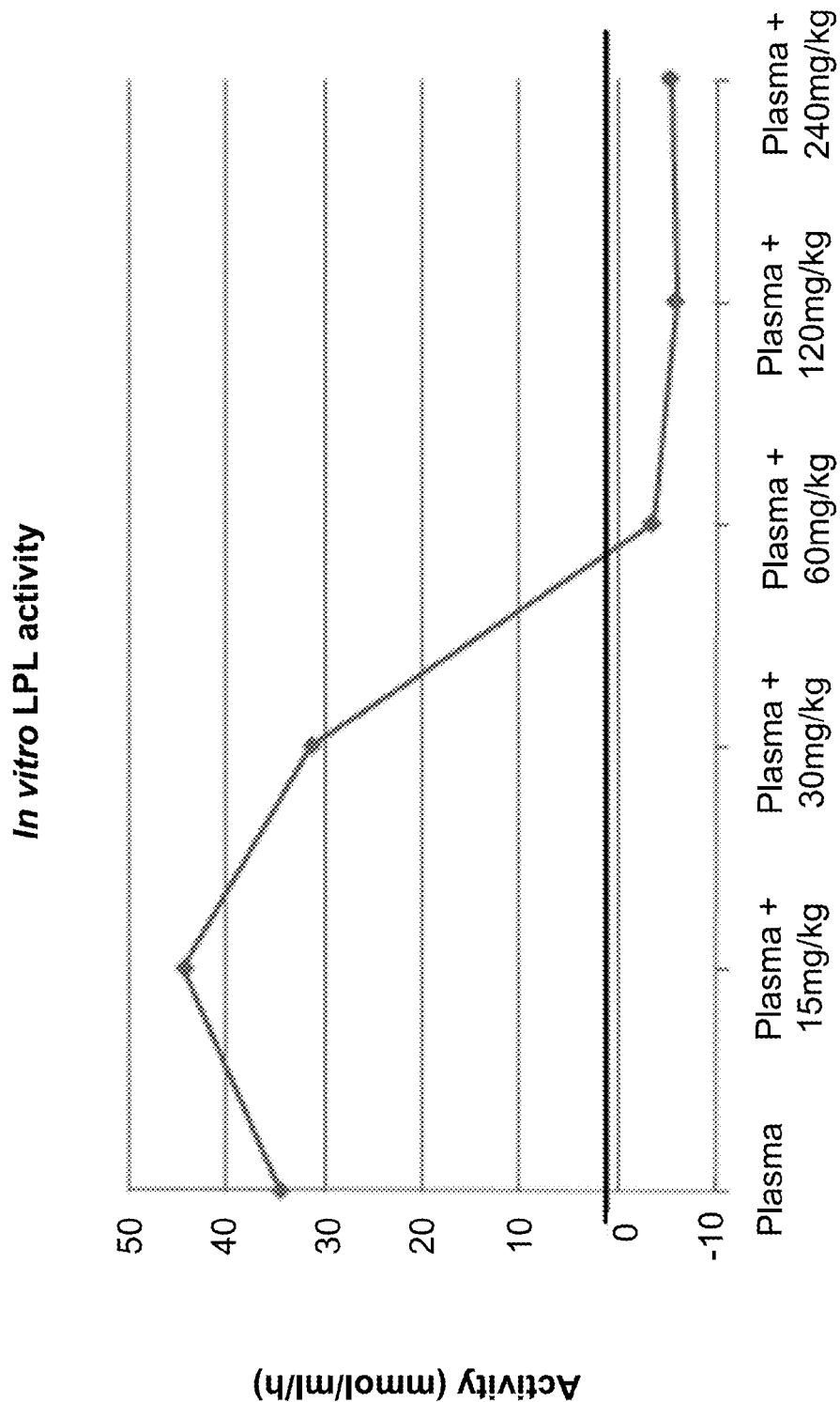
FIG. 17 is a graph illustrating in vitro activity of lipoprotein lipase at increasing doses of 5A peptide. Compared to baseline, the activity of LPL decreased dramatically as the concentration of 5A-POPC peptide increased.

In the saline treated mice, there was a time dependent increase in triglycerides. When the mice were also treated with the 5A peptide there was also an increase in triglycerides but compared to mice not treated with Triton-X (FIGS. 14 and 15), the increase over the saline control was not as large and was not statistically significant. This would be expected if both the 5A peptide and Triton-X inhibit lipoprotein lipase. In FIG. 17, the direct effect of the 5A peptide was tested on lipoprotein lipase, using an in vitro assay. Using doses similar to those which caused hypertriglyceridemia in mice, it was found that the 5A peptide was a potent inhibitor of lipoprotein lipase revealing the mechanism by which 5A peptide caused hypertriglyceridemia.

These studies demonstrate that while 5A-POPC peptide stimulates cholesterol efflux in mice in vivo, it also inhibits lipoprotein lipase leading to transient hypertriglyceridemia. These studies also reveal a new use of the 5A peptide as a lipoprotein lipase inhibitor.

Example 9

In Vivo Effects of 18A-C-II Peptide in Mice

This example illustrates the ability of 18A-C-II peptide to reduce triglycerides and cholesterol plasma levels in normal and dyslipidemic mice.

18A-C-II peptide (SEQ ID NO: 70) was complexed with POPC at a 1:7 molar ratio using a co-lyophilization procedure by which the free peptide and POPC were co-dissolved in glacial acetic acid and lyophilized. The dry powder was reconstituted with saline and heated between 37° C. to 50° C. to reconstitution, which results in a clear solution of particles containing both the 18A-C-II peptide and POPC.

Figure 18:
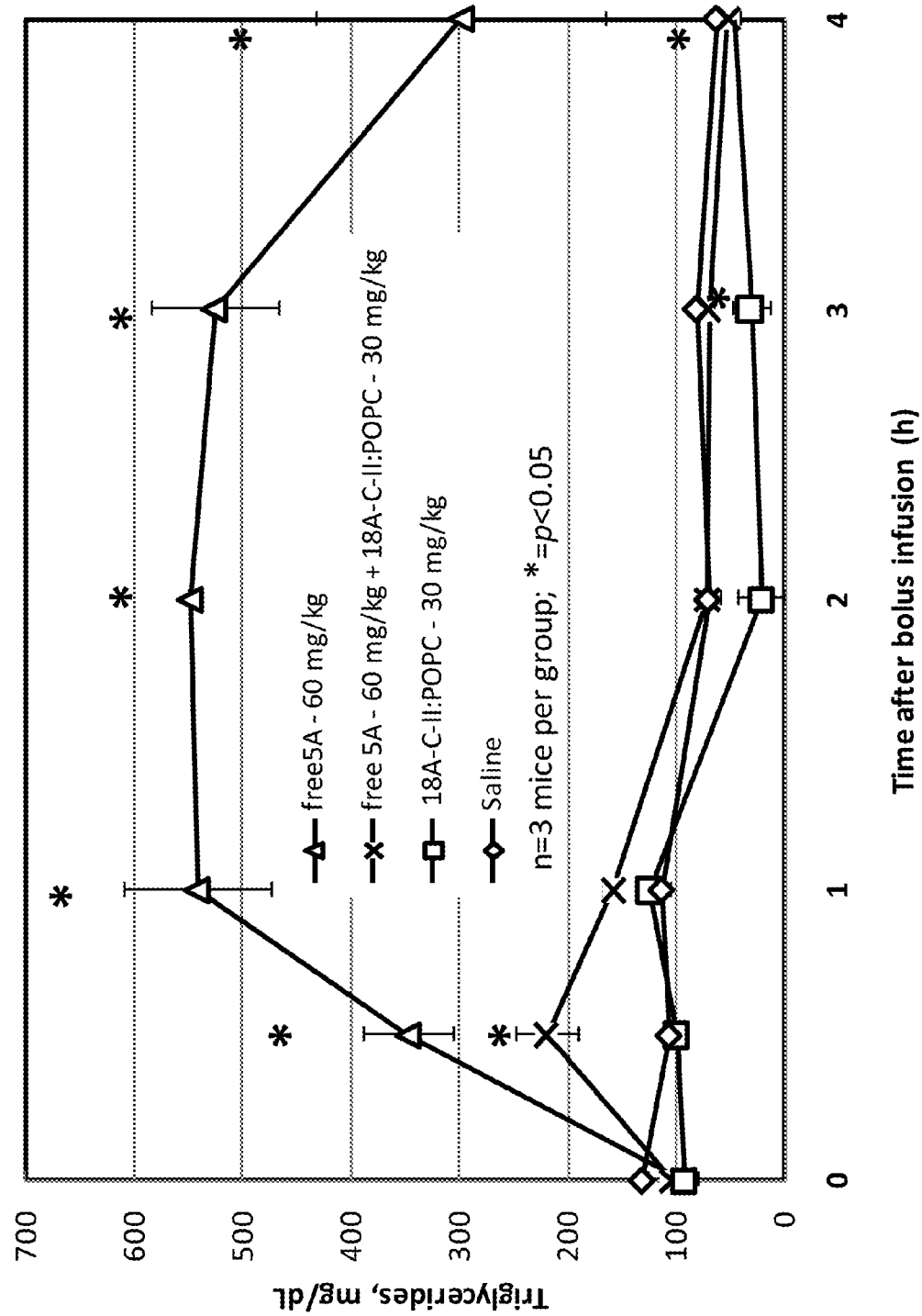
FIG. 18 is a graph illustrating the ability of 18A-C-II: POPC peptide (peptide with SEQ ID NO: 70) to prevent hypertriglyceridemia. The 18A-C-II:POPC peptide was lipidated with POPC at the ratio of 1:7. Hypertriglyceridemia was induced in C57B1/6 mice by a 2 mg (60 mg/kg) bolus intravenous (IV) injection of free 5A peptide (Δ). When 1 mg (30 mg/kg) of the 18A-C-II peptide was co-injected with free 5A peptide (X), the increase in plasma triglycerides was significantly halted. In addition, a single IV dose of 1 mg of the 18A-C-II:POPC peptide lowered the plasma triglyceride levels in normal C57B1 mice (□) compared to saline (◊).
Figure 19:
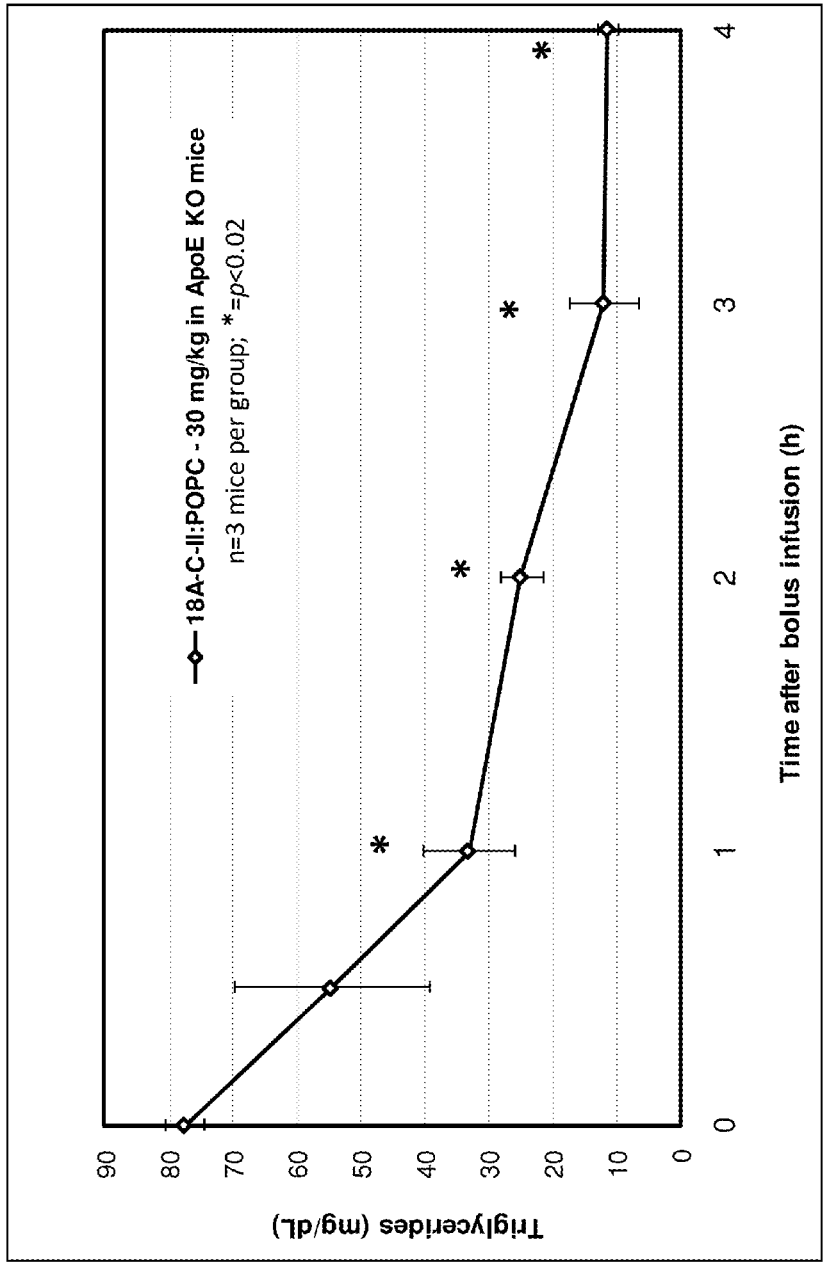
FIG. 19 is a graph illustrating the effect of 18A-C-II:POPC (1:7) peptide on triglycerides of ApoE knockout mice. A single dose of 30 mg/kg (1 mg) of 18A-C-II:POPC peptide significantly reduced plasma triglyceride levels in apoE KO mice (76%) when compared to baseline values.

Hypertriglyceridemia was induced in C57B1/6 mice by a 2 mg (60 mg/kg) bolus IV injection of free 5A peptide (A). As illustrated in FIG. 18, when 1 mg (30 mg/kg) of the 18A-C-II peptide was co-injected with free 5A peptide (X), the increase in plasma triglycerides was significantly reduced. In addition, a single IV dose of 1 mg of the 18A-C-II:POPC peptide lowered the plasma triglyceride levels in normal C57B1 mice (□) compared to saline (◇). Additionally, a single dose of 30 mg/kg (1 mg) of 18A-C-II:POPC peptide significantly reduced plasma triglyceride levels in ApoE knockout mice (76%) when compared to baseline values (see FIG. 19).

Figure 20:
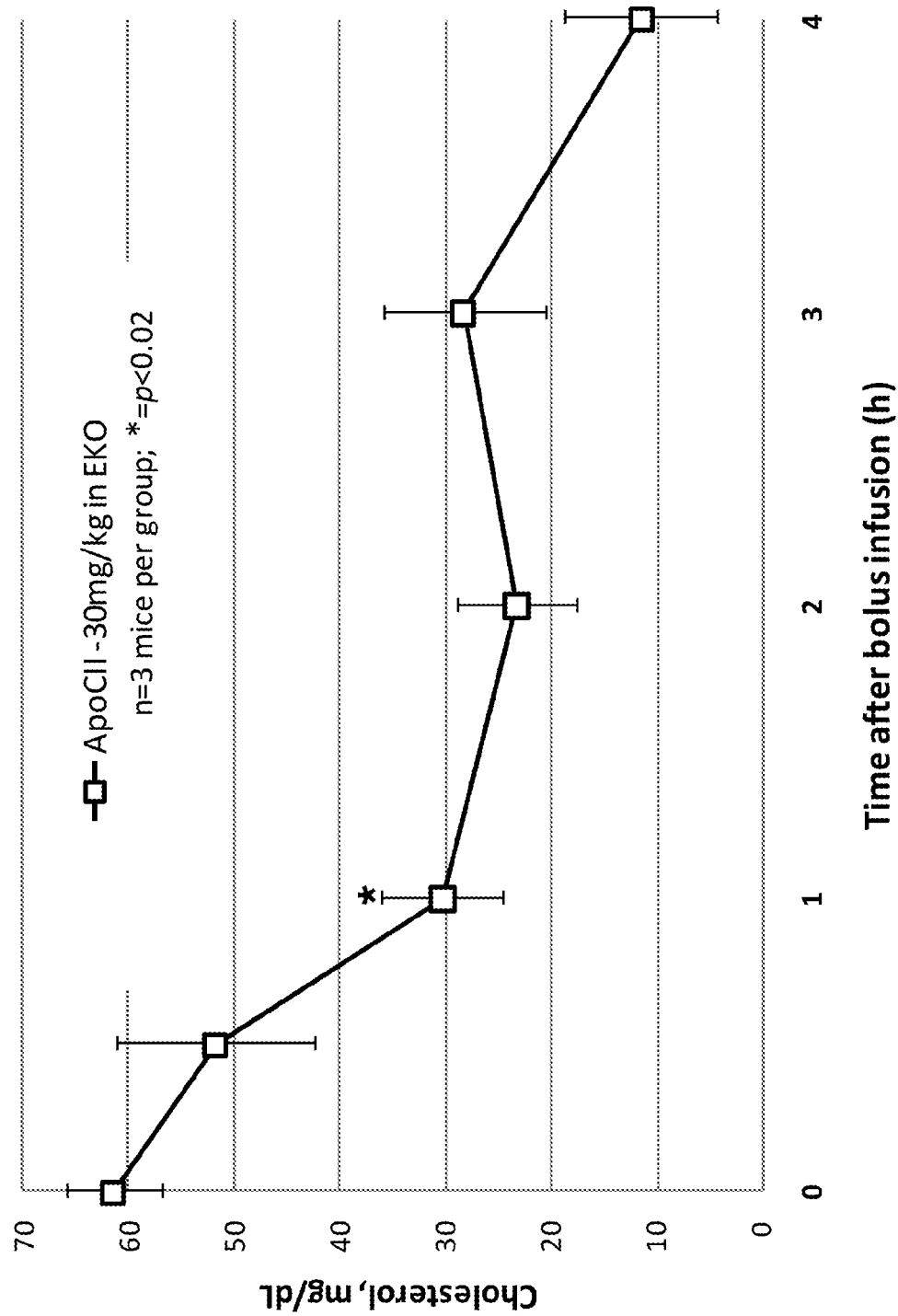
FIG. 20 is a graph illustrating the effect of 18A-C-II peptide on plasma cholesterol in ApoE KO mice. In order to investigate the effects of the 18A-C-II peptide in plasma cholesterol of C57B1/6 mice, mice were injected with an IV bolus of 1 mg (30 mg/kg) of 18A-C-II:POPC and plasma cholesterol levels were monitored for 4 hours. A significant reduction of 52% and 80% was observed after 1 hour and 4 hours.

In order to investigate the effects of the 18A-C-II peptide in plasma cholesterol of C57B1/6 mice, mice were injected with an IV bolus of 1 mg (30 mg/kg) of 18A-C-II:POPC and plasma cholesterol levels were monitored for 4 hours. As illustrated in FIG. 20, a significant reduction in plasma cholesterol of 52% and 80% was observed after 1 hour and 4 hours of the treatment.

Figure 21:
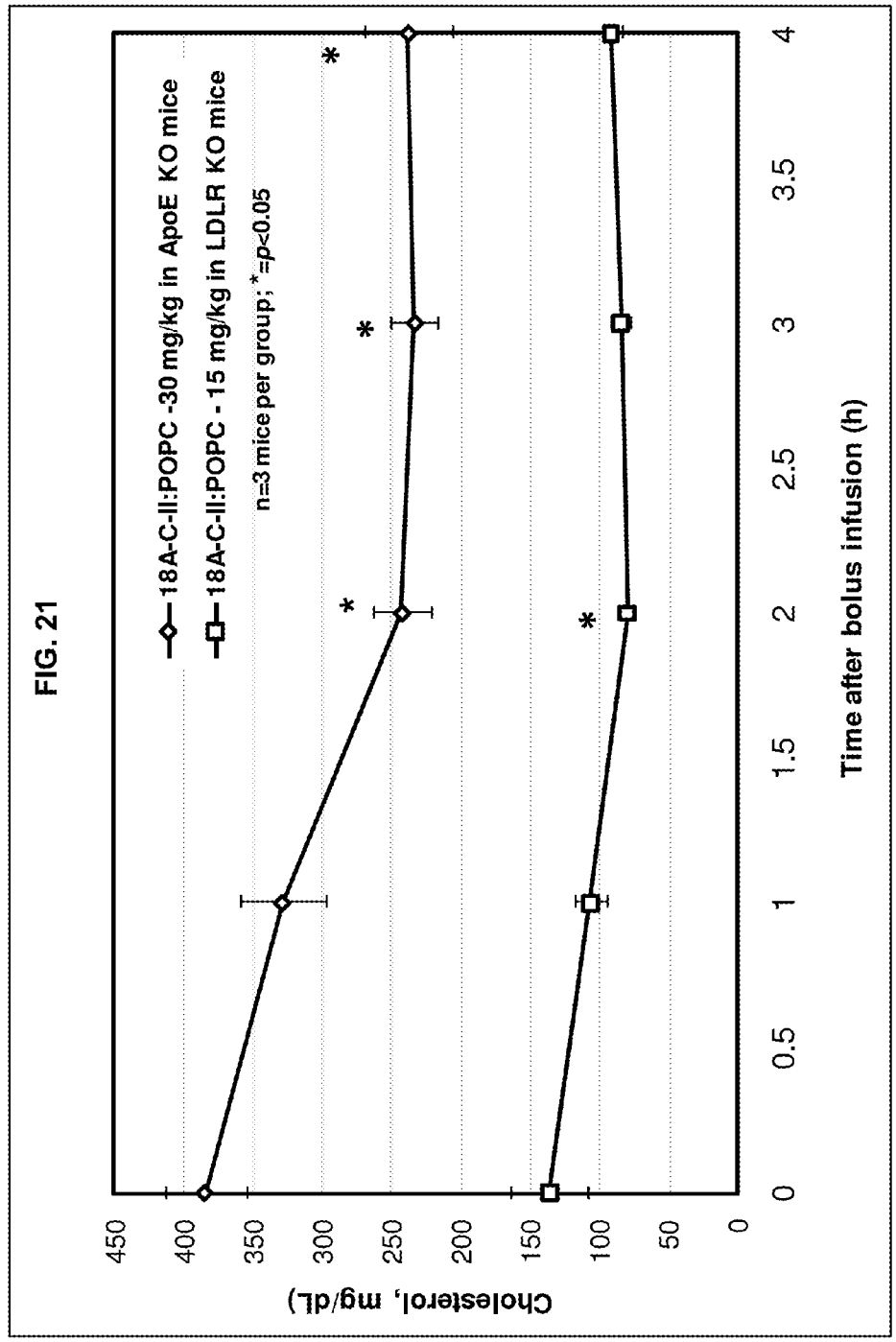
FIG. 21 is a graph illustrating the effect of 18A-C-II peptide on plasma cholesterol. ApoE knockout and LDLR knockout mice are characterized by high plasma levels of VLDL/IDL and LDL respectively. To evaluate the potential to reduce the plasma cholesterol levels, mice were injected IV in bolus with a dose of 1 mg (30 mg/kg) of the lipidated 18A-C-II: POPC in ApoE KO (◊) and 0.5 mg (15 mg/kg) in LDLR KO mice (□). A significant reduction (36%) in serum cholesterol in ApoE KO mice was observed, while the low dose of the peptide in LDLR KO mice showed a reduction of 22% in plasma cholesterol after 2 hours of the treatment.

ApoE knockout and LDLR knockout mice are characterized by high plasma levels of VLDL/IDL and LDL respectively. To evaluate the potential to reduce the plasma cholesterol levels, mice were injected IV in bolus with a dose of 1 mg (30 mg/kg) of the lipidated 18A-C-II:POPC in ApoE KO (◇) and 0.5 mg (15 mg/kg) in LDLR KO mice (□). As shown in FIG. 21, a significant reduction (36%) in serum cholesterol in ApoE KO mice was observed, while the low dose of the peptide in LDLR KO mice showed a reduction of 22% in plasma cholesterol after 2 hours of the treatment.

Figure 22A:
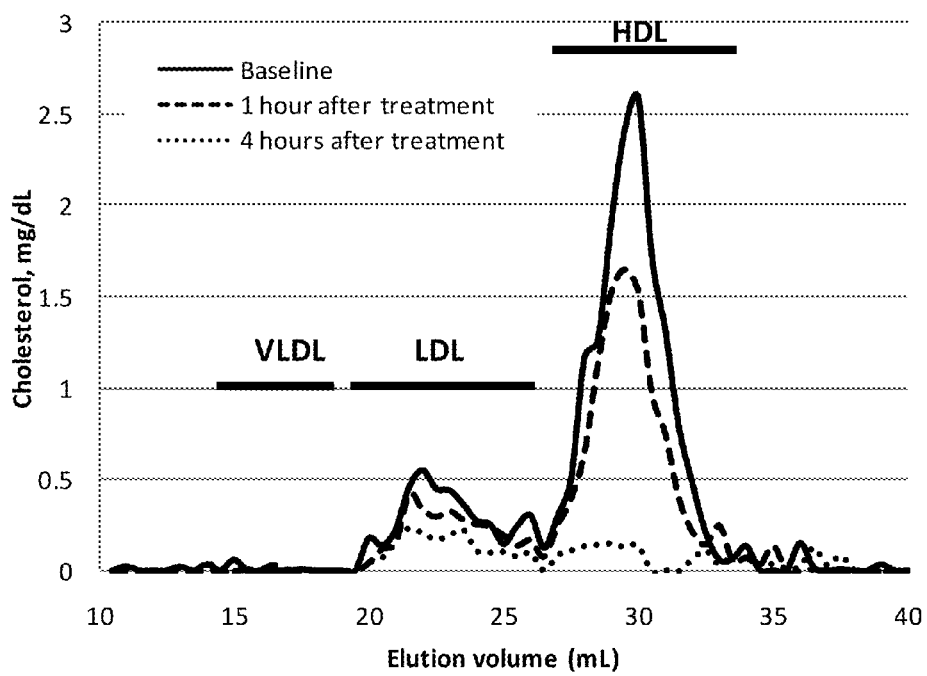
FIGS. 22A-22B are graphs illustrating the effect of 18A-C-II peptide on plasma lipoproteins. The changes observed on plasma cholesterol and triglycerides were further analyzed by fast protein liquid chromatography (FPLC). A dose of 30 mg/kg of 18A-C-II:POPC (1:7) peptide lead to reduction of LDL-c, HDL-c (left panel) as well as VLDL-tg, LDL-tg and HDL-tg (right panel) at one and four hours after treatment. (LDL-c=LDL cholesterol; tg=triglycerides). Each sample represents a pool of 3 mice.
Figure 22B:
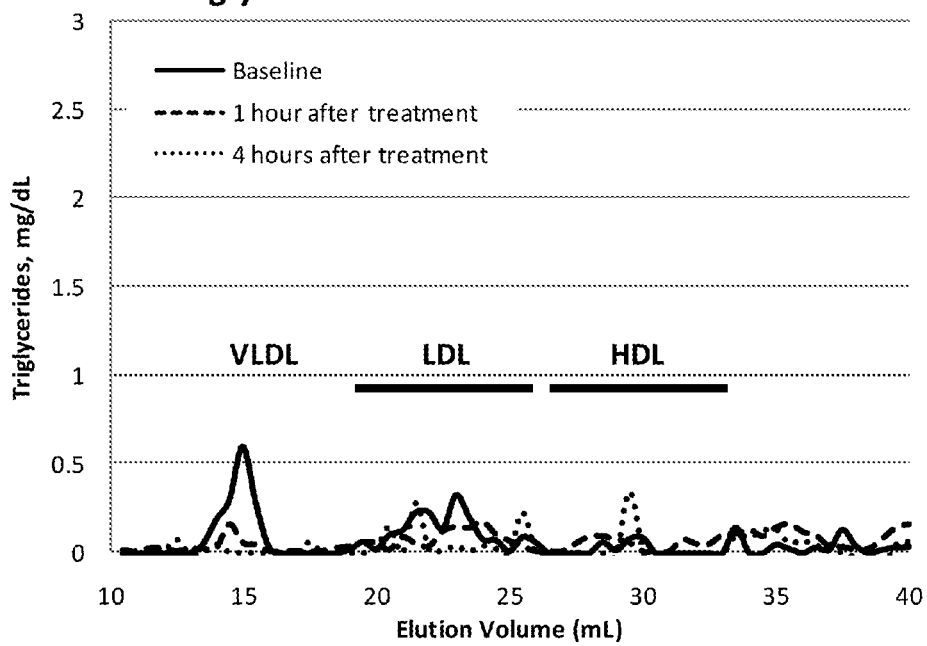

The changes observed in plasma cholesterol and triglycerides were further analyzed by fast protein liquid chromatography (FPLC). As illustrated in FIG. 22, a dose of 30 mg/kg of 18A-C-II:POPC (1:7) peptide lead to reduction of LDL-c, HDL-c (left panel) as well as VLDL-tg, LDL-tg and HDL-tg (right panel) at 1 and 4 hours after treatment. (LDL-c=LDL cholesterol; tg=triglycerides). Each sample represents a pool of 3 mice.

Figure 23:
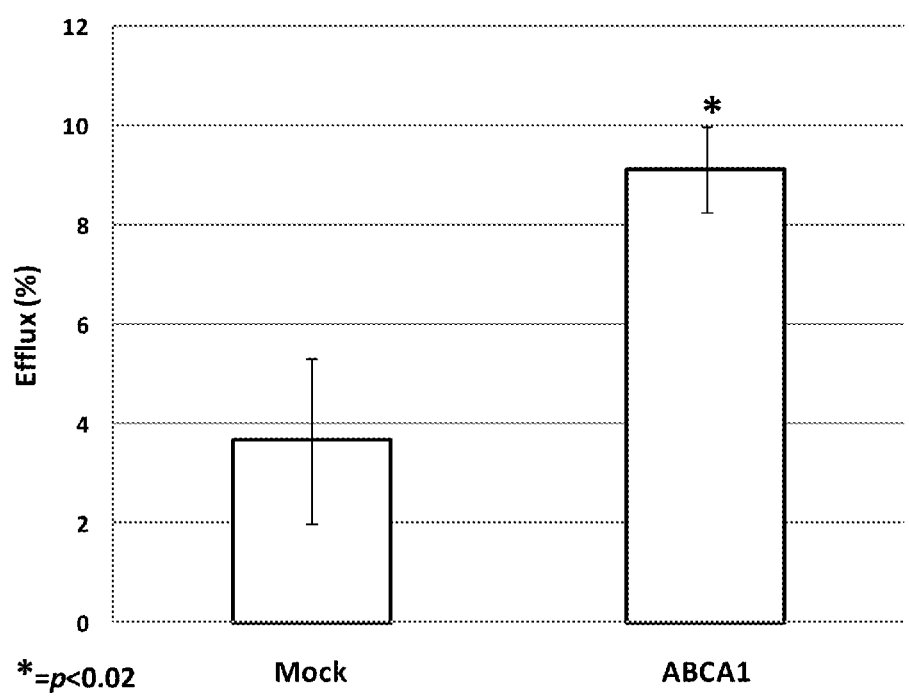
FIG. 23 is a graph illustrating the effect of 18A-C-II peptide on cholesterol efflux. BHK and BHK-ABCA1 cells were loaded with $^3$H-cholesterol for 24 hours at 37° C. and then 20 ug/ml of the free 18A-C-II peptide was added as cholesterol acceptor to efflux for 18 hours. Percentage efflux was calculated by subtracting the radioactive counts in the blank from the radioactive counts in the presence of an acceptor and then dividing the result by the sum of the radioactive counts in the medium plus the cell fraction. A significant difference was observed on cells that express the ABCA1 transporter indicating that ABCA1 is, at least, one mechanism mediating the cholesterol efflux to the 18A-C-II peptide.

The effect of 18A-C-II peptide on cholesterol efflux was investigated by loading BHK and BHK-ABCA1 cells with $^3$H-cholesterol for 24 hours at 37° C. and then adding 20 ug/ml of the free 18A-C-II peptide as cholesterol acceptor to efflux for 18 hours. Percentage efflux was calculated by subtracting the radioactive counts in the blank from the radioactive counts in the presence of an acceptor and then dividing the result by the sum of the radioactive counts in the medium plus the cell fraction. As shown in FIG. 23, a significant difference was observed in cells that express the ABCA1 transporter indicating that ABCA1 is, at least, one mechanism mediating the cholesterol efflux to the 18A-C-II peptide.

These studies show that the 18A-C-II peptide produces plasma changes in triglycerides similar to the native human protein. The 18A-C-II peptide was able to reduce and to prevent the increase of triglycerides in plasma of normal and dyslipidemic mice. The 18A-C-II peptide was also able to reduce plasma cholesterol levels in normal and dyslipidemic mice. The reduction of cholesterol and triglycerides was seen in all lipoproteins. The efflux mediated by the 18A-C-II peptide is, at least, in part mediated by the ABCA-1 transporter. Altogether, the reduced triglycerides and cholesterol plasma levels observed is compatible to an athero-protective and to an anti-metabolic syndrome profile.

The ability of the 18A-C-II peptide in reducing triglycerides is believed to be useful to treat conditions that lead to hypertriglyceridemia such as pancreatitis, metabolic syndrome, LPL deficiency, and high triglycerides induced by apoA-I mimetic therapies. Moreover, the cholesterol lowering effect is believed to be a potential new alternative treatment to conditions such as familial hypercholesterolemia and other high cholesterol dyslipidemias.

Example 10

Identification of Peptides that Promote ABCA1-Dependent Lipid Efflux and Activate Lipoprotein Lipase This example illustrates a method for identifying peptides that promote ABCA1-dependent lipid efflux from cells and activates lipoprotein lipase within cells.

Peptide Design:

Based on the principals and procedures described in the present application, an amino acid sequence can be designed for a peptide that promotes lipid efflux and is capable of activating lipoprotein lipase. In one example, the peptide contains one amphipathic α-helix, with relatively high lipid affinity, and an apoC-II domain (such as those provided in Table 3 above). The apoC-II domain can be in the form of an α-helix resulting in a peptide with two α-helices. Alternatively, the apoC-II domain can be incorporated into one or more of the amphipathic α-helical domains of the multi-domain peptides designed and produced according to methods disclosed herein (such as those provided in Example 7).

Peptide Production:

Peptides to be tested can be produced synthetically or by recombinant DNA methods, as described in the present application, and purified by reverse phase HPLC or other suitable techniques well known to one of skill in the art. In a particular example, the peptide provided in Table 4 can be synthesized and purified.

Peptide Cytotoxicity Testing:

Peptides can be tested for cytotoxicity by any number of methods well known to one of skill in the art, such as the release of intracellular LDH (Example 4), the release of hemoglobin from red blood cells (Example 6) or evaluating the in vivo effects of the peptide on various serum biomarkers (Example 8) or triglyceride levels. Such studies are performed by incubating various concentrations of the peptides with a cell line, a vesicle or red blood cells, or administrating various concentrations of the peptide to the subject as described herein.

Peptide ABCA1-Specificity for Lipid Efflux:

Peptides to be tested can be added to serum-free cell culture media in the approximate concentration range of 1-20 micromolar (μM) and incubated with a control cell line that does not express the ABCA1 transporter and the same cell line after transfection with human cDNA for the ABCA1 transporter, as described herein. Alternatively, cells, such as macrophages, that either express or do not express the ABCA1 transporter depending on their cholesterol content and/or exposure to agents that induce the ABCA1 transporter (e.g., cAMP and LXR agonists) can also be used. After a suitable period of approximately 4 to 24 hours, the conditioned media can be removed from the cells and the amount of cholesterol and or phospholipid effluxed can be quantified, as described herein. ABCA1-specific lipid efflux is calculated by subtracting the total lipid efflux from the ABCA1 expressing cell line from the results obtained from the cell line that does not express the ABCA1 transporter. To determine the ability of peptides to stimulate lipid efflux in vivo, increasing concentrations (3.75 mg/kg; 7.5 mg/kg; 15 mg/kg; 30 mg/kg; 60 mg/kg; 120 mg/kg; or 240 mg/kg) of the peptide can be administered intravenously to wild-type mice over a 24 hour period. Plasma cholesterol levels can then be measured.

Peptide Activation of Lipoprotein Lipase (LPL):

For measurement of LPL activity an assay mixture of 200 μl containing 2 mg of triacylglycerols from the lipid emulsion can be used. The medium can contain 0.1 M NaCl, 0.1 M Tris-Cl, 20 μg of heparin, and 12 mg of bovine serum albumin (pH 8.5). To study the activation, peptides can be dissolved in 5 M urea, 10 mM Tris-Cl (pH 8.2). Known activators of LPL, such as apoC-II, can be used as a positive control. The protein concentration can be determined by a bicinchoninic acid protein assay. Five μl of the stock solution of apoC-II, or the same volume of dilutions in 5 M urea, 10 mM Tris (pH 8.2), can be added to the incubations. The reactions can be started by addition of LPL and stopped after incubation for 15 min at 25° C. by addition of organic solvents for extraction of the labeled free fatty acids. The lipase activity is expressed in units/mg of LPL, where 1 unit corresponds to release of 1 μmol of fatty acid per minute. An at least 10% increase in LPL activity and or a statistically significant increase (3× the CV of the lipase assay) in LPL activity in the presence of a test peptide as compared to LPL activity in the absence of the test peptide, identifies the peptide as an LPL activating peptide. The ability of the test peptides to activate LPL in vivo, can be determined by administering one or more of the peptides. Triglycerides levels in a sample taken from a subject receiving the peptide alone can then be compared to those levels present in a sample taken prior to the subject receiving the peptide or compared to a reference sample containing a known amount of triglycerides. Triglyceride levels of less than 150 mg/dl following peptide administration indicate that the peptide is an LPL activator.

Example 11

Associating a Peptide Capable of Promoting Lipid Efflux and Activating Lipoprotein Lipase with an Implant According to the teachings herein, one or more peptides that promote ABCA1 specific lipid efflux and/or activate LPL, or a combination thereof, can be placed in a suitable container, such as a tissue microcapsule implant, and placed within a subject to allow continuous, slow release of one or more of the disclosed peptides. Such peptides can either be used in the free state or after complexation with lipid.

Example 12

Method of Treating or Inhibiting a Dyslipidemic or Vascular Disorder in a Subject According to the teachings herein, one or more of the disclosed peptides capable of stimulating cholesterol efflux and activating lipoprotein lipase can be used to prevent, treat or inhibit a dyslipidemic or vascular disorder in a subject without causing a substantial cytotoxic effect. A method of treating or inhibiting a dyslipidemic or vascular disorder in a subject includes administering to the subject a therapeutically effective amount of the pharmaceutical composition including one or more of the peptides disclosed herein. A therapeutically effective amount of the pharmaceutical composition is one that results in triglyceride levels of less than 150 mg/dl while causing lipid efflux. In a particular example, the pharmaceutical composition is a peptide that is capable of causing by lipid efflux and activating lipoprotein lipase (including a peptide with an amino acid sequence provided by any one of SEQ ID NOs: 70-75), thereby resulting in triglyceride levels of less than 150 mg/dl. For example, a pharmaceutical composition including a peptide with the amino acid sequence of SEQ ID NO: 70 is provided at a therapeutically effective amount to a subject so that triglyceride levels in the subject are 150 mg/dl or less, such as between 150 mg/dl and 10 mg/dl, 140 mg/dl and 25 mg/dl, 120 mg/dl and 50 mg/dl, including 140 mg/dl, 130 mg/dl, 120 mg/dl, 110 mg/dl, 100 mg/dl, 90 mg/dl, 80 mg/dl, 70 mg/dl, 60 mg/dl, 50 mg/dl, 40 mg/dl, 30 mg/dl, 20 mg/dl, or 10 mg/dl, while plasma cholesterol levels are reduced by at least 20%, such as at least 30%, at least 40%, at least 50%, at least 60%, at least 70%, at least 75%, at least 80%, at least 85%, at least 90%, at least 95% percent, including 22%, 25%, 30%, 35%, 40%, 45%, 50%, 55%, 60%, 65%, 70%, 75%, 80%, 85%, 90%, 95%, or 98%.

In another particular example, the pharmaceutical composition includes at least two peptides, one that is capable of causing lipid efflux and another that is capable of activating lipoprotein lipase. In a certain example, a pharmaceutical composition including a peptide with an amino acid sequence set forth in any one of SEQ ID NOs: 3-45 and an apoC-II peptide with an amino acid sequence set forth in any one of SEQ ID NOs: 63-69. These peptides need not be covalently attached one to another. In a specific example, the pharmaceutical composition includes a peptide with an amino acid sequence set forth in SEQ ID NO: 3 and an apoC-II peptide with an amino acid sequence set forth SEQ ID NO: 63. This pharmaceutical composition is provided at a therapeutically effective amount to a subject so that triglyceride levels are 150 mg/dl or less, such as between 150 mg/dl and 10 mg/dl, 140 mg/dl and 25 mg/dl, 120 mg/dl and 50 mg/dl, including 140 mg/dl, 130 mg/dl, 120 mg/dl, 110 mg/dl, 100 mg/dl, 90 mg/dl, 80 mg/dl, 70 mg/dl, 60 mg/dl, 50 mg/dl, 40 mg/dl, 30 mg/dl, 20 mg/dl, or 10 mg/dl, while plasma cholesterol levels are reduced by at least 20%, such as at least 30%, at least 40%, at least 50%, at least 60%, at least 70%, at least 75%, at least 80%, at least 85%, at least 90%, at least 95% percent, including 22%, 25%, 30%, 35%, 40%, 45%, 50%, 55%, 60%, 65%, 70%, 75%, 80%, 85%, 90%, 95%, or 98%.

It will be apparent that the precise details of the constructs, compositions, and methods described herein may be varied or modified without departing from the spirit of the described invention. We claim all such modifications and variations that fall within the scope and spirit of the claims below.

We claim:

1. An isolated peptide, comprising:
a first domain capable of promoting lipid efflux from cells by an ABCA1-dependent pathway; and
a second domain capable of activating lipoprotein lipase, wherein the first domain comprises amino acids 1-18 of SEQ ID NO: 70 and the second domain comprises the amino acid sequence of any one of SEQ ID NOs: 63-68.

2. The isolated peptide of claim 1, further comprising a linker connecting the first domain to the second domain.

3. The isolated peptide of claim 2, wherein the linker comprises glycine, alanine or proline.

4. The isolated peptide of claim 3, wherein the linker comprises proline.

5. The isolated peptide of claim 1, further comprising at least one additional peptide domain.

6. The isolated peptide of claim 5, wherein the additional peptide domain comprises a heparin binding site, an integrin binding site, a P-selectin site, a TAT HIV sequence, a panning sequence, a penatratin sequence, a SAA C-terminus sequence, a SAA N-terminus sequence, a LDL receptor sequence, a modified 18A sequence, an apoA-I Milano sequence, a 6×-His sequence, a lactoferrin sequence, or combinations of two or more thereof.

7. The isolated peptide of claim 1, wherein the peptide comprises an amino acid sequence as set forth in any one of SEQ ID NOs: 70-75.

8. A pharmaceutical composition, comprising the isolated peptide of claim 1, and a pharmaceutically acceptable carrier.

9. A method of treating or inhibiting hyperlipidemia, hyperlipoproteinemia, hypercholesterolemia, hypertriglyceridemia, or a combination of two or more thereof in a subject, comprising administering to the subject a therapeutically effective amount of the pharmaceutical composition according to claim 8.

10. The method of claim 9, further comprising administering an additional lipid lowering composition.

11. The method of claim 9, wherein the pharmaceutical composition is delivered on an implant.

12. The method of claim 9, wherein administering to the subject a therapeutically effective amount of the pharmaceutical composition comprises implanting in a heart or peripheral vasculature of the subject an implant comprising the pharmaceutical composition.

13. An implant coated with the peptide of claim 1.

14. The implant of claim 13, wherein the peptide further comprises at least one additional peptide domain.

15. The implant of claim 14, wherein the additional peptide domain comprises a heparin binding site, an integrin binding site, a P-selectin site, a TAT HIV sequence, a panning sequence, a penatratin sequence, a SAA C-terminus sequence, a SAA N-terminus sequence, a LDL receptor sequence, a modified 18A sequence, an apoA-I Milano sequence, a 6×-His sequence, a lactoferrin sequence, or combinations of two or more thereof.

16. An isolated peptide, comprising:
a first domain capable of promoting lipid efflux from cells by an ABCA1-dependent pathway; and
a second domain capable of activating lipoprotein lipase, wherein the first domain comprises amino acids 1-18 of SEQ ID NO: 70 and the second domain comprises an amphipathic α-helical domain comprising an amino acid sequence at least 90% identical to SEQ ID NO: 16.

17. A pharmaceutical composition comprising the isolated peptide of claim 16, and a pharmaceutically acceptable carrier.

18. A method of treating or inhibiting hyperlipidemia, hyperlipoproteinemia, hypercholesterolemia, hypertriglyceridemia, or a combination of two or more thereof in a subject, comprising administering to the subject a therapeutically effective amount of the pharmaceutical composition according to claim 17.

19. A method of treating or inhibiting hyperlipidemia, hyperlipoproteinemia, hypercholesterolemia, hypertriglyceridemia, or a combination of two or more thereof in a subject, comprising co-administering to the subject a therapeutically effective amount of an isolated peptide comprising an amino acid sequence set forth in any one of SEQ ID NOs: 3-45 (which promotes lipid efflux) and an isolated peptide comprising an amino acid sequence set forth in any one of SEQ ID NOs: 63-69 (which activates lipoprotein lipase), thereby treating or inhibiting the hyperlipidemia, hyperlipoproteinemia, hypercholesterolemia, hypertriglyceridemia, or a combination of two or more thereof in the subject.

20. The method of claim 19, wherein the lipid efflux promoting isolated peptide and the lipoprotein lipase activating peptide are administered within the same delivery vehicle.

* * * * *

UNITED STATES PATENT AND TRADEMARK OFFICE
CERTIFICATE OF CORRECTION

| | | |
|---|---|---|
| PATENT NO. | : 8,936,787 B2 | Page 1 of 1 |
| APPLICATION NO. | : 12/937974 | |
| DATED | : January 20, 2015 | |
| INVENTOR(S) | : Alan T. Remaley et al. | |

It is certified that error appears in the above-identified patent and that said Letters Patent is hereby corrected as shown below:

In the Claims:

Claim 16, Column 88, line 11, "SEQ ID NO: 16." should read --SEQ ID NO: 65.--.

Signed and Sealed this
Third Day of May, 2016

Michelle K. Lee
*Director of the United States Patent and Trademark Office*